(12) United States Patent
Wadsworth et al.

(10) Patent No.: US 10,640,771 B2
(45) Date of Patent: May 5, 2020

(54) COMPOSITIONS AND METHODS FOR TREATING AND PREVENTING MACULAR DEGENERATION

(71) Applicants: GENZYME CORPORATION, Cambridge, MA (US); THE UNITED STATES OF AMERICA, AS REPRESENTED BY THE SECRETARY, DEPARTMENT OF HEALTH AND HUMAN SERVICES, Bethesda, MD (US)

(72) Inventors: Samuel Wadsworth, Shrewsbury, MA (US); Abraham Scaria, Framingham, MA (US); Chi-Chao Chan, Burlingame, CA (US)

(73) Assignees: GENZYME CORPORATION, Cambridge, MA (US); THE UNITED STATES OF AMERICA AS REPRESENTED BY THE, Rockville, MD (US)

( * ) Notice: Subject to any disclaimer, the term of this patent is extended or adjusted under 35 U.S.C. 154(b) by 0 days.

(21) Appl. No.: 14/785,159

(22) PCT Filed: Apr. 17, 2014

(86) PCT No.: PCT/US2014/034538
§ 371 (c)(1),
(2) Date: Oct. 16, 2015

(87) PCT Pub. No.: WO2014/172560
PCT Pub. Date: Oct. 23, 2014

(65) Prior Publication Data
US 2016/0068844 A1 Mar. 10, 2016

Related U.S. Application Data

(60) Provisional application No. 61/813,014, filed on Apr. 17, 2013.

(51) Int. Cl.
| C12N 15/113 | (2010.01) |
| A61K 38/17 | (2006.01) |
| C07K 14/715 | (2006.01) |

(52) U.S. Cl.
CPC ...... *C12N 15/1136* (2013.01); *A61K 38/1793* (2013.01); *C07K 14/7155* (2013.01); *C07K 2319/30* (2013.01); *C12N 2750/14143* (2013.01)

(58) Field of Classification Search
CPC ............ A61K 38/1793; C07K 14/7155; C07K 2319/30; C12N 15/1136; C12N 2750/14143
USPC .................................................... 424/93.21
See application file for complete search history.

(56) References Cited

U.S. PATENT DOCUMENTS

| 4,657,760 A | 4/1987 | Kung et al. |
| 5,139,941 A | 8/1992 | Muzycka et al. |
| 5,173,414 A | 12/1992 | Lebkowski et al. |
| 5,206,344 A | 4/1993 | Katre et al. |
| 5,219,740 A | 6/1993 | Miller et al. |
| 5,225,212 A | 7/1993 | Martin et al. |
| 5,580,859 A | 12/1996 | Felgner et al. |
| 5,589,466 A | 12/1996 | Felgner et al. |
| 5,622,856 A | 4/1997 | Natsoulis |
| 5,693,622 A | 12/1997 | Wolff et al. |
| 5,731,168 A | 3/1998 | Carter et al. |
| 5,763,270 A | 6/1998 | Eastman et al. |
| 6,001,650 A | 12/1999 | Colosi |
| 6,004,797 A | 12/1999 | Colosi |
| 6,048,551 A | 4/2000 | Hilfinger et al. |
| 6,214,804 B1 | 4/2001 | Felgner et al. |
| 6,306,652 B1 | 10/2001 | Fallaux et al. |
| 6,413,942 B1 | 7/2002 | Felgner et al. |
| 6,566,118 B1 | 5/2003 | Atkinson et al. |
| 6,596,535 B1 | 7/2003 | Carter |
| 6,723,551 B2 | 4/2004 | Kotin et al. |
| 6,989,264 B2 | 1/2006 | Atkinson et al. |
| 7,125,717 B2 | 10/2006 | Carter |
| 7,256,264 B2 | 8/2007 | Goddard et al. |
| 7,765,583 B2 | 7/2010 | Kalonji et al. |
| 7,785,888 B2 | 8/2010 | Carter |
| 7,790,154 B2 | 9/2010 | Samulski et al. |
| 7,846,729 B2 | 12/2010 | Carter |
| 8,093,054 B2 | 1/2012 | Carter |
| 8,137,948 B2 | 3/2012 | Qu et al. |
| 8,361,457 B2 | 1/2013 | Samulski et al. |

FOREIGN PATENT DOCUMENTS

| WO | WO-89/03429 A1 | 4/1989 |
| WO | WO-91/12882 A1 | 9/1991 |
| WO | WO-92/01070 A1 | 1/1992 |
| WO | WO-92/03545 A1 | 3/1992 |

(Continued)

OTHER PUBLICATIONS

Hasegawa et al. Jan. 2013, The Journal of Immunology 190(4), 1778-1787.*
Liu et al. Journal of Translational Medicine 2011, 9:111, pp. 1-12.*
Aiello et al. (1979) "Adenovirus 5 DNA Sequences Present and RNA Sequences Transcribed in Transformed Human Embryo Kidney Cells (HEK-Ad-5 or 293)" *Virology* 94:460-469.
Ardeljan et al. (Apr. 2014) "Interleukin-17 Retinotoxicity Is Prevented by Gene Transfer of a Soluble Interleukin-17 Receptor Acting As a Cytokine Blocker: Implications for Age-Related Macular Degeneration", *PLoS ONE* 9(4): e95900.

(Continued)

*Primary Examiner* — Janet L Epps-Smith
(74) *Attorney, Agent, or Firm* — Morrison & Foerster LLP

(57) ABSTRACT

Compositions and methods for treating macular degeneration are disclosed. The methods utilize IL17 inhibitors, such as IL17 receptors, as well as fusion proteins including an IL17 receptor fused with a multimerization domain, and recombinant viral vectors encoding such fusions.

16 Claims, 15 Drawing Sheets
Specification includes a Sequence Listing.

(56) References Cited

FOREIGN PATENT DOCUMENTS

| WO | WO-93/03769 A1 | 3/1993 | |
|----|----|----|----|
| WO | WO-95/07995 A2 | 3/1995 | |
| WO | WO-96/17072 A2 | 6/1996 | |
| WO | WO-97/17458 A1 | 5/1997 | |
| WO | WO-01/02440 A1 | 1/2001 | |
| WO | WO-01/83797 A2 | 11/2001 | |
| WO | WO-02/12455 A1 | 2/2002 | |
| WO | WO2009/042162 A2 * | 4/2009 | |
| WO | WO-2009/042162 A2 | 4/2009 | |
| WO | WO-2010/148143 | 12/2010 | |
| WO | WO-2012/103187 A2 | 8/2012 | |
| WO | WO-2014107737 A2 * | 7/2014 | ......... A61K 39/3955 |

OTHER PUBLICATIONS

Auricchio et al. (2002) "Inhibition of Retinal Neovascularization by Intraocular Viral-Mediated Delivery of Anti-angiogenic Agents," *Mol. Ther.* 6:490-494.

Barr et al. (1994) "Efficient Catheter-Mediated Gene Transfer into the Heart Using Replication-Defective Adenovirus," *Gene Therapy* 1:51-58.

Bennett et al. (1996) "Photoreceptor Cell Rescue in Retinal Degeneration (rd) Mice by in vivo Gene Therapy," *Nature Med.* 2(6):649-654.

Ben-Shabat et al. (2001) "Fluorescent Pigments of the Retinal Pigment Epithelium and Age-Related Macular Degeneration," *Bioorganic & Med. Chem. Lett.* 11:1533-1540.

Berkner, K.L. (1988) "Development of Adenovirus Vectors for the Expression of Heterologous Genes," *BioTechniques* 6:616-629.

Bett et al. (1993) "Packaging Capacity and Stability of Human Adenovirus Type 5 Vectors," *J. Virol.* 67(10):5911-5921.

Boris-Lawrie et al. (1993) "Recent Advances in Retrovirus Vector Technology," *Cur. Opin. Genet. Develop.* 3:102-109.

Borras, Teresa (2003) "Recent Developments in Ocular Gene Therapy," *Experimental Eye Research* 76:643-652.

Bossis, I. et al. (2003) "Cloning of an Avian Adeno-Associated Virus (AAAV) and Generation of Recombinant AAAV Particles," *Journal of Virology* 77(12): 6799-6810.

Buller et al. (1981) "Herpes Simplex Virus Types 1 and 2 Completely Help Adenovirus-Associated Virus Replication," *J. Virol.* 40(1):241-247.

Burcin et al. (1999) "Adenovirus-Mediated Regulable Target Gene Expression in vivo," *Proc. Natl. Acad. Sci. USA* 96:355-360.

Burns et al. (1993) "Vesicular Stomatitis Virus G Glycoprotein Pseudotyped Retroviral Vectors: Concentration to Very High Titer and Efficient Gene Transfer into Mammalian and Nonmammalian Cells," *Proc. Natl. Acad. Sci. USA* 90:8033-8037.

Burton, Dennis R. (1985) "Immunoglobulin G: Functional Sites," *Molec. immunol.* 22(3):161-206.

Campochiaro, Peter A. (2002) "Gene Therapy for Retinal and Choroidal Diseases," *Expert Opinions in Biological Therapy* 2:537-544.

Carter et al. (1983) "Properties of an Adenovirus Type 2 Mutant, Ad2dl807, Having a Deletion Near the Right-Hand Genome Terminus: Failure to Help AAV Replication," *Virology* 126:505-516.

Carter, B.J. (1992) "Adeno-Associated Virus Vectors," *Current Opinion in Biotechnology* 3:533-539.

Chan et al. (2008) "Ccl2/Cx3cr1-Deficient Mice: An Animal Model for Age-Related Macular Degeneration," *Ophthalmic Res* 40:124-128.

Chaum, E. (2002) "Gene Therapy for Genetic and Acquired Retinal Diseases," *Survey of Ophthalmology* 47(5):449-469.

Chen et al. (2011) "IL-17A Stimulates the Production of Inflammatory Mediators Via Erk1/2, p38 MAPK, PI3K/Akt, and NF-κB pathways in ARPE-19 cells," *Mol Vis* 17:3072-3077.

Chen et al. (2011) "The Effects of Th17 Cytokines on the Inflammatory Mediator Production and Barrier Function of ARPE-19 Cells," *PLoS ONE* 6(3):e18139.

Chu et al. (1981) "SV40 DNA Transfection of Cells in Suspension: Analysis of the Efficiency of Transcription and Translation of T-antigen," *Gene* 13:197-202.

Clark et al. (1999) "Highly Purified Recombinant Adeno-Associated Virus Vectors are Biologically Active and Free of Detectable Helper and Wild-Type Viruses," *Hum. Gene Ther.* 10:1031-1039.

Curcio et al. (1996) "Photoreceptor Loss in Age-Related Macular Degeneration," *Invest Ophthalmol.Vis. Sci.* 37:1236-1249.

Davidson et al. (2000) "Recombinant Adeno-Associated Virus Type 2, 4 and 5 Vectors: Transduction of Variant Cell Types and Regions in the Mammalian Central Nervous System," *PNAS* 97(7):3428-3432.

Dridi et al. (2012) "ERK1/2 Activation is a Therapeutic Target in Age-Related Macular Degeneration," *PNAS* 109(34):13781-13786.

Dubensky et al. (1996) "Sindbis Virus DNA-Based Expression Vectors: Utility for In Vitro and In Vivo Gene Transfer," *J. Virol.* 70:508-519.

Edge, et al. (1981) "Total Synthesis of a Human Leukocyte Interferon Gene," *Nature* 292:756-762.

Edwards et al. (2005) "Complement Factor H Polymorphism and Age-Related Macular Degeneration," *Science* 308:421-424.

Fisher et al. (1996) "Transduction with Recombinant Adeno-Associated Virus for Gene Therapy is Limited by Leading-Strand Synthesis," *J. Virol.* 70:520-532.

Gaffen, Sarah L. (Aug. 2009). "Structure and signalling in the IL-17 receptor family", *Nature Reviews Immunology* 9(8):556-567.

Gao et al. (2002) "Novel Adeno-Associated Viruses from Rhesus Monkeys as Vectors for Human Gene Therapy," *PNAS* 99(18): 11854-11859.

Gao et al. (2003) "Adeno-Associated Viruses Undergo Substantial Evolution in Primates During Natural Infections," *PNAS* 100(10):6081-6086.

Gao et al. (2004) "Clades of Adeno-Associated Viruses are Widely Disseminated in Human Tissues," *J. Virol.* 78(12):6381-6388.

Graham et al. (1973) "A New Technique for the Assay of Infectivity of Human Adenovirus 5 DNA," *Virology*, 52:456-467.

Graham et al. (1977) "Characteristics of a Human Cell Line Transformed by DNA from Human Adenovirus Type 5," *J. Gen. Virol.* 36:59-72.

Haj-Ahmad et al. (1986) "Development of a Helper-Independent Human Adenovirus Vector and Its Use in the Transfer of the Herpes Simplex Virus Thymidine Kinase Gene," *J. Virol.* 57(1):267-274.

Handa et al. (1975) "Complementation of Adeno-Associated Virus Growth with Temperature-Sensitive Mutants of Human Adenovirus Types 12 and 5," *J. Gen. Virol.* 29:239-242.

Hasegawa et al. (Jan. 2013) "IL-23—Independent Induction of IL-17 from γδT Cells and Innate Lymphoid Cells Promotes Experimental Intraocuiar Neovascularization", *The Journal of Immunology* 190(4):1778-1787.

Hecker et al. (2010) "Genetic Control of the Alternative Pathway of Complement in Humans and Age-Related Macular Degeneration," *Hum Mol Genet* 19(1):209-215.

Hu et al. (2010) "Novel CSF Biomarkers for Frontotemporal Lobar Degenerations," *Neurology* 75:2079-2086.

International Search Report and Written Opinion dated Sep. 4, 2014, for PCT Application No. PCT/US2014/034538; 14 pages.

Ishibashi et al (1971) "The Potentiation of Type 1 Adeno-Associated Virus by Temperature-Sensitive Conditional-Lethal Mutants of CELO Virus at the Restrictive Temperature," *Virology* 45:317-320.

Ishigame et al. (2009) "Differential Roles of Interleukin-17A and -17F in Host Defense Against Mucoepithelial Bacterial Infection and Allergic Responses," *Immunity* 30:108-119.

Ito et al. (1970) "Adeno-Associated Satellite Virus Growth Supported by a Temperature-sensitive Mutant of Human Adenovirus," *J. Gen. Virol.* 9:243.

Janik et al. (1981) "Locations of Adenovirus Genes Required for the Replication of Adenovirus-Associated Virus," *Proc. Natl. Acad. Sci. USA* 78(3):1925-1929.

Jay et al. (1981) "Eukaryotic Translational Control: Adeno-Associated Virus Protein Synthesis is Affected by a Mutation in the Adenovirus DNA-binding Protein," *Proc. Natl. Acad. Sci. USA* 78(5):2927-2931.

(56) References Cited

OTHER PUBLICATIONS

Jay et al. (1984) "Chemical Synthesis of a Biologically Active Gene for Human Immune Interferon-γ," *J. Biol. Chem.* 259(10):6311-6317.
Jayaraman et al. (1991) "Polymerase Chain Reaction-Mediated Gene Synthesis: Synthesis of a Gene Coding for Iozyme c of Horseradish Peroxidase," *Proc. Natl. Acad. Sci. USA* 88:4084-4088.
Jones et al. (1986) "Replacing the Complementarity-Determining Regions in a Human Antibody with Those from a Mouse," *Nature* 321:522-525.
Karan et al (2005) "Lipofuscin Accumulation, Abnormal Electrophysiology, and Photoreceptor Degeneration in mutant ELOVL4 Transgenic Mice: A Model for Macular Degeneration," *Proc. Natl. Acad. Sci. USA* (2005) 102:4164-4169.
Kotin, R. M. (1994) "Prospects for the Use of Adeno-Associated Virus as a Vector for Human Gene Therapy," *Hum. Gene Ther.* 5:793-801.
Kyte et al. (1982) "A Simple Method for Displaying the Hydropathic Character of a Protein," *J. Mol. Biol.* 157:105-132.
Lai et al. (2002) "Potential Long-Term Inhibition of Ocular Neovascularisation by Recombinant Adeno-Associated Virus-Mediated Secretion Gene Therapy," *Gene Therapy* 9:804 813.
Laughlin et al. (1982) "Effect of Deletions in Adenovirus Early Region 1 Genes Upon Replication of Adeno-Associated Virus," *J. Virol.* 41(3):868-876.
Lebkowski et al. (1988) "Adeno-Associated Virus: a Vector System for Efficient Introduction and Integration of DNA into a Variety of Mammalian Cell Types," *Molec. Cell. Biol.* 8(10):3988-3996.
Liu et al. (2011) "Complement Component C5a Promotes Expression of IL-22 and IL-17 from Human T Cells and Its Implication in Age-related Macular Degeneration," *J Transl Med* 9:111.
Maclachlan et al. (2011) "Preclinical Safety Evaluation of AAV2-sFLT01—A Gene Therapy for Age-related Macular Degeneration," *Molecular Therapy* 19(2):326-334.
Matshushita et al. (1998) "Adeno-Associated Virus Vectors Can Be Efficiently Produced without Helper Virus," *Gene Therapy* 5:938-945.
Mattapallil et al. (2012) "The Rd8 Mutation of the Crb1 Gene is Present in Vendor Lines of C57BL/6N Mice and Embryonic Stem Cells, and Confounds Ocular Induced Mutant Phenotypes," *Invest Ophthalmol Vis Sci.* 53(6):2921-2927.
McCarty et al. (1991) "Sequences Required for Coordinate Induction of Adeno-Associated Virus p19 and p40 Promoters by Rep Protein," *J. Virol.* 65(6):2936-2945.
McLaughlin et al. (1988) "Adeno-Associated Virus General Transduction Vectors: Analysis of Provirus Structures," *J. Virol.*, 62(6):1963-1973.
McPherson et al. (1985) "Human Cytomegalovirus Completely Helps Adeno-Associated Virus Replication," *Virology* 147:217-222.
Michael et al. (1993) "Binding-incompetent Adenovirus Facilitates Molecular Conjugate-mediated Gene Transfer by the Receptor-mediated Endocytosis Pathway," *J. Biol. Chem.* 268(10):6866-6869.
Miller et al. (1989) "Improved Retroviral Vectors for Gene Transfer and Expression," *BioTechniques* 7(9):980-990.
Miller, A.D. (1990) "Retrovirus Packaging Cells," *Human Gene Therapy* 1:5-14.
Mittereder et al. (1994) "Evaluation of the Efficacy and Safety of In Vitro, Adeno-Mediated Transfer of the Human Cystic Fibrosis Transmembrane Conductance Regulator cDNA," *Human Gene Therapy* (1994) 5:717-729.
Muzyczka, N. (1992) "Use of Adeno-Associated Virus as a General Transduction Vecotr for Mammalian Cells," *Current Topics in Microbiol. and Immunol.*158:97-129.
Myers et al. (1980) "Adenovirus Helper Function for Growith of Adeno-Associated Virus: Effect of Temperature-Sensitive Mutations in Adenovirus Early Gene Region 2," *J. Virol.* 35(1):65-75.
Myers et al. (1981) "Adeno-Associated Virus Replication," *J. Biol. Chem.* 256(2):567-570.

Nambiar et al. (1984) "Total Synthesis and Cloning of a Gene Coding for the Ribonuclease S Protein," *Science* 223:1299-1301.
Nielsen et al. (1997) "Identification of Prokaryotic and Eukaryotic Signal Peptides and Prediction of their Cleavage Site," *Prot. Eng.* 10:1-6.
Nozaki et al (2006) "Drusen Complement Components C3a and C5 Promote Choroidal Neovascularization," *Proc. Natl. Acad. Sci.U. S.A* 103:2328-2333.
Ostrove et al., (1980) "Adenovirus Early Region 1b Gene Function Required for Rescue of Latent Adeno-Associated Virus," *Virology* 104:502-505.
Parks, R.J. (2000) "Improvements in Adenoviral Vector Technology: overcoming barriers for gene therapy," *Clin. Genet.* 58:1-11.
Passini et al. (2003) "Intraventricular Brain Injection of Adeno-Associated Virus Type 1 (AAV1) in Neonatal Mice Results in Complementary Patterns of Neuronal Transduction to AAV2 and Total Long-Term Correction of Storage Lesions in the Brains of β-Glucuronidase-Deficient Mice," *J. Virol.*, 2003, 77(12):7034-40.
Pechan et al. (2009) "Novel anti-VEGF Chimeric Molecules Delivered by AAV Vectors for Inhibition of Retinal Neovascularization," *Gene Ther.* 16:10-16.
Pleyer (2003) "Gene Therapy in Immune-Mediated Diseases of the Eye," *Progress in Retinal and Eye Research* 22:277-293.
Queen et al. (1989) "A Humanized Antibody that Binds to the Interleukin 2 Receptor," *Proc. Natl. Acad. Sci. USA* 86:10029-10033.
Reynolds et al. (2009) "Plasma Complement Components and Activation Fragments: Associations with Age-Related Macular Degeneration Genotypes and Phenotypes," *Invest Ophthalmol Vis Sci* 50(12):5818-5827.
Rich et al. (1993) "Development and Analysis of Recombinant Adenoviruses for Gene Therapy of Cystic Fibrosis," *Human Gene Therapy* 4:461-476.
Riechmann et al. (1988) "Reshaping Human Antibodies for Therapy," *Nature* 332:323-327.
Ross et al. (2008) "Immunological Protein Expression Profile in Ccl2/Cx3cr1 Deficient Mice with Lesions Similar to Age-Related Macular Degeneration," *Exp.Eye Res.* 86:675-683.
Samulski et al. (1989) "Helper-Free Stocks of Recombinant Adeno-Associated Viruses: Normal Integration Does Not Require Viral Gene Expression," *J. Virol.* 63:3822-3828.
Samulski et al. (1988) "Adenovirus E1B 55-M, Polypeptide Facilitates Timely Cytoplasmic Accumulation of Adeno-Associated Virus mRNAs," *J. Virol.* 62(1):206-210.
Scarpa et al. (1991) "Characterization of Recombinant Helper Retroviruses from Maloney-Based Vectors in Ecotropic and Amphotropic Packaging Cell Lines," *Virology* 180:849-852.
Schlehofer et al. (1986) "Vaccinia Virus, Herpes Simplex Virus, and Carcinogens Induc DNA Amplification in a Human Cell Line and Support Replication of a Helpervirus Dependent Parvovirus," *Virology* 152:110-117.
Scholl et al. (2008) "Systemic Complement Activation in Age-Related Macular Degeneration," *PLoS ONE* 3(7):e2593.
Schwartz, R. M. et al. (1978) "Matrices for Detecting Distant Relationships," Chapter 23 in *Atlas of Protein Sequence and Structure* vol. 5, Issue 3:353-358.
Seth et al. (1994) "Mechanism of Enhancement of DNA Expression Consequent to Cointernalization of a Replication-Deficient Adenovirus and Unmodified Plasmid DNA," *J. Virol.* 68(2):933-940.
Shelling, Andrew N. et al. (1994) "Targeted Integration of Transfected and Infected Adeno-Associated Virus Vectors Containing the Neomycin Resistance Gene," *Gene Therapy* 1:165-169.
Shen et al. (2011) "Naloxene Ameliorates Retinal Lesions in Ccl2/Cx3cr1 Double-Deficient Mice via Modulation of Microglia," *Invest Ophthalmol Vis Sci* 52(6):2897-2904.
Smith et al. (1981) "Comparison of Biosequences," *Advances in Appl. Math.* 2:482-489.
Strauss et al. (1976) "DNA-Minus Temperature-Sensitive Mutants of Adenovirus Type 5 Help Adenovirus-Associated Virus Replication," *J. Virol.* 17(1):140-148.
Thomson et al. (1994) "Human Herpesvirus 6 (HHV-6) is a Helper Virus for Adeno-Associated Virus Type 2 (AAV-2) and the AAV-2

(56) References Cited

OTHER PUBLICATIONS rep Gene Homologue in HHV-6 can Mediate AAV-2 DNA Replication and Regulate Gene Expression," *Virology* 204:304-311.
Tsai et al. (2000) "Adenovirus-mediated Transfer of Regulable Gene Expression," *Curr. Opin. Mol. Ther.* 2:516-524.
Tuo et al. (Feb. 2012) "AAV5-mediated sFLT01 gene therapy arrests retinal lesions in Ccl2$^{-/-}$/Cx3cr1$^{-/-}$ mice", *Neurobiology of Aging*, 33(2): pp. 433.e1-433.e10.
Tuo et al. (Mar. 2012). "Anti-inflammatory recombinant TSG-6 stabilizes the progression of focal retinal degeneration in a murine model," *Journal of Neuroinflammation* 9:59.
Tuo et al. (2007) "Murine Ccl2/Cx3cr1 Deficiency Results in Retinal Lesions Mimicking Human Age-Related Macular Degeneration," *Invest Ophthalmol Vis Sci* 48(8):3827-3836.
Veldwijk et al. (2002) "Development and Optimization of a Real-Time Quantitative PCR-Based Method for the Titration of AAV-2 Vector Stocks," *Mol. Ther.* 6:272-278.
Verhoeyen et al. (1988) "Reshaping Human Antibodies: Grafting an Antilysozyme Activity," *Science* 239:1534-1536.
Vincent et al. (1997) "Analysis of Recombinant Adeno-Associated Virus Packaging and Requirements for rep and cap Gene Products," *J Virol* 71(3):1897-1905.
Von Heinje, Gunnar (1986) "A New Method for Predicting Signal Sequence Cleavage Sites," *Nucl. Acids. Res.* 14(11):4683-4690.
Wagner et al. (1992) "Influenza Virus Hemagglutinin Ha-2 N-Terminal Fusogenic Peptides Augment Gene Transfer by Transferrin-Polylysine-DNA Complexes: Toward a Synthetic Virus-like Gene-transfer Vehicle," *Proc. Natl. Acad. Sci. USA* 89:7934-7938.
Wang, Z. et al. (2003) "Rapid and Highly Efficient Transduction by Double-Stranded Adeno-Associated Virus Vectors in vitro and in vivo," Gene Ther 10:2105-2111.
Wei et al. (Nov. 2012) "Hypomethylation of the IL17RC Promoter Associates with Age-Related Macular Degeneration" *Cell Reports* 2(5):1151-1158.
Wright et al. (Aug. 2008) "The human IL-17F/IL-17A heterodimeric cytokine signals through the IL-17RA/ IL-17RC receptor complex" *The Journal of Immunolog* 181(4):2799-2805.
Wu et al. (2001) "Gene Therapy for the Management of Pain," *Anesthes.* 94:1119-1132.
Xiao et al. (1997) "Gene Transfer by Adeno-Associated Virus Vectors into the Central Nervous System," *Exp. Neurobiol.*, 144:113-124.
Xu et al. (2001) "CMV-β-Actin Promoter Directs Higher Expression from an Adeno-Associated Viral Vector in the Liver than the Cytomegalovirus or Elongation Factor 1α Promoter and Results in Therapeutic Levels of Human Factor X in Mice," *Hum Gene Ther* 12:563-573.
Zhou et al. (1994) "Adeno-Associated Virus 2-Mediated High Efficiency Gene Transfer into Immature and Mature Subsets of Hematopoietic Progenitor Cells in Human Umbilical Cord Blood," *J. Exp. Med.* 179:1867-1875.
Ziegler et al. (2004) "AAV2 Vector Harboring a Liver-Restricted Promoter Facilitates Sustained Expression of Therapeutic Levels of α-Galactosidase A and the Induction of Immune Tolerance in Fabry Mice," *Mol Ther* 9:231-240.
Zolotukhin et al. (2002) "Production and Purification of Serotype 1, 2 and 5 Recombinant Adeno-Associated Viral Vectors," *Methods* 28:158-167.
Zuniga et al, (2010) "IL-17 Regulates Adipogenesis, Glucose Homeostasis, and Obesity," *J Immunol* 185:6947-6959.

\* cited by examiner

SEQ ID NO:1

```
   1     atggggg   ccgcacgcag  cccgccgtcc  gctgtccgg   ggcccctgct
  48     ggggctgctc ctgctgctcc tgggcgtgct  ggccccgggt  ggcgcctccc tgcgactcct
 108     ggaccaccgg gcgctggtct gctcccagcc  ggggctaaac  tgcacggtca  agaatagtac
 168     ctgcctggat gacagctgga ttcaccctcg  aaacctgacc  ccctcctccc  caaaggacct
 228     gcagatccag ctgcactttg cccacaccca  acaaggagac  ctgttccccg  tggctcacat
 288     cgaatggaca ctgcagacag acgccagcat  cctgtacctc  gagggtgcag  agttatctgt
 348     cctgcagctg aacaccaatg aacgtttgtg  cgtcaggttt  gagtttctgt  ccaaactgag
 408     gcatcaccac aggcggtggc gttttacctt  cagccacttt  gtggttgacc  ctgaccagga
 468     atatgaggtg accgttcacc acctgcccaa  gcccatccct  gatggggacc  caaaccacca
 528     gtccaagaat tccttgtgc  ctgactgtga  gcacgccagg  atgaaggtaa  ccacgccatg
 588     catgagctca ggcagcctgt gggaccccaa  catcaccgtg  gagaccctgg  aggcccacca
 648     gctgcgtgtg agcttcaccc tgtggaacga  atctacccat  taccagatcc  tgctgaccag
 708     ttttccgcac atggagaacc acagttgctt  tgagcacatg  caccacatac  ctgcgcccag
 768     accagaagag ttccaccagc gatccaacgt  cacactcact  ctacgcaacc  ttaaagggtg
 828     ctgtcgccac caagtgcaga tccagccctt  cttcagcagc  tgcctcaatg  actgcctcag
 888     acactccgcg actgtttcct gcccagaaat  gccagacact  ccagaaccaa  ttccggacta
 948     catgccctg  tgggtgtact ggttcatcac  gggcatctcc  atcctgctgg  tgggctccgt
1008     catcctgctc atcgtctgca tgacctggag  gctagctggg  cctggaagtg  aaaaatacag
1068     tgatgacacc aaatacaccg atggcctgcc  tgcggctgac  ctgatccccc  accgctgaa
1128     gcccaggaag gtctggatca tctactcagc  cgaccacccc  ctctacgtgg  acgtggtcct
1188     gaaattcgcc cagttcctgc tcaccgcctg  cggcacggaa  gtggccctgg  acctgctgga
1248     agagcaggcc atctcggagg caggagtcat  gacctgggtg  ggccgtcaga  agcaggagat
1308     ggtggagagc aactctaaga tcatcgtcct  gtgctcccgc  ggcacgcgcg  ccaagtggca
1368     ggcgctcctg ggccgggggg cgcctgtgcg  gctgcgctgc  gaccacggaa  agcccgtggg
1428     ggacctgttc actgcagcca tgaacatgat  cctcccggac  ttcaagaggc  agcctgctt
1488     cggcacctac gtagtctgct acttcagcga  ggtcagctgt  gacggcgacg  tccccgacct
1548     gttcggcgcg cgccgcggt  acccgctcat  ggacaggttc  gaggaggtgt  acttccgcat
1608     ccaggacctg gagatgttcc agccgggccg  catgcaccgc  gtaggggagc  tgtcggggga
1668     caactacctg cggagcccgg gcggcaggca  gctccgcgcc  gccctggaca  ggttccggga
1728     ctggcaggtc cgctgtcccg actggttcga  atgtgagaac  ctctactcag  cagatgacca
1788     ggatgccccg tccctggacg aagaggtgtt  tgaggagcca  ctgctgcctc  cgggaaccgg
1848     catcgtgaag cgggcgcccc tggtgcgcga  gcctggctcc  aggcctgcc   tggccataga
1908     cccgctggtc ggggaggaag gaggagcagc  agtggcaaag  ctggaacctc  acctgcagcc
1968     ccggggtcag ccagcgccgc agcccctcca  caccctggtg  ctcgccgcag  aggaggggc
2028     cctggtggcc gcggtggagc ctgggcccct  ggctgacggt  gccgcagtcc  ggctggcact
2088     ggcgggggag ggcgaggcct gcccgctgct  gggcagcccg  ggcgctgggc  gaaatagcgt
2148     cctcttcctc cccgtggacc ccgaggactc  gccccttggc  agcagcaccc  ccatggcgtc
2208     tcctgacctc cttccagagg acgtgaggga  gcacctcgaa  ggcttgatgc  tctcgctctt
2268     cgagcagagt ctgagctgcc aggcccaggg  gggctgcagt  agacccgcca  tggtcctcac
2328     agacccacac acgccctacg aggaggagca  gcggcagtca  gtgcagtctg  accagggcta
2388     catctccagg agctccccgc agccccccga  gggactcacg  gaaatggagg  aagaggagga
2448     agaggagcag gacccaggga agccggccct  gccactctct  cccgaggacc  tggagagcct
2508     gaggagcctc cagcggcagc tgcttttccg  ccagctgcag  aagaactcgg  gctgggacac
2568     gatggggtca gagtcagagg ggcccagtgc  atga
```

Figure 1A

SEQ ID NO:2

```
  1    MGAARSPPSAVPGPLLGLLLLLLGVLAPGGASLRLLDHRALVCSQPGLNC
 51    TVKNSTCLDDSWIHPRNLTPSSPKDLQIQLHFAHTQQGDLFPVAHIEWTL
101    QTDASILYLEGAELSVLQLNTNERLCVRFEFLSKLRHHHRRWRFTFSHFV
151    VDPDQEYEVTVHHLPKPIPDGDPNHQSKNFLVPDCEHARMKVTTPCMSSG
201    SLWDPNITVETLEAHQLRVSFTLWNESTHYQILLTSFPHMENHSCFEHMH
251    HIPAPRPEEFHQRSNVTLTLRNLKGCCRHQVQIQPFFSSCLNDCLRHSAT
301    VSCPEMPDTPEPIPDYMPLWVYWFITGISILLVGSVILLIVCMTWRLAGP
351    GSEKYSDDTKYTDGLPAADLIPPPLKPRKVWIIYSADHPLYVDVVLKFAQ
401    FLLTACGTEVALDLLEEQAISEAGVMTWVGRQKQEMVESNSKIIVLCSRG
451    TRAKWQALLGRGAPVRLRCDHGKPVGDLFTAAMNMILPDFKRPACFGTYV
501    VCYFSEVSCDGDVPDLFGAAPRYPLMDRFEEVYFRIQDLEMFQPGRMHRV
551    GELSGDNYLRSPGGRQLRAALDRFRDWQVRCPDWFECENLYSADDQDAPS
601    LDEEVFEEPLLPPGTGIVKRAPLVREPGSQACLAIDPLVGEEGGAAVAKL
651    EPHLQPRGQPAPQPLHTLVLAAEEGALVAAVEPGPLADGAAVRLALAGEG
701    EACPLLGSPGAGRNSVLFLPVDPEDSPLGSSTPMASPDLLPEDVREHLEG
751    LMLSLFEQSLSCQAQGGCSRPAMVLTDPHTPYEEEQRQSVQSDQGYISRS
801    SPQPPEGLTEMEEEEEEQDPGKPALPLSPEDLESLRSLQRQLLFRQLQK
851    NSGWDTMGSESEGPSA
```

Figure 1B

SEQ ID NO:3

```
1     ATGGGGGCCGCACGCAGCCCGCCGTCCGCTGTCCCGGGGCCCCTGCTGGGGCTGCTCCTG
61    CTGCTCCTGGGCGTGCTGGCCCCGGGTGGCGCCTCCCTGCGACTCCTGGACCACCGGGCG
121   CTGGTCTGCTCCCAGCCGGGGCTAAACTGCACGGTCAAGAATAGTACCTGCCTGGATGAC
181   AGCTGGATTCACCCTCGAAACCTGACCCCCTCCTCCCAAAGGACCTGCAGATCCAGCTG
241   CACTTTGCCCACACCCAACAAGGAGACCTGTTCCCCGTGGCTCACATCGAATGGACACTG
301   CAGACAGACGCCAGCATCCTGTACCTCGAGGGTGCAGAGTTATCTGTCCTGCAGCTGAAC
361   ACCAATGAACGTTTGTGCGTCAGGTTTGAGTTTCTGTCCAAACTGAGGCATCACCACAGG
421   CGGTGGCGTTTTACCTTCAGCCACTTTGTGGTTGACCCTGACCAGGAATATGAGGTGACC
481   GTTCACCACCTGCCCAAGCCCATCCCTGATGGGGACCCAAACCACCAGTCCAAGAATTTC
541   CTTGTGCCTGACTGTGAGCACGCCAGGATGAAGGTAACCACGCCATGCATGAGCTCAGGC
601   AGCCTGTGGGACCCCAACATCACCGTGGAGACCCTGGAGGCCCACCAGCTGCGTGTGAGC
661   TTCACCCTGTGGAACGAATCTACCCATTACCAGATCCTGCTGACCAGTTTTCCGCACATG
721   GAGAACCACAGTTGCTTTGAGCACATGCACCACATACCTGCGCCCAGACCAGAAGAGTTC
781   CACCAGCGATCCAACGTCACACTCACTCTACGCAACCTTAAAGGGTGCTGTCGCCACCAA
841   GTGCAGATCCAGCCCTTCTTCAGCAGCTGCCTCAATGACTGCCTCAGACACTCCGCGACT
901   GTTTCCTGCCCAGAAATGCCAGACACTCCAGAACCAATTCCGGACTACATGACCGGTGGA
961   GGTGGAGGTGGAGGTGGAGGTCAGCCCCGAGAACCACAGGTGTACACCCTGCCCCCATCC
1021  CGGGATGAGCTGACCAAGAACCAGGTCAGCCTGACCTGCCTGGTCAAAGGCTTCTATCCC
1081  AGCGACATCGCCGTGGAGTGGGAGAGCAATGGGCAGCCGGAGAACAACTACAAGACCACG
1141  CCTCCCGTGCTGGACTCCGACGGCTCCTTCTTCCTCTACAGCAAGCTCACCGTGGACAAG
1201  AGCAGGTGGCAGCAGGGGAACGTCTTCTCATGCTCCGTGATGCATGAGGCTCTGCACAAC
1261  CACTACACGCAGAAGAGCCTCTCCCTGTCTCCGGGTAAATAG
```

Figure 3A

SEQ ID NO:4

```
1     MGAARSPPSAVPGPLLGLLLLLLGVLAPGGASLRLLDHRALVCSQPGLNC
51    TVKNSTCLDDSWIHPRNLTPSSPKDLQIQLHFAHTQQGDLFPVAHIEWTL
101   QTDASILYLEGAELSVLQLNTNERLCVRFEFLSKLRHHHRRWRFTFSHFV
151   VDPDQEYEVTVHHLPKPIPDGDPNHQSKNFLVPDCEHARMKVTTPCMSSG
201   SLWDPNITVETLEAHQLRVSFTLWNESTHYQILLTSFPHMENHSCFEHMH
251   HIPAPRPEEFHQRSNVTLTLRNLKGCCRHQVQIQPFFSSCLNDCLRHSAT
301   VSCPEMPDTPEPIPDYMTGGGGGGGGQPREPQVYTLPPSRDELTKNQVS
351   LTCLVKGFYPSDIAVEWESNGQPENNYKTTPPVLDSDGSFFLYSKLTVDK
401   SRWQQGNVFSCSVMHEALHNHYTQKSLSLSPGK
```

Figure 3B

COMPOSITIONS AND METHODS FOR TREATING AND PREVENTING MACULAR DEGENERATION

CROSS-REFERENCE TO RELATED APPLICATIONS

This application is a National Phase application under 35 U.S.C. § 371 of International Application No. PCT/US2014/034538 filed Apr. 17, 2014, which claims the benefit of U.S. Provisional Patent Application No. 61/813,014, filed Apr. 17, 2013, the disclosures of which are herein incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 159792013600SeqList.txt, date recorded: Oct. 14, 2015, size: 18 KB).

TECHNICAL FIELD

The present invention relates generally to methods for treating and preventing macular degeneration. In particular, the present invention pertains to methods for treating or preventing age related macular degeneration using inhibitors of interleukin-17.

SUMMARY OF THE INVENTION

Age-related macular degeneration (AMD) is the primary cause of central irreversible blindness in the elderly. Early clinical presentation of AMD involves subretinal accumulation of debris (drusen). Patients who progress develop either geographic atrophy (GA), with significant degeneration and atrophy of the macular cells, or neovascular AMD (nAMD), with choroidal neovascularization occurring in the end stage of the disease process in an attempt to save the degenerating retina. Blindness results when photoreceptors atrophy following macular retinal pigment epithelial (RPE) degeneration (Curcio et al., *Invest Ophthalmol. Vis. Sci.* (1996) 37:1236-1249.

Pathogenesis is contingent on aging, environmental and genetic risk factors but the molecular mechanism responsible for disease onset remains largely unknown. The most prominent known genetic factor is a missense mutation residing within the immunoregulatory complement factor H (CFH) gene (Edwards et al., *Science* (2005) 308:421-424. Subsequent to this finding, many studies have identified active complement proteins associated with disease. Significantly, complement component C5a serum levels are elevated in both AMD patient serum (Hecker et al., *Hum Mol Genet* (2010) 19:209-215; Reynolds et al., *Invest Ophthalmol Vis Sci* (2009) 50:5818-5827; Scholl et al., *PLoS One* (2008) 3:e2593) and in AMD drusen (Nozaki et al, *Proc. Natl. Acad. Sci. U.S.A* (2006) 103:2328-2333. C5a stimulates interleukin-17A (IL17A) production in human $CD4^+$ T lymphocytes (Liu et al., *J Transl Med* (2011) 9:111) and the IL17A cytokine is known to drive chronic inflammation, as well as autoimmune and neurodegenerative diseases including multiple sclerosis and Alzheimer's disease (Hu et al., *Neurology* (2010) 75:2079-2086). Consequently, these data link observations of increased serum levels of IL17A protein in AMD patients with enhanced complement expression in drusen (Liu et al., *J Transl Med* (2011) 9:111). Furthermore, a report that differential hypomethylation of the IL17 receptor C (IL17RC) gene in twins and siblings with discordant disease, as well as in the population at-large, points to the IL17A pathway as a key player in the disease (Wei et al., *Cell Reports* (2012) 2:1151-1158). Despite the presence of IL17A in AMD patient sera, it is not known whether this is related to retinal degeneration.

The present invention is based on the surprising discovery that IL17 inhibitors can be used to treat macular degeneration. IL17A, a pro-inflammatory cytokine, plays a critical role in focal retinal degeneration. IL17A and IL17RC transcripts and protein are significantly elevated in AMD patient maculae compared to age-matched controls, and treatment of the ARPE-19 cell line with recombinant IL17A reduces cell viability, causes accumulation of cytoplasmic lipids, and induces cellular apoptosis.

$Ccl2^{-/-}/Cx3cr1^{-/-}/Crb1^{rd8}$ (DKO/rd8) mice are a model of progressive, focal retinal degeneration (Chan et al., *Ophthalmic Res* (2000) 40:124-128; Tuo et al., *Invest Ophthalmol Vis Sci* (2007) 48:3827-3836). DKO/rd8 mice develop two distinct lesion types: (1) "AMD-like," featuring degeneration of RPE and of photoreceptor inner and outer segments (IS, OS) and (2) "dystrophic," rd8-associated lesions affecting inner and outer nuclear layer (INL and ONL) neurons. DKO/rd8 pathology features dysregulation of the complement system and retinal microglia (Ross et al., *Exp. Eye Res.* (2008) 86:675-683; Shen et al., *Invest Ophthalmol Vis Sci* (2011) 52:2897-2904), key immunological components of AMD pathology. Surprisingly, the inventors herein have demonstrated that reducing or inhibiting IL17 activity is effective in treating DKO/rd8 mice. Neutralization of IL17 by intravitreal injection of an adeno-associated virus vector encoding a soluble IL17 receptor significantly ameliorated photoreceptor and RPE degeneration. Retinal degeneration was found to be MAPK-dependent, as IL17 inhibition prevented Erk1/2 and p38 phosphorylation. Thus, IL17 was shown to play a key role in photoreceptor and RPE degeneration and neutralization thereof can be used to treat macular degeneration.

Thus in aspects, the invention is directed to methods for treating macular degeneration in a mammalian subject. In embodiments, the method involves administering to the diseased eye of the subject a composition containing a recombinant vector encoding an IL17 inhibitor. In embodiments, the method involves administering to the diseased eye of the subject a composition containing a recombinant adeno-associated virus comprising a nucleic acid encoding an IL17 inhibitor.

In aspects, the invention is directed to methods for treating or reducing retinal degeneration (e.g., focal retinal degeneration) or in a mammalian subject. In embodiments, the method involves administering to the diseased eye of the subject a composition containing a recombinant vector encoding an IL17 inhibitor. In embodiments, the method involves administering to the diseased eye of the subject a composition containing a recombinant adeno-associated virus comprising a nucleic acid encoding an IL17 inhibitor. In embodiments, the subject has macular degeneration.

In aspects, the invention is directed to methods for treating or reducing retinal pigment epithelium (RPE) degeneration, RPE stress, or RPE damage in a mammalian subject. In embodiments, the method involves administering to the diseased eye of the subject a composition containing a recombinant vector encoding an IL17 inhibitor. In embodiments, the method involves administering to the diseased eye of the subject a composition containing a recombinant adeno-associated virus comprising a nucleic acid encoding an IL17 inhibitor. In embodiments, the subject has macular degeneration.

In aspects, the invention is directed to methods for treating or reducing photoreceptor degeneration in a mammalian subject. In embodiments, the method involves administering to the diseased eye of the subject a composition containing a recombinant vector encoding an IL17 inhibitor. In embodiments, the method involves administering to the diseased eye of the subject a composition containing a recombinant adeno-associated virus comprising a nucleic acid encoding an IL17 inhibitor. In embodiments, the photoreceptor degeneration is in the inner segment (IS) of the photoreceptor. In embodiments, the photoreceptor degeneration is in the outer segment (IOS) of the photoreceptor. In embodiments, the photoreceptor degeneration is in the inner and outer segment (IS/OS) of the photoreceptor. In embodiments, the subject has macular degeneration.

In aspects, the invention is directed to methods for reducing lipofuscin or glycogen deposits in a diseased eye of a mammalian subject. In embodiments, the method involves administering to the diseased eye of the subject a composition containing a recombinant vector encoding an IL17 inhibitor. In embodiments, the method involves administering to the diseased eye of the subject a composition containing a recombinant adeno-associated virus comprising a nucleic acid encoding an IL17 inhibitor. In embodiments, the subject has macular degeneration.

In aspects, the invention is directed to methods for reducing 2,6-dimethyl-8-(2,6,6-trimethyl-1-cyclohexen-1-yl)-1E, 3E,5E,7E-octatetra-enyl]-1-(2-hydroxyethyl)-4-[4-methyl-6 (2,6,6-trimethyl-1-cyclohexen-1-yl) 1E,3E,5E,7E-hexatrienyl]-pyridinium (A2E) in a diseased eye of a mammalian subject. In embodiments, the method involves administering to the diseased eye of the subject a composition containing a recombinant vector encoding an IL17 inhibitor. In embodiments, the method involves administering to the diseased eye of the subject a composition containing a recombinant adeno-associated virus comprising a nucleic acid encoding an IL17 inhibitor. In embodiments, the subject has macular degeneration.

In aspects, the invention is directed to methods for reducing mitochondrial damage in a diseased eye of a mammalian subject. In embodiments, the method involves administering to the diseased eye of the subject a composition containing a recombinant vector encoding an IL17 inhibitor. In embodiments, the method involves administering to the diseased eye of the subject a composition containing a recombinant adeno-associated virus comprising a nucleic acid encoding an IL17 inhibitor. In embodiments, the subject has macular degeneration.

In any of the above aspects and embodiments, the method can involve administering to the diseased eye of the subject a composition containing a recombinant adeno-associate virus (rAAV) virion having a nucleic acid encoding an IL17 inhibitor (i.e., the recombinant vector is in a rAAV virion).

In any of the above aspects and embodiments, the composition can further contain an opthalmalogically acceptable vehicle.

In any of the above aspects and embodiments, the composition is administered in a therapeutically effective amount.

In any of the above aspects and embodiments, the IL17 inhibitor can be an IL17 receptor capable of binding and modulating the activity of IL17.

In any of the above aspects and embodiments, the IL17 inhibitor can be an IL17A inhibitor (e.g., an IL17A receptor).

In some embodiments, the IL17 receptor (e.g., IL17A receptor) is a soluble receptor.

In any of the above aspects and embodiments, the IL17 inhibitor can be a fusion protein comprising the IL17 receptor and a multimerization domain. In embodiments, the multimerization domain is derived from an immunoglobulin (Ig) (e.g., Ig heavy chain; Ig constant region; Fc region of an Ig; CH3 of an Ig; and the like). In embodiments, the multimerization domain is derived from an IgG1, an IgG2, an IgG3 or an IgG4. In some embodiments, the multimerization domain is from the constant region of an IgG1 heavy chain.

In embodiments, when the fusion protein is expressed, a multimer of the fusion protein is produced. In some embodiments, the multimer is a homodimer.

In certain embodiments, the IL17 inhibitor is an IL17A inhibitor, such as an IL17A receptor capable of binding and modulating the activity of IL17A.

In some embodiments, the vector/nucleic acid encodes a fusion protein comprising:
(a) the IL17A receptor; and
(b) an immunoglobulin constant region multimerization domain,
wherein when the fusion protein is expressed, a multimer of the fusion protein is produced.

In further embodiments, the multimer is a homodimer.
In additional embodiments, the multimerization domain comprises the CH3 domain of an IgG, or an active fragment thereof, such as the multimerization domain from an IgG1, an IgG2, an IgG3 or an IgG4.

In yet additional embodiments, the multimerization domain is from the constant region of an IgG1 heavy chain.

In further embodiments of the methods above, the IL17 receptor is a soluble IL17 receptor.

In additional embodiments, the fusion protein comprises the amino acid sequence of FIG. 3B (SEQ ID NO:4), or an active variant thereof having at least 85%, 90%, 91%, 92%, 93%, 94%, 95%, 96%, 97%, 98%, or 99% sequence identity to the sequence of FIG. 3B (SEQ ID NO:4).

In any of the above aspects and embodiments, the recombinant vector can be in a recombinant virus, such as a recombinant adeno-associated virus virion or a recombinant adenovirus.

In any of the above aspects and embodiments, the macular degeneration is age-related macular degeneration (AMD), such as dry AMD.

In any of the above aspects and embodiments, the composition can be administered intravitreally.

In aspects, the invention is directed to the use of a recombinant vector comprising a polynucleotide encoding an IL17 inhibitor in the manufacture of a medicament for treating macular degeneration. In certain embodiments, the polynucleotide encodes a fusion protein comprising:
(a) the IL17A receptor; and
(b) an immunoglobulin constant region multimerization domain,
wherein when the fusion protein is expressed, a multimer of the fusion protein is produced.

In some embodiments, the IL17 receptor is a soluble IL17 receptor.

In further embodiments, the fusion protein comprises the amino acid sequence of FIG. 3B (SEQ ID NO:4), or an active variant thereof having at least 85%, 90%, 91%, 92%, 93%, 94%, 95%, 96%, 97%, 98%, or 99% sequence identity to the sequence of FIG. 3B (SEQ ID NO:4).

In aspects, the invention is directed to compositions for treating or reducing macular degeneration, RPE degeneration, RPE stress, RPE damage, photoreceptor degeneration, lipofuscin or glycogen deposits in a diseased eye, A2E in a diseased eye, or mitochondrial damage comprising the composition of a recombinant vector encoding an IL17 inhibitor (e.g., for use in any one of the methods described herein).

In aspects, the invention is directed to compositions for treating or reducing macular degeneration, RPE degeneration, RPE stress, RPE damage, photoreceptor degeneration, lipofuscin or glycogen deposits in a diseased eye, A2E in a diseased eye, or mitochondrial damage comprising a recombinant adeno-associated virus (rAAV) virion comprising nucleic acid encoding an IL17 inhibitor (e.g., for use in any one of the methods described herein).

In any of the above aspects and embodiments, the composition contains a therapeutically effective amount of the recombinant vector or the rAAV virion.

In aspects, the invention is directed to recombinant vectors encoding an IL17 inhibitor for use in any one of the methods described herein.

In aspects, the invention is directed to rAAV virions containing a nucleic acid encoding an IL17 inhibitor for use to treat or reduce macular degeneration, RPE degeneration, RPE stress, RPE damage, photoreceptor degeneration, lipofuscin or glycogen deposits in a diseased eye, A2E in a diseased eye, or mitochondrial damage (e.g., in accordance with any one of the methods described herein).

In aspects, the invention is directed to kits containing any one of the compositions described herein.

In aspects, the invention is directed to kits containing any one of the recombinant vectors described herein.

In aspects, the invention is directed to kits containing any one of the rAAV virions described herein.

In the above aspects, the kits can further contain instructions for use of the composition, recombinant vector, or rAAV virion in the treatment or reduction of macular degeneration, RPE degeneration, RPE stress, RPE damage, photoreceptor degeneration, lipofuscin or glycogen deposits in a diseased eye, A2E in a diseased eye, or mitochondrial damage (e.g., in accordance with any one of the methods described herein).

In any of the above aspects and embodiments, the kits contain a therapeutically effective amount of the composition, recombinant vector, or the rAAV virion.

In aspects, the invention is directed to articles of manufacture containing any one of the compositions described herein.

In aspects, the invention is directed to articles of manufacture containing any one of the recombinant vectors described herein.

In aspects, the invention is directed to articles of manufacture containing any one of the rAAV virions described herein.

In any of the above aspects and embodiments, the rAAV virion can contain an AAV1, AAV2, AAV3, AAV4, AAV5, AAV6, AAV7, AAV8, AAVrh8, AAVrh8R, AAV9, AAV10, AAVrh10, AAV11, or AAV12 serotype capsid. In related embodiments, the rAAV virion contains a recombinant vector having an AAV1, AAV2, AAV3, AAV4, AAV5, AAV6, AAV7, AAV8, AAVrh8, AAVrh8R, AAV9, AAV10, AAVrh10, AAV11, or AAV12 ITR.

In some embodiments, the rAAV virion contains an AAV2 serotype capsid, and optionally, the virion contains a recombinant vector having an AAV2 ITR.

These and other embodiments of the subject invention will readily occur to those of skill in the art in view of the disclosure herein.

BRIEF DESCRIPTION OF THE FIGURES

FIGS. 1A-1B (SEQ ID NOS:1 and 2) show the full-length nucleotide sequence (FIG. 1A) and corresponding amino acid sequence (FIG. 1B) of a representative human IL17rA.

FIGS. 3A and 3B (SEQ ID NOS:3 and 4) show the nucleotide sequence and corresponding amino acid sequence of the sIL17RA-9gly-CH3 construct depicted in FIG. 2.

FIG. 6A shows qRT-PCR quantification of IL17A expression in the macular choroidal button. FIG. 6B shows IL17A expression in the macula. FIG. 6C shows IL17RC expression in the macula. FIG. 6D shows immunohistochemical detection of IL17A and IL17RC protein in macular sections. Isotype controls were stained only with secondary antibody. GA=geographic atrophy; nAMD=neovascular AMD; Total=GA+nAMD; GCL=ganglion cell layer; IPL=inner plexiform layer; INL=inner nuclear layer; OPL=outer plexiform layer; ONL=outer nuclear layer; IS/OS=inner/outer segment; RPE=retinal pigment epithelium. *: $P<0.05$; : $P<0.005$; *: $P<0.0005$

FIG. 9A shows results of an MTT assay on kidney COS-7 cells treated for 48 h with dilutions of IL17A. FIG. 9B shows the relative expression of IL17RA and IL17RC between ARPE-19 and COS-7, evaluated by qRT-PCR.

FIG. 10A shows qRT-PCR quantification of retinal Il17a transcripts as a function of age in a combination of C57BL6N and C57BL/6J mice versus DKO/rd8. FIG. 10B shows fundoscopic results of sIL17R- versus EV-receiving retinas. FIG. 10C shows a paired comparison of A2E concentration in sIL17R and EV eyes from the same mice. FIG. 10D shows representative histopathological findings in sIL17R-vs-EV retinas. sIL17R preserved photoreceptor IS/OS compared to EV (asterisks) and maintained thickness of the ONL. EV retinas additionally showed RPE degeneration. FIG. 10E shows that abundant lipofuscin was observed in EV but not in sIL17R RPE (upper left and right). Mitochondria (m) were unhealthy and chaotically dispersed within EV RPE (lower left) but were healthy and linearly arranged in sIL17R RPE (lower right). EV RPE showed extensive vacuolization, undigested OS and poor basal infoldings (lower left). FIG. 10F shows MAPK-dependent retinal degeneration by Western blot. EV and sIL17R neuroretinas were treated with 50 ng/ml Il17a for 2 h ex vivo prior to protein isolation. *: $P<0.05$; : $P<0.005$; **: $P<0.00001$.

FIG. 12A shows ELISA detection of sIL17R protein. FIG. 12B shows qRT-PCR measurement of retinal Il17a and FIG. 12C shows Il16 mRNA *: P<0.05; n.s.=not significant.

FIG. 14A depicts the results of qRT-PCR and FIG. 14B shows an end-stage gel.

DETAILED DESCRIPTION OF THE INVENTION

Figure 2:
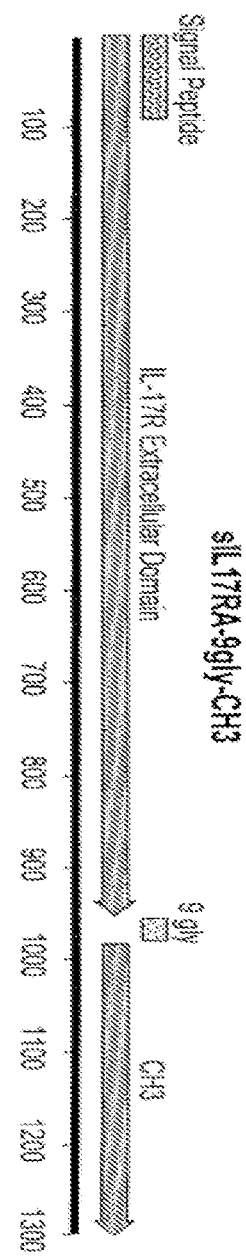
FIG. 2 is a diagrammatic representation of a fusion construct including a soluble IL17rA linked to the CH3 domain of the Fc region of a human IgG1 immunoglobulin via a linker of nine Gly residues (sIL17R-9gly-CH3).

The practice of the present invention will employ, unless otherwise indicated, conventional methods of chemistry, biochemistry, recombinant DNA techniques and immunology, within the skill of the art. Such techniques are explained fully in the literature. See, e.g., *Fundamental Virology*, 2nd Edition, vol. I & II (B. N. Fields and D. M. Knipe, eds.); *Handbook of Experimental Immunology*, Vols. I-IV (D. M. Weir and C. C. Blackwell eds., Blackwell Scientific Publications); T. E. Creighton, *Proteins: Structures and Molecular Properties* (W.H. Freeman and Company, 1993); A. L. Lehninger, *Biochemistry* (Worth Publishers, Inc., current addition); *Methods In Enzymology* (S. Colowick and N. Kaplan eds., Academic Press, Inc.); *Molecular Cloning: A Laboratory Manual* (Sambrook et al., 4$^{th}$ ed., Cold Spring Harbor Laboratory Press, Cold Spring Harbor, N.Y., 2012); *Current Protocols in Molecular Biology* (F. M. Ausubel, et al. eds., 2003); the series *Methods in Enzymology* (Academic Press, Inc.); *PCR 2: A Practical Approach* (M. J. MacPherson, B. D. Hames and G. R. Taylor eds., 1995); *Antibodies, A Laboratory Manual* (Harlow and Lane, eds., 1988); *Culture of Animal Cells: A Manual of Basic Technique and Specialized Applications* (R. I. Freshney, 6$^{th}$ ed., J. Wiley and Sons, 2010); *Oligonucleotide Synthesis* (M. J. Gait, ed., 1984); *Methods in Molecular Biology*, Humana Press; *Cell Biology: A Laboratory Notebook* (J. E. Cellis, ed., Academic Press, 1998); *Introduction to Cell and Tissue Culture* (J. P. Mather and P. E. Roberts, Plenum Press, 1998); *Cell and Tissue Culture: Laboratory Procedures* (A. Doyle, J. B. Griffiths, and D. G. Newell, eds., J. Wiley and Sons, 1993-8); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Ausubel et al., eds., J. Wiley and Sons, 2002); *Immunobiology* (C. A. Janeway et al., 2004); *Antibodies* (P. Finch, 1997); *Antibodies: A Practical Approach* (D. Catty, ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane, Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 2011).

All publications, patents and patent applications cited herein, whether supra or infra, are hereby incorporated by reference in their entirety.

1. Definitions

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "an interleukin receptor" includes a mixture of two or more such receptors, and the like.

As used herein, "age-related macular degeneration" or "AMD" includes early, intermediate, and advanced AMD and includes both dry AMD such as geographic atrophy and wet AMD, also known as neovascular or exudative AMD.

The term "interleukin-17 receptor" (IL17r) or a nucleotide sequence encoding the same, refers to a protein or nucleotide sequence, respectively, that is derived from any IL17 receptor regardless of source. The term, as used herein, refers to molecules capable of binding to and modulating activity of the corresponding ligand, as measured in any of the known IL17 activity tests, including those described further herein, such as by reducing or inhibiting the production of IL17. The full-length nucleotide sequence and corresponding amino acid sequence of a representative human IL17rA is shown in FIGS. 1A-1B (SEQ ID NOS:1 and 2). However, an interleukin receptor as defined herein is not limited to the depicted sequence as several such receptors are known and variations in these receptors will occur between species.

The full-length proteins, with or without the signal sequence, and fragments thereof, as well as proteins with modifications, such as deletions, additions and substitutions (either conservative or non-conservative in nature), to the native sequence, are intended for use herein, so long as the protein maintains the desired activity. Such active variants and fragments are considered IL17 receptors in the context of the present invention. Modifications may be deliberate, as through site-directed mutagenesis, or may be accidental, such as through mutations of hosts which produce the proteins or errors due to PCR amplification. Accordingly, active proteins substantially homologous to the parent sequence, e.g., proteins with 70 . . . 80 . . . 85 . . . 90 . . . 95 . . . 98 . . . 99% etc. identity that retain the ability to modulate activity of the corresponding ligand, are contemplated for use herein.

A "native" polypeptide, such as an interleukin receptor sequence, refers to a polypeptide having the same amino acid sequence as the corresponding molecule derived from nature. Such native sequences can be isolated from nature or can be produced by recombinant or synthetic means. The term "native" sequence specifically encompasses naturally-occurring truncated or secreted forms of the specific molecule (e.g., an extracellular domain sequence), naturally-occurring variant forms (e.g., alternatively spliced forms) and naturally-occurring allelic variants of the polypeptide. In various embodiments of the invention, the native molecules disclosed herein are mature or full-length native sequences comprising the full-length amino acids sequences shown in the accompanying figures. However, while some of the molecules disclosed in the accompanying figures begin with methionine residues designated as amino acid position 1 in the figures, other methionine residues located either upstream or downstream from amino acid position 1 in the figures may be employed as the starting amino acid residue for the particular molecule. Alternatively, depending on the expression system used, the molecules described herein may lack an N-terminal methionine.

By "extracellular domain" is meant a form of the receptor polypeptide which includes all or a fragment of the extracellular domain and lacks all or a portion of the transmembrane domain and may also be devoid of the cytoplasmic domain. Typically, when used in the present invention, the extracellular domain is essentially free of both the transmembrane and cytoplasmic domains. In embodiments, an extracellular domain includes less than 10% of such transmembrane and/or cytoplasmic domains, less than 5% of these domains, less than 1%, or less than 0.5% of such domains. Transmembrane domains for the receptors described herein can be identified pursuant to criteria routinely employed in the art for identifying hydrophobic domains, for example, using standard hydropathy plots, such as those calculated using the Kyte-Doolittle technique, Kyte et al., *J. Mol. Biol.* (1982) 157:105-132.

As explained above, the interleukin receptors for use with the present invention may or may not include the native signal sequence. The approximate location of the signal peptides of the interleukin receptors described herein are described in the specification and in the accompanying figures. It is noted, however, that the C-terminal boundary of a signal peptide may vary, typically by no more than about 5 amino acids on either side of the signal peptide C-terminal boundary as described herein. The C-terminal boundary of the signal peptide may be identified pursuant to criteria routinely employed in the art, such as described in Nielsen et al., *Prot. Eng.* (1997) 10:1-6 and von Heinje et al., *Nucl. Acids. Res.* (1986) 14:4683-4690. Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

By "variant" is meant an active polypeptide as defined herein having at least about 80% amino acid sequence identity with the corresponding full-length native sequence, a polypeptide lacking the signal peptide, an extracellular domain of a polypeptide, with or without a signal peptide, or any other fragment of a full-length polypeptide sequence as disclosed herein. Such polypeptide variants include, for instance, polypeptides wherein one or more amino acid residues are added, or deleted, at the N- and/or C-terminus of the full-length native amino acid sequence. In embodiments, a variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to the corresponding full-length native sequence. In embodiments, variant polypeptides are at least about 10 amino acids in length, such as at least about 20 amino acids i+n length, e.g., at least about 30 amino acids in length, alternatively at least about 40 amino acids in length, alternatively at least about 50 amino acids in length, alternatively at least about 60 amino acids in length, alternatively at least about 70 amino acids in length, alternatively at least about 80 amino acids in length, alternatively at least about 90 amino acids in length, alternatively at least about 100 amino acids in length, alternatively at least about 150 amino acids in length, alternatively at least about 200 amino acids in length, alternatively at least about 300 amino acids in length, or more. Variants include substitutions that are conservative or non-conservative in nature. For example, the polypeptide of interest may include up to about 5-10 conservative or non-conservative amino acid substitutions, or even up to about 15-25 or 50 conservative or non-conservative amino acid substitutions, or any number between 5-50, so long as the desired function of the molecule remains intact.

"Homology" refers to the percent identity between two polynucleotide or two polypeptide moieties. Two DNA, or two polypeptide sequences are "substantially homologous" to each other when the sequences exhibit at least about 50%, at least about 75%, at least about 80%-85%, at least about 90%, at least about 95%-98% sequence identity, at least about 99%, or any percent therebetween over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Methods for determining percent identity are well known in the art. For example, percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National Biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are well known in the art.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

By the term "degenerate variant" is intended a polynucleotide containing changes in the nucleic acid sequence thereof, that encodes a polypeptide having the same amino acid sequence as the polypeptide encoded by the polynucleotide from which the degenerate variant is derived.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus A transcription termination sequence may be located 3' to the coding sequence.

By "vector" is meant any genetic element, such as a plasmid, phage, transposon, cosmid, chromosome, virus, virion, etc., which is capable of replication when associated with the proper control elements and which can transfer gene sequences to cells. Thus, the term includes cloning and expression vehicles, as well as viral vectors.

By "recombinant vector" is meant a vector that includes a heterologous nucleic acid sequence which is capable of expression a cell.

A "recombinant viral vector" refers to a recombinant polynucleotide vector comprising one or more heterologous sequences (i.e., nucleic acid sequence not of viral origin). In the case of recombinant AAV vectors, the recombinant nucleic acid is flanked by at least one, in embodiments two, inverted terminal repeat sequences (ITRs).

A "recombinant AAV vector (rAAV vector)" refers to a polynucleotide vector comprising one or more heterologous sequences (i.e., nucleic acid sequence not of AAV origin) that are flanked by at least one, in embodiments two, AAV inverted terminal repeat sequences (ITRs). Such rAAV vectors can be replicated and packaged into infectious viral particles when present in a host cell that has been infected with a suitable helper virus (or that is expressing suitable helper functions) and that is expressing AAV rep and cap gene products (i.e. AAV Rep and Cap proteins). When a rAAV vector is incorporated into a larger polynucleotide (e.g., in a chromosome or in another vector such as a plasmid used for cloning or transfection), then the rAAV vector may be referred to as a "pro-vector" which can be "rescued" by replication and encapsidation in the presence of AAV packaging functions and suitable helper functions. A rAAV vector can be in any of a number of forms, including, but not limited to, plasmids, linear artificial chromosomes, complexed with lipids, encapsulated within liposomes, and encapsidated in a viral particle, particularly an AAV particle. A rAAV vector can be packaged into an AAV virus capsid to generate a "recombinant adeno-associated viral particle (rAAV particle)".

By "recombinant virus" is meant a virus that has been genetically altered, e.g., by the addition or insertion of a heterologous nucleic acid construct into the particle.

The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) *Virology*, 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA molecules into suitable host cells.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

A "nucleic acid" sequence refers to a DNA or RNA sequence. The term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxyl-methyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methyl-cytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters".

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The term "multimerization domain" as used in the context of the present invention, is meant to refer to the portion of the molecule to which the interleukin receptor is joined, either directly or through a "linker domain." The multimerization domain can be a polypeptide domain which facilitates the interaction of two or more multimerization domains and/or interleukin receptor domains. In embodiment, homodimers result from the pairing or crosslinking of two monomers comprising an interleukin receptor and a multimerization domain.

For example, a multimerization domain may be an immunoglobulin sequence, such as an immunoglobulin constant region, a leucine zipper, a hydrophobic region, a hydrophilic region, a polypeptide comprising a free thiol which forms an intermolecular disulfide bond between two or more multimerization domains or, for example a "protuberance-into-cavity" domain described in, for example, U.S. Pat. No. 5,731,168, incorporated herein by reference in its entirety. Protuberances are constructed by, e.g., replacing small amino acid side chains from the interface of a first polypeptide with a larger side chain (for example a tyrosine or tryptophan). Compensatory cavities of identical or similar size to the protuberances are optionally created on the interface of a second polypeptide by replacing large amino acid side chains with smaller ones (for example alanine or threonine).

Therefore, in aspects, the multimerization domain provides that portion of the molecule which promotes or allows the formation of dimers, trimers, and the like from monomeric domains. In aspects, multimerization domains are immunoglobulin constant region domains.

"Immunoglobulins" (Igs) are proteins, generally glycoproteins, that are antibodies or antibody-like molecules which lack antigen specificity Immunoglobulins are usually heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has an amino (N) terminal variable domain (VH) followed by carboxy (C) terminal constant domains. Each light chain has a variable N-terminal domain (VL) and a C-terminal constant domain; the constant domain of the light chain (CL) is aligned with the first constant domain (CH1) of the heavy chain, and the light chain variable domain is aligned with the variable domain of the heavy chain. According to the domain definition of immunoglobulin polypeptide chains, light (L) chains have two conformationally similar domains VL and CL; and heavy chains have four domains (VH, CH1, CH2, and CH3) each of which has one intrachain disulfide bridge.

Depending on the amino acid sequence of the constant (C) domain of the heavy chains, immunoglobulins can be assigned to different classes. There are five major classes of immunoglobulins: IgA, IgD, IgE, IgG, and IgM. The immunoglobulin class can be further divided into subclasses (isotypes), e.g., IgG1, IgG2, IgG3, IgG4, IgG5, IgA1, and IgA2. Each heavy chain has at one end a variable domain (VH) followed by a number of constant domains. The light chains of antibodies from any vertebrate species can be assigned to one of two distinct types called kappa (K) or lambda (λ), based upon the amino acid sequence of their constant domains.

The term "Fc region" refers to the C-terminal (constant) region of an immunoglobulin heavy chain. The Fc region may be a native sequence Fc region or a variant Fc region. Although the boundaries of the Fc region of an immunoglobulin heavy chain may vary, the human IgG heavy chain Fc region may stretch from an amino acid residue at position Cys226, or from Pro230, to the carboxyl-terminus of a full-length human IgG1. The Fc region of an immunoglobulin generally comprises two constant domains, CH2 and CH3. The last residue, lysine, in the heavy chain of IgG1 can but need not be present as the terminal residue in the Fc in the mature protein. One human IgG1 heavy chain Fc region is defined in NCBI accession number P01857.

The "CH2 domain" of a human IgG1 Fc region (also referred to as "Cγ2" domain) usually extends from about amino acid 231 to about amino acid 340 of a full-length IgG, but from Pro111 to Lys223 of the human IgG heavy chain Fc region.

The "CH3 domain" comprises the residues C-terminal to a CH2 domain in a human IgG1 Fc region (i.e. from about amino acid residue 341 to about amino acid residue 447 of a full-length IgG, but from Gly224 to Lys330 of a human IgG heavy chain Fc region).

The "hinge region" is generally defined as stretching from Glu216 to Pro230 of a full-length human IgG1 (Burton, *Molec. immunol.* (1985) 22:161-206), but from Glu99 to Pro110 of a human IgG heavy chain Fc region. Hinge regions of other IgG isotypes may be aligned with the IgG1 sequence by placing the first and last cysteine residues forming inter-heavy chain S—S bonds in the same positions.

The "lower hinge region" of an Fc region is normally defined as the stretch of residues immediately C-terminal to the hinge region, i.e. residues 233 to 239 of a full-length human IgG1.

A "native Fc region sequence" comprises an amino acid sequence identical to the amino acid sequence of an Fc region found in nature. Native human Fc region sequences include but are not limited to the human IgG1 Fc region (non-A and A allotypes); the human IgG2 Fc region; the human IgG3 Fc region; and the human IgG4 Fc region as well as naturally occurring variants thereof. Native Fc regions from other species, such as murine Fc regions, are also well known.

A "functional Fc region" possesses an "effector function" of a native Fc region. Exemplary "effector functions" include C1q binding; complement-dependent cytotoxicity; Fc receptor binding; antibody-dependent cell-mediated cytotoxicity (ADCC); phagocytosis; down regulation of cell surface receptors (e.g., B cell receptor; BCR), etc. Such effector functions typically require the Fc region to be combined with a binding domain (e.g., an interleukin ligand herein) and can be assessed using various assays known in the art. The Fc region can be a human Fc region, e.g. a native sequence human Fc region such as a human IgG1 (A and non-A allotypes), IgG2, IgG3 or IgG4 Fc region. Such sequences are known. See, e.g., PCT Publication NO. WO01/02440, incorporated herein by reference in its entirety.

The term "transgene" refers to a polynucleotide that is introduced into a cell and is capable of being transcribed into RNA and optionally, translated and/or expressed under appropriate conditions. In aspects, it confers a desired property to a cell into which it was introduced, or otherwise leads to a desired therapeutic or diagnostic outcome (e.g., transcribed into a molecule that confers a desired therapeutic or diagnostic outcome).

The terms "genome particles (gp)," "genome equivalents," or "genome copies" as used in reference to a viral titer, refer to the number of virions containing the recombinant AAV DNA genome, regardless of infectivity or functionality. The number of genome particles in a particular vector preparation can be measured by procedures such as described in the Examples herein, or for example, in Clark et al. (1999) *Hum. Gene Ther.*, 10:1031-1039; Veldwijk et al. (2002) *Mol. Ther.*, 6:272-278.

The terms "infection unit (iu)," "infectious particle," or "replication unit," as used in reference to a viral titer, refer to the number of infectious and replication-competent recombinant AAV vector particles as measured by the infectious center assay, also known as replication center assay, as described, for example, in McLaughlin et al. (1988) *J. Virol.*, 62:1963-1973.

The term "transducing unit (tu)" as used in reference to a viral titer, refers to the number of infectious recombinant AAV vector particles that result in the production of a functional transgene product as measured in functional assays such as described in Examples herein, or for example, in Xiao et al. (1997) *Exp. Neurobiol.*, 144:113-124; or in Fisher et al. (1996) *J. Virol.*, 70:520-532 (LFU assay).

An "inverted terminal repeat" or "ITR" sequence is a term well understood in the art and refers to relatively short sequences found at the termini of viral genomes which are in opposite orientation.

An "AAV inverted terminal repeat (ITR)" sequence, a term well-understood in the art, is an approximately 145-nucleotide sequence that is present at both termini of the native single-stranded AAV genome. The outermost 125 nucleotides of the ITR can be present in either of two alternative orientations, leading to heterogeneity between different AAV genomes and between the two ends of a single AAV genome. The outermost 125 nucleotides also contains several shorter regions of self-complementarity (designated A, A', B, B', C, C' and D regions), allowing intrastrand base-pairing to occur within this portion of the ITR.

A "terminal resolution sequence" or "trs" is a sequence in the D region of the AAV ITR that is cleaved by AAV rep proteins during viral DNA replication. A mutant terminal resolution sequence is refractory to cleavage by AAV rep proteins.

A "helper virus" for AAV refers to a virus that allows AAV (which is a defective parvovirus) to be replicated and packaged by a host cell. A helper virus provides "helper functions" which allow for the replication of AAV. A number of such helper viruses have been identified, including adenoviruses, herpesviruses and poxviruses such as vaccinia. The adenoviruses encompass a number of different subgroups, although Adenovirus type 5 of subgroup C (Ad5) is most commonly used. Numerous adenoviruses of human, non-human mammalian and avian origin are known and are available from depositories such as the ATCC. Viruses of the herpes family, which are also available from depositories such as ATCC, include, for example, herpes simplex viruses (HSV), Epstein-Barr viruses (EBV), cytomegaloviruses (CMV) and pseudorabies viruses (PRV). Examples of adenovirus helper functions for the replication of AAV include E1A functions, E1B functions, E2A functions, VA functions and E4orf6 functions.

A preparation of rAAV is said to be "substantially free" of helper virus if the ratio of infectious AAV particles to infectious helper virus particles is at least about $10^2$:1; at least about $10^4$:1, at least about $10^6$:1; or at least about $10^8$:1. Preparations can also be free of equivalent amounts of helper virus proteins (i.e., proteins as would be present as a result of such a level of helper virus if the helper virus particle impurities noted above were present in disrupted form). Viral and/or cellular protein contamination can generally be observed as the presence of Coomassie staining bands on SDS gels (e.g., the appearance of bands other than those corresponding to the AAV capsid proteins VP1, VP2 and VP3).

The term "modulate" means to affect (e.g., either upregulate, downregulate or otherwise control) the level of a signaling pathway. Cellular processes under the control of signal transduction include, but are not limited to, transcription of specific genes, normal cellular functions, such as metabolism, proliferation, differentiation, adhesion, apoptosis and survival, as well as abnormal processes, such as transformation, blocking of differentiation and metastasis.

"Active" or "activity" for purposes of the present invention refers to forms of an interleukin receptor polypeptide which retain a biological activity (either inhibitory or stimulatory) of the corresponding native or naturally occurring polypeptide. The activity may be greater than, equal to, or less than that observed with the corresponding native or naturally occurring polypeptide. As explained above, an activity includes modulating the level of the IL-17 signaling pathway in a subject suffering from macular degeneration.

By "isolated" when referring to a nucleotide sequence, is meant that the indicated molecule is present in the substantial absence of other biological macromolecules of the same type. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

For the purpose of describing the relative position of nucleotide sequences in a particular nucleic acid molecule throughout the instant application, such as when a particular nucleotide sequence is described as being situated "upstream," "downstream," "3-prime (3')" or "5-prime (5')" relative to another sequence, it is to be understood that it is the position of the sequences in the "sense" or "coding" strand of a DNA molecule that is being referred to as is conventional in the art.

The term "purified" refers to isolation of a substance (compound, polynucleotide, protein, polypeptide, polypeptide composition) such that the substance of interest comprises the majority percent of the sample in which it resides. Typically in a sample a substantially purified component comprises 50%, 80%-85%, 90-99%, such as at least 90%, 91%, 92%, 93%, 94%, 95%, 96%, 97%, 98%, 99% of the sample. Techniques for purifying polynucleotides and polypeptides of interest are well-known in the art and include, for example, ion-exchange chromatography, affinity chromatography and sedimentation according to density.

The terms "subject", "individual" or "patient" are used interchangeably herein and refer to a vertebrate, e.g., a mammal Mammals include, but are not limited to, murines, rodents, simians, humans, farm animals, sport animals and pets.

The terms "effective amount" or "therapeutically effective amount" of a composition or agent, as provided herein, refer to a sufficient amount of the composition or agent to provide the desired response, such as reducing or inhibiting the production of IL17A in the eye, or reducing, preventing or retarding progression of the physical changes in the eye related to macular degeneration, or reducing, preventing or retarding progression of the symptoms manifested therefrom (e.g., reduction in photoreceptor degeneration; reduction in RPE degradation; reduction in RPE stress; reduction in focal retinal degeneration; reduction in IS, OS, or RPE degenerative lesions; reduction in lipofuscin deposits; reduction in glycogen deposits; reduction in A2E concentration; reduction in RPE damage; reduction in mitochondrial damage; and the like). The exact amount required will vary from subject to subject, depending on the species, age, and general condition of the subject, the severity of the condition being treated, and the particular macromolecule of interest, mode of administration, and the like. An appropriate "effective" amount in any individual case may be determined by one of ordinary skill in the art using routine experimentation. See, e.g., Lim, J. (2012) Age-Related Macular Degeneration, CRC Press, Boca Raton; Kanski et al. (2011) Clinical Ophthalmology: A Systematic Approach, Elsevier Saunders.

"Treatment" or "treating" macular degeneration includes: (1) preventing the disease, i.e. preventing the development of the disease or causing the disease to occur with less intensity in a subject that may be exposed to or predisposed to the disease but does not yet experience or display symptoms of the disease, (2) inhibiting the disease, i.e., arresting the development, preventing or retarding progression, or reversing the disease state, (3) relieving symptoms of the disease i.e., decreasing the number of symptoms experienced by the subject, or (4) reducing, preventing or retarding progression of the physical changes in the eye related to macular degeneration. Treatment includes, but is not limited to, reduction in accumulation of drusen, abnormal blood vessel growth in the eye, abnormal fluid, blood and protein leakage in the eye, and the like. Treatment can be detected, for example, by monitoring the rate and amount of loss of photoreceptors (rods and cones) in the central part of the eye, by monitoring the rate of vision loss and the best corrected visual acuity (BCVA), by monitoring the rate and amount of atrophy of the retinal pigment epithelial layer (and the choriocapillaris) below the retina, by monitoring the amount of drusen (cellular debris) that accumulates between the retina and the choroid, by monitoring abnormal blood vessel growth in the eye, and monitoring the amount of abnormal fluid, blood and protein leakage in the eye.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless defined otherwise, all technical and scientific terms used herein have the same meanings as commonly understood by one of ordinary skill in the art to which this disclosure belongs. Although any methods and materials similar or equivalent to those described herein can be used in the practice or testing of the present invention, exemplary methods, devices, and materials are now described. All technical and patent publications cited herein are incorporated herein by reference in their entirety. Nothing herein is to be construed as an admission that the invention is not entitled to antedate such disclosure by virtue of prior invention.

It is to be understood, although not always explicitly stated that all numerical designations are preceded by the term "about." It also is to be understood, although not always explicitly stated, that the reagents described herein are merely exemplary and that equivalents of such are known in the art.

2. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

It should be appreciated that the invention should not be construed to be limited to the examples described herein. Methods and materials similar or equivalent to those described herein can be used in the practice of the present invention, and the invention should be construed to include any and all applications provided herein and all equivalent variations within the skill of the ordinary artisan.

Central to the present invention is the discovery that protein or gene therapy using constructs encoding IL17 inhibitors, such as IL17 receptors, serves to modulate the corresponding signaling pathways, and significantly ameliorate they symptoms/pathology associated with macular degeneration (e.g., photoreceptor and RPE degeneration; RPE stress; focal retinal degeneration; IS, OS, or RPE degenerative lesions; lipofuscin deposits; glycogen deposits; A2E accumulation; RPE damage; mitochondrial damage; and the like). Thus, the use of IL17 inhibitors provides a useful technique for treating and preventing macular degeneration. Protein and gene therapy techniques can be used alone or in combination, or in conjunction with traditional drugs.

In aspects, the IL17 inhibitor used in the present methods encodes a fusion protein that includes an interleukin receptor, or an active portion thereof, linked to a multimerization domain (e.g., an immunoglobulin constant region multimerization domain), either directly or via a linker. In embodiments, a soluble form, e.g., a transmembrane domain-deleted or inactivated form, of the receptor is used.

The receptor can be present either upstream or downstream from the multimerization domain. Purified fusion protein may be prepared from the constructs, and the fusion protein can be produced in multimeric form when expressed in vivo. The multimer can be a dimer, trimer, etc. In embodiments, the interleukin receptor is present in a homodimeric form. Thus, monomers of IL17r will form homodimers upon expression.

In order to further an understanding of the invention, a more detailed discussion is provided below regarding macular degeneration, IL17 inhibitors, receptor-immunoglobulin fusions, as well as various gene delivery methods for use with the present invention.

Macular Degeneration

As explained above, the present invention makes use of IL17 inhibitors in order to treat, prevent, alleviate, and/or prevent or retard progression of macular degeneration. In certain embodiments, an individual at risk of developing macular degeneration is administered an amount effective to delay or prevent the disease.

At least three forms of macular degeneration have been identified. (1) Atrophic, non-exudative-dry form of AMD, also known as central geographic atrophy, occurs in approximately 85 to 90% of patients with macular degeneration. The dry form of AMD typically results from atrophy of the retinal pigment epithelial layer (and presumably the choriocapillaris) below the retina and causes vision loss through loss of photoreceptors (rods and cones) in the central part of the eye. There can additionally be cellular debris (called drusen) accumulating between the retina and the choroid. (2) The wet form of AMD, also known as neovascular or exudative AMD, represents the more severe form of AMD. The wet form of AMD is typically characterized by abnormal blood vessel growth in the eye, wherein the faulty blood vessels leak fluids and blood. It may cause vision loss due to abnormal blood vessel growth from the choriocapillaries through Bruch's membrane into the subretinal space, ultimately leading to blood and protein leakage below the macula. Bleeding, leaking, and scarring from these blood vessels eventually causes irreversible damage to the photoreceptors, scar formation in the macula and relatively rapid vision loss if left untreated. (3) Pigment epithelial detachment associated (PED) ARMD occurs in less than 5% of patients and results in retinal detachment.

IL17 Inhibitors

The present invention makes use of IL17 inhibitors, e.g., IL17A inhibitors, to modulate IL17 activity and thereby treat, prevent, alleviate, and/or prevent or retard progression of macular degeneration.

Many IL17 inhibitors are suitable for use in the present methods. Non-limiting examples of IL17 inhibitors include IL17 receptors; anti-IL17 antibodies, including monoclonal antibodies, chimeric, humanized and recombinant antibodies, such as Ixekizumab, brodalumab, secukinomab, AMG 827; vidoflumis; methylprednisone; Curcumin (1,7-Bis (4-hydroxy-3-methoxyphenyl)-1,6 heptadiene-3,5-di-one) ursolic acid; small molecule inhibitors; phosphoinositide 3-kinases (PI3Ks) inhibitors; cyclosporine A; PDE4 inhibitors; caspase-1 inhibitors, and the like.

The ability of these as well as other molecules to inhibit IL17 can be determined using techniques well known in the art, such as known assays to determine IL17 binding and inhibition of IL17 signal pathways, as well as the use of animal models for the study of macular degeneration, such as the $Ccl2^{-/-}/Cx3cr1^{-/-}/Crb1^{rd8}$(DKO/rd8) mouse model of progressive, focal retinal degeneration (Chan et al., *Ophthalmic Res* (2000) 40:124-128; Tuo et al., *Invest Ophthalmol Vis Sci* (2007) 48:3827-3836), described herein.

In aspects, interleukin receptor-immunoglobulin fusions are used in the present methods. The interleukin receptor component of the fusions is an IL17 receptor (IL17r), such as an IL17A receptor. The native molecules, as well as active fragments and analogs thereof, which retain the ability to bind to the corresponding ligand and modulate ligand activity, as measured in any of the various assays and animal models including those described further herein, are intended for use with the present invention.

The nucleotide and corresponding amino acid sequence for a representative full-length human IL17A receptor is shown in FIGS. 1A and 1B, respectively (SEQ ID NOS:1 and 2, NCBI Accession No. NM_014339 and NP_055154, respectively). The full-length molecule includes 866 amino acids. Amino acids 1-31 represent a signal peptide. The signal peptide is followed by a mature peptide consisting of a 289 amino acid extracellular domain, a 21 amino acid transmembrane domain, and a 525 amino acid cytoplasmic tail. The amino acid sequence of the human IL17Ar is 69% identical to the mouse IL17Ar.

In aspects, soluble IL17r is used. A soluble IL17r typically includes the extracellular domain or an active portion thereof but lacks the transmembrane domain and, optionally, the cytoplasmic tail and may or may not include the native or a heterologous signal sequence. One example of a soluble IL17r comprises the signal peptide and the extracellular domain of the molecule, such as represented by residues 1 to 320 of SEQ ID NO:2, or an active fragment thereof.

Various other IL17r sequences and variants from humans and other species are known and can also be used herein. If a soluble form of the receptor is desired, the corresponding domains to those described above can be used and are readily identifiable by one of skill in the art, such as by using standard hydropathy plots, such as those calculated using the Kyte-Doolittle technique, Kyte et al., *J. Mol. Biol.* (1982) 157:105-132.

Additional IL17r sequences and variants thereof for use with the present invention are described in e.g., U.S. Pat. No. 7,256,264, incorporated herein by reference in its entirety, as well as NCBI accession numbers NM_014339, NM_032732, NM_153461, NM_153460, EF676034, NM_018725, AF212365, AF458069, AF458067, EF676033, EF676032, AF458065, U58917 (all human sequences); NM_008359, AK050139, AX720728, AF458066, NM_134159, AF458068, AF208108, U31993 (all mouse sequences); XM_603383 (bovine); XM_001489654 (horse); NM_01107883 (rat); XR_024768 (chimp); XM_533791 (dog).

Polynucleotides encoding the desired interleukin receptor for use with the present invention can be made using standard techniques of molecular biology. For example, polynucleotide sequences coding for the above-described molecules can be obtained using recombinant methods, such as by screening cDNA and genomic libraries from cells expressing the gene, or by deriving the gene from a vector known to include the same. The gene of interest can also be produced synthetically, rather than cloned, based on the known sequences. The molecules can be designed with appropriate codons for the particular sequence. The complete sequence is then assembled from overlapping oligonucleotides prepared by standard methods and assembled into a complete coding sequence. See, e.g., Edge, *Nature* (1981) 292:756; Nambair et al., *Science* (1984) 223:1299; and Jay et al., *J. Biol. Chem.* (1984) 259:6311.

Thus, particular nucleotide sequences can be obtained from vectors harboring the desired sequences or synthesized completely or in part using various oligonucleotide synthesis techniques known in the art, such as site-directed mutagenesis and polymerase chain reaction (PCR) techniques where appropriate. See, e.g., Sambrook, supra. One method of obtaining nucleotide sequences encoding the desired sequences is by annealing complementary sets of overlapping synthetic oligonucleotides produced in a conventional, automated polynucleotide synthesizer, followed by ligation with an appropriate DNA ligase and amplification of the ligated nucleotide sequence via PCR. See, e.g., Jayaraman et al., *Proc. Natl. Acad. Sci. USA* (1991) 88:4084-4088. Additionally, oligonucleotide-directed synthesis (Jones et al., *Nature* (1986) 54:75-82), oligonucleotide directed mutagenesis of preexisting nucleotide regions (Riechmann et al., *Nature* (1988) 332:323-327 and Verhoeyen et al., *Science* (1988) 239:1534-1536), and enzymatic filling-in of gapped oligonucleotides using $T_4$ DNA polymerase (Queen et al., *Proc. Natl. Acad. Sci. USA* (1989) 86:10029-10033) can be used to provide molecules for use in the subject methods.

Once obtained, the polynucleotide encoding the interleukin receptor can be linked to a multimerization domain either directly or via a linker moiety. A multimerization domain may be an immunoglobulin sequence, such as an immunoglobulin constant region, a leucine zipper, a hydrophobic region, a hydrophilic region, a polypeptide comprising a free thiol which forms an intermolecular disulfide bond between two or more multimerization domains or, for example a "protuberance-into-cavity" domain described in, for example, U.S. Pat. No. 5,731,168, incorporated herein by reference in its entirety. The multimerization domain provides a portion of the molecule which promotes or allows the formation of dimers, trimers, and the like from monomeric domains.

Multimerization domains can cause at least 5%, 10%, 20%, 30%, 40%, 50%, 60%, 75%, 80%, 85%, 90%, or 95% of the monomeric fusion proteins to migrate on a non-denaturing polyacrylamide gel at a rate appropriate for a multimer. Glycosylation can affect the migration of a protein in a gel. Although particular sequences are shown here, variants such as allelic variants can be used as well. Typically such variants will have at least 85%, 90%, 95%, 97%, 98%, or 99% identity with the disclosed sequence.

Multimerization can be assayed, for example, using reducing and non-reducing gels. Multimerization can also be assayed by detection of increased binding affinity of a protein for its ligand/receptor. BiaCore™ surface plasmon resonance assays can be used in this regard. These assays detect changes in mass by measuring changes in refractive index in an aqueous layer close to a sensor chip surface. Any method known in the art can be used to detect multimerization.

In aspects, multimerization domains are derived from immunoglobulin molecules, including but not limited to regions from the heavy chain, immunoglobulin constant region domains, Fc regions, and the like. Sequences of the Fc portion of IgG1 or IgG2 lambda heavy chain can be used, for example, CH3 alone or portions of CH3, such as amino acids Gly224-Lys330, numbered relative to the human IgG1 Fc portion or both of CH2 and CH3 domains or portions thereof, such as amino acids Pro111-Lys330, numbered relative to the human IgG1 Fc portion, or portions or extensions thereof.

The Fc portion of an immunoglobulin molecule can be obtained by cleavage of whole antibody molecules with the enzyme papain. Other means can be used to obtain these portions. For the IgG1 lambda heavy chain protein sequence, see Genbank accession no Y14737. Other Fc regions can be used for example from other IgG types and from IgA, IgM, IgD, or IgE antibodies.

As explained above, the interleukin receptor can be linked to a multimerization domain via a linker. In embodiments, linkers are polypeptide chains. Linker moieties can include, for example, 3-100 amino acid residues, such as 5-100 amino acid residues, 5-75 amino acid residues, 5-50 amino acid residues, 5-25 amino acid residues, 5-20 amino acid residues, 5-15 amino acid residues, 5-10 amino acid residues, 5-9 amino acid residues, or any number of amino acid residues within these ranges. Examples of useful linkers include: $Gly_9$ (SEQ ID NO:5), $Glu_9$ (SEQ ID NO:6), $Ser_9$ (SEQ ID NO:7), $Gly_5$-Cys-$Pro_2$-Cys (SEQ ID NO:8), $(Gly_4$-Ser$)_3$ (SEQ ID NO:9), Ser-Cys-Val-Pro-Leu-Met-Arg-Cys-Gly-Gly-Cys-Cys-Asn (SEQ ID NO:10), Pro-Ser-Cys-Val-Pro-Leu-Met-Arg-Cys-Gly-Gly-Cys-Cys-Asn (SEQ ID NO: 11), Gly-Asp-Leu-Ile-Tyr-Arg-Asn-Gln-Lys (SEQ ID NO:12), and $Gly_9$-Pro-Ser-Cys-Val-Pro-Leu-Met-Arg-Cys-Gly-Gly-Cys-Cys-Asn (SEQ ID NO:13). Other polypeptide linkers which can be used include a polyglycine of different lengths, including for example, 5, 7, or 30 residues.

Linker moieties can also be made from other polymers, such as polyethylene glycol. Such linkers can have from 10-1000, 10-500, 10-250, 10-100, or 10-50 ethylene glycol monomer units, or any number of monomer units within these ranges. Suitable polymers should be of a size similar to the size occupied by the appropriate range of amino acid residues. In embodiments, the polymer provides a spacing of from about 10-25 angstroms.

The sequences for the multimerization domain and the linker moiety can be obtained as described above with respect to the interleukin receptor.

An exemplary fusion is depicted diagrammatically in FIG. 2, the sequence of which is presented in FIGS. 3A-3B (SEQ ID NOS:3 and 4). As shown in FIG. 2, the construct encodes a soluble human IL17r linked by a sequence of nine glycines to the CH3 domain of the human IgG1 Fc domain.

Once produced, the constructs can be delivered using recombinant viral vectors as described further below.

Gene Delivery Techniques

The IL17 inhibitor constructs, such as those described above, can be delivered to the subject in question using any of several gene-delivery techniques. Several methods for gene delivery are known in the art. Generally, recombinant vectors are formulated into pharmaceutical compositions as described below and introduced into the subject using either in vivo or ex vivo transduction techniques. If transduced ex vivo, the desired recipient cell will be removed from the subject, transduced with the recombinant vector and reintroduced into the subject. Alternatively, syngeneic or xenogeneic cells can be used where those cells will not generate an inappropriate immune response in the subject.

Suitable methods for the delivery and introduction of transduced cells into a subject have been described. For example, cells can be transduced in vitro by combining recombinant vectors with the subject's cells e.g., in appropriate media, and screening for those cells harboring the DNA of interest using conventional techniques such as Southern blots and/or PCR, or by using selectable markers.

A number of viral based systems have been developed for gene transfer into mammalian cells either in vivo or ex vivo. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems have been described. See, e.g., U.S. Pat. No. 5,219,740; Miller and Rosman, BioTechniques (1989) 7:980-990; Miller, A. D., Human Gene Therapy (1990) 1:5-14; Scarpa et al., Virology (1991) 180:849-852; Burns et al., Proc. Natl. Acad. Sci. USA (1993) 90:8033-8037; and Boris-Lawrie and Temin, Cur. Opin. Genet. Develop. (1993) 3:102-109. Replication-defective murine retroviral vectors are widely utilized gene transfer vectors. Murine leukemia retroviruses include a single strand RNA complexed with a nuclear core protein and polymerase (pol) enzymes encased by a protein core (gag) and surrounded by a glycoprotein envelope (env) that determines host range. The genomic structure of retroviruses include gag, pol, and env genes enclosed at the 5' and 3' long terminal repeats (LTRs). Retroviral vector systems exploit the fact that a minimal vector containing the 5' and 3' LTRs and the packaging signal are sufficient to allow vector packaging and infection and integration into target cells provided that the viral structural proteins are supplied in trans in the packaging cell line. Fundamental advantages of retroviral vectors for gene transfer include efficient infection and gene expression in most cell types, precise single copy vector integration into target cell chromosomal DNA and ease of manipulation of the retroviral genome.

A number of adenovirus vectors have also been described. Unlike retroviruses which integrate into the host genome, adenoviruses persist extrachromosomally thus minimizing the risks associated with insertional mutagenesis (Haj-Ahmad and Graham, J. Virol. (1986) 57:267-274; Bett et al., J. Virol. (1993) 67:5911-5921; Mittereder et al., Human Gene Therapy (1994) 5:717-729; Seth et al., J. Virol. (1994) 68:933-940; Barr et al., Gene Therapy (1994) 1:51-58; Berkner, K. L. BioTechniques (1988) 6:616-629; and Rich et al., Human Gene Therapy (1993) 4:461-476). Adenovirus vectors for use in the subject methods are described in more detail below.

Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., Molec. Cell. Biol. (1988) 8:3988-3996; Vincent et al., Vaccines 90 (1990) (Cold Spring Harbor Laboratory Press); Carter, B. J. Current Opinion in Biotechnology (1992) 3:533-539; Muzyczka, N. Current Topics in Microbiol. and Immunol. (1992) 158:97-129; Kotin, R. M. Human Gene Therapy (1994) 5:793-801; Shelling and Smith, Gene Therapy (1994) 1:165-169; and Zhou et al., J. Exp. Med. (1994) 179:1867-1875. AAV vector systems are also described in further detail below.

Additional viral vectors which will find use for delivering the nucleic acid molecules of interest include those derived from the pox family of viruses, including vaccinia virus and avian poxvirus. By way of example, vaccinia virus recombinants expressing the genes can be constructed as follows. The DNA encoding the particular polypeptide is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the protein into the viral genome. The resulting TK-recombinant can be selected by culturing the cells in the presence of 5-bromodeoxyuridine and picking viral plaques resistant thereto.

Alternatively, avipoxviruses, such as the fowlpox and canarypox viruses, can also be used to deliver the genes. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors described in Michael et al., J. Biol. Chem. (1993) 268:6866-6869 and Wagner et al., Proc. Natl. Acad. Sci. USA (1992) 89:6099-6103, can also be used for gene delivery.

Members of the Alphavirus genus, such as but not limited to vectors derived from the Sindbis and Semliki Forest viruses, will also find use as viral vectors for delivering the polynucleotide encoding the fusion. For a description of Sinbus-virus derived vectors useful for the practice of the instant methods, see, Dubensky et al., J. Virol. (1996) 70:508-519; and International Publication Nos. WO 95/07995 and WO 96/17072.

Alternatively, the interleukin receptor fusions can be delivered without the use of viral vectors, such as by using plasmid-based nucleic acid delivery systems as described in U.S. Pat. Nos. 6,413,942; 6,214,804; 5,580,859; 5,589,466; 5,763,270; and 5,693,622, all incorporated herein by reference in their entireties. Plasmids will include the gene of interest operably linked to control elements that direct the expression of the protein product in vivo. Such control elements are well known in the art.

Adenovirus Gene Delivery Systems

In one embodiment of the subject invention, a nucleotide sequence encoding the IL17 inhibitor, such as the fusions described above, is inserted into an adenovirus-based expression vector. The adenovirus genome is a linear double-stranded DNA molecule of approximately 36,000 base pairs with the 55-kDa terminal protein covalently bound to the 5' terminus of each strand. Adenoviral ("Ad") DNA contains identical Inverted Terminal Repeats ("ITRs") of about 100 base pairs with the exact length depending on the serotype. The viral origins of replication are located within the ITRs exactly at the genome ends. DNA synthesis occurs in two stages. First, replication proceeds by strand displacement, generating a daughter duplex molecule and a parental displaced strand. The displaced strand is single-stranded and can form a "panhandle" intermediate, which allows replication initiation and generation of a daughter duplex molecule. Alternatively, replication can proceed from both ends of the genome simultaneously, obviating the requirement to form the panhandle structure.

During the productive infection cycle, the viral genes are expressed in two phases: the early phase, which is the period up to viral DNA replication, and the late phase, which coincides with the initiation of viral DNA replication. During the early phase only the early gene products, encoded by regions E1, E2, E3 and E4, are expressed, which carry out a number of functions that prepare the cell for synthesis of viral structural proteins. During the late phase, late viral gene products are expressed in addition to the early gene products and host cell DNA and protein synthesis are shut off. Consequently, the cell becomes dedicated to the production of viral DNA and of viral structural proteins.

The E1 region of adenovirus is the first region expressed after infection of the target cell. This region consists of two transcriptional units, the E1A and E1B genes. The main functions of the E1A gene products are to induce quiescent cells to enter the cell cycle and resume cellular DNA synthesis, and to transcriptionally activate the E1B gene and the other early regions (E2, E3, E4). Transfection of primary cells with the E1A gene alone can induce unlimited proliferation (immortalization), but does not result in complete transformation. However, expression of E1A in most cases results in induction of programmed cell death (apoptosis), and only occasionally immortalization. Co-expression of the E1B gene is required to prevent induction of apoptosis and for complete morphological transformation to occur. In established immortal cell lines, high level expression of E1A can cause complete transformation in the absence of E1B.

The E1B-encoded proteins assist E1A in redirecting the cellular functions to allow viral replication. The E1B 55 kD and E4 33 kD proteins, which form a complex that is essentially localized in the nucleus, function in inhibiting the synthesis of host proteins and in facilitating the expression of viral genes. Their main influence is to establish selective transport of viral mRNAs from the nucleus to the cytoplasm, concomitantly with the onset of the late phase of infection. The E1B 21 kD protein is important for correct temporal control of the productive infection cycle, thereby preventing premature death of the host cell before the virus life cycle has been completed.

Adenoviral-based vectors express gene product peptides at high levels. Adenoviral vectors have high efficiencies of infectivity, even with low titers of virus. Additionally, the virus is fully infective as a cell-free virion so injection of producer cell lines are not necessary. Adenoviral vectors achieve long-term expression of heterologous genes in vivo. Adenovirus is not associated with severe human pathology, the virus can infect a wide variety of cells and has a broad host-range, the virus can be produced in large quantities with relative ease, and the virus can be rendered replication defective by deletions in the early-region 1 ("E1") of the viral genome. Thus, vectors derived from human adenoviruses, in which at least the E1 region has been deleted and replaced by a gene of interest, have been used extensively for gene therapy experiments in the pre-clinical and clinical phase.

Adenoviral vectors for use with the present invention are derived from any of the various adenoviral serotypes, including, without limitation, any of the over 40 serotype strains of adenovirus, such as serotypes 2, 5, 12, 40, and 41. The adenoviral vectors used herein are replication-deficient and contain the gene of interest under the control of a suitable promoter, such as any of the promoters discussed below with reference to adeno-associated virus. For example, U.S. Pat. No. 6,048,551, incorporated herein by reference in its entirety, describes replication-deficient adenoviral vectors that include the human gene for the anti-inflammatory cytokine IL-10, as well as vectors that include the gene for the anti-inflammatory cytokine IL-1ra, under the control of the Rous Sarcoma Virus (RSV) promoter, termed Ad.RSVIL-10 and Ad.RSVIL-1ra, respectively.

Other recombinant adenoviruses, derived from any of the adenoviral serotypes, and with different promoter systems, can be used by those skilled in the art.

For example, U.S. Pat. No. 6,306,652, incorporated herein by reference in its entirety, describes adenovirus vectors with E2A sequences, containing the hr mutation and the ts125 mutation, termed ts400, to prevent cell death by E2A overexpression, as well as vectors with E2A sequences, containing only the hr mutation, under the control of an inducible promoter, and vectors with E2A sequences, containing the hr mutation and the ts125 mutation (ts400), under the control of an inducible promoter.

Moreover, "minimal" adenovirus vectors as described in U.S. Pat. No. 6,306,652 will find use with the present invention. Such vectors retain at least a portion of the viral genome that is required for encapsidation of the genome into virus particles (the encapsidation signal), as well as at least one copy of at least a functional part or a derivative of the ITR. Packaging of the minimal adenovirus vector can be achieved by co-infection with a helper virus or, alternatively, with a packaging-deficient replicating helper system as described in U.S. Pat. No. 6,306,652.

Other useful adenovirus-based vectors for delivery of the gene of interest include the "gutless" (helper-dependent) adenovirus in which the vast majority of the viral genome has been removed (Wu et al., Anesthes. (2001) 94:1119-1132). Such "gutless" adenoviral vectors essentially create no viral proteins, thus allowing virally driven gene therapy to successfully ensue for over a year after a single administration (Parks, R. J., Clin. Genet. (2000) 58:1-11; Tsai et al., Curr. Opin. Mol. Ther. (2000) 2:515-523) and eliminates interference by the immune system. In addition, removal of the viral genome creates space for insertion of control sequences that provide expression regulation by systemically administered drugs (Burcin et al., Proc. Natl. Acad. Sci. USA (1999) 96:355-360), adding both safety and control of virally driven protein expression. These and other recombinant adenoviruses will find use with the present methods.

Adeno-Associated Virus Gene Delivery Systems

Adeno-associated virus (AAV) has been used with success to deliver genes for gene therapy. The AAV genome is a linear, single-stranded DNA molecule containing about 4681 nucleotides. The AAV genome generally comprises an internal, nonrepeating genome flanked on each end by inverted terminal repeats (ITRs). The ITRs are approximately 145 base pairs (bp) in length. The ITRs have multiple functions, including providing origins of DNA replication, and packaging signals for the viral genome. The internal nonrepeated portion of the genome includes two large open reading frames, known as the AAV replication (rep) and capsid (cap) genes. The rep and cap genes code for viral proteins that allow the virus to replicate and package into a virion. In particular, a family of at least four viral proteins are expressed from the AAV rep region, Rep 78, Rep 68, Rep 52, and Rep 40, named according to their apparent molecular weight. The AAV cap region encodes at least three proteins, VP1, VP2, and VP3.

AAV has been engineered to deliver genes of interest by deleting the internal nonrepeating portion of the AAV genome (i.e., the rep and cap genes) and inserting a heterologous gene (in this case, the gene encoding the interleukin receptor fusion) between the ITRs. The heterologous gene is typically functionally linked to a heterologous promoter (constitutive, cell-specific, or inducible) capable of driving gene expression in the patient's target cells under appropriate conditions. Termination signals, such as polyadenylation sites, can also be included.

AAV is a helper-dependent virus; that is, it requires coinfection with a helper virus (e.g., adenovirus, herpesvirus or vaccinia), in order to form AAV virions. In the absence of coinfection with a helper virus, AAV establishes a latent state in which the viral genome inserts into a host cell chromosome, but infectious virions are not produced. Subsequent infection by a helper virus "rescues" the integrated genome, allowing it to replicate and package its genome into an infectious AAV virion. While AAV can infect cells from different species, the helper virus must be of the same species as the host cell. Thus, for example, human AAV will replicate in canine cells coinfected with a canine adenovirus.

Recombinant AAV virions comprising the gene of interest may be produced using a variety of art-recognized techniques described more fully below. Wild-type AAV and helper viruses may be used to provide the necessary replicative functions for producing rAAV virions (see, e.g., U.S. Pat. No. 5,139,941, incorporated herein by reference in its entirety). Alternatively, a plasmid, containing helper function genes, in combination with infection by one of the well-known helper viruses can be used as the source of replicative functions (see e.g., U.S. Pat. Nos. 5,622,856 and 5,139,941, both incorporated herein by reference in their entireties). Similarly, a plasmid, containing accessory function genes can be used in combination with infection by wild-type AAV, to provide the necessary replicative functions. These three approaches, when used in combination with a rAAV vector, are each sufficient to produce rAAV virions. Other approaches, well known in the art, can also be employed by the skilled artisan to produce rAAV virions.

In one embodiment of the present invention, a triple transfection method (described in detail in U.S. Pat. No. 6,001,650, incorporated by reference herein in its entirety) is used to produce rAAV virions because this method does not require the use of an infectious helper virus, enabling rAAV virions to be produced without any detectable helper virus present. This is accomplished by use of three vectors for rAAV virion production: an AAV helper function vector, an accessory function vector, and a rAAV expression vector. One of skill in the art will appreciate, however, that the nucleic acid sequences encoded by these vectors can be provided on two or more vectors in various combinations.

As explained herein, the AAV helper function vector encodes the "AAV helper function" sequences (i.e., rep and cap), which function in trans for productive AAV replication and encapsidation. The AAV helper function vector can support efficient AAV vector production without generating any detectable wt AAV virions (i.e., AAV virions containing functional rep and cap genes). An example of such a vector, pHLP19, is described in U.S. Pat. No. 6,001,650, incorporated herein by reference in its entirety. The rep and cap genes of the AAV helper function vector can be derived from any of the known AAV serotypes, as explained above. For example, the AAV helper function vector may have a rep gene derived from AAV-2 and a cap gene derived from AAV-6; one of skill in the art will recognize that other rep and cap gene combinations are possible, the defining feature being the ability to support rAAV virion production.

The accessory function vector encodes nucleotide sequences for non-AAV-derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the well-known helper viruses such as adenovirus, herpesvirus (other than herpes simplex virus type-1), and vaccinia virus. In embodiments, the accessory function plasmid pLadeno5 is used (details regarding pLadeno5 are described in U.S. Pat. No. 6,004,797, incorporated herein by reference in its entirety). This plasmid provides a complete set of adenovirus accessory functions for AAV vector production, but lacks the components necessary to form replication-competent adenovirus.

In order to further an understanding of AAV, a more detailed discussion is provided below regarding recombinant AAV expression vectors and AAV helper and accessory functions Recombinant AAV Expression Vectors Recombinant AAV (rAAV) expression vectors are constructed using known techniques to at least provide as operatively linked components in the direction of transcription, control elements including a transcriptional initiation region, the polynucleotide of interest and a transcriptional termination region. The control elements are selected to be functional in the cell of interest, such as in a mammalian cell. The resulting construct which contains the operatively linked components is bounded (5' and 3') with functional AAV ITR sequences.

The nucleotide sequences of AAV ITR regions are known. See, e.g., Kotin, R. M. (1994) *Human Gene Therapy* 5:793-801; Berns, K. I. "Parvoviridae and their Replication" in *Fundamental Virology*, 2nd Edition, (B. N. Fields and D. M. Knipe, eds.) for the AAV-2 sequence. AAV ITRs used in the vectors of the invention need not have a wild-type nucleotide sequence, and may be altered, e.g., by the insertion, deletion or substitution of nucleotides. Additionally, AAV ITRs may be derived from any of several AAV serotypes, including without limitation, AAV1, AAV2, AAV3, AAV4, AAV5, AAV6, AAV7, AAV8, AAVrh8, AAVrh8R, AAV9, AAV10, AAVrh10, AAV11, or AAV12, and the like. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

Suitable polynucleotide molecules for use in AAV vectors will be less than about 5 kilobases (kb) in size. The selected polynucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, neuron-specific enolase promoter, a GFAP promoter, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

The AAV expression vector which harbors the polynucleotide molecule of interest bounded by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al. (1988) *Molec. Cell. Biol.* 8:3988-3996; Vincent et al. (1990) *Vaccines* 90 (Cold Spring Harbor Laboratory Press); Carter (1992) *Current Opinion in Biotechnology* 3:533-539; Muzyczka (1992) *Current Topics in Microbiol. and Immunol.* 158:97-129; Kotin (1994) *Human Gene Therapy* 5:793-801; Shelling and Smith (1994) *Gene Therapy* 1:165-169; and Zhou et al. (1994) *J. Exp. Med.* 179:1867-1875.

Alternatively, AAV ITRs can be excised from the viral genome or from an AAV vector containing the same and fused 5' and 3' of a selected nucleic acid construct that is present in another vector using standard ligation techniques, such as those described in Sambrook et al., supra. For example, ligations can be accomplished in 20 mM Tris-Cl pH 7.5, 10 mM MgCl2, 10 mM DTT, 33 µg/ml BSA, 10 mM-50 mM NaCl, and either 40 µM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 µg/ml total DNA concentrations (5-100 nM total end concentration). AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226.

For the purposes of the invention, suitable host cells for producing rAAV virions from the AAV expression vectors include microorganisms, yeast cells, insect cells, and mammalian cells, that can be, or have been, used as recipients of a heterologous DNA molecule and that are capable of growth in, for example, suspension culture, a bioreactor, or the like. The term includes the progeny of the original cell which has been transfected. Thus, a "host cell" as used herein generally refers to a cell which has been transfected with an exogenous DNA sequence. Cells from the stable human cell line, 293 (readily available through, e.g., the American Type Culture Collection under Accession Number ATCC CRL1573) can be used in the practice of the present invention. Particularly, the human cell line 293 is a human embryonic kidney cell line that has been transformed with adenovirus type-5 DNA fragments (Graham et al. (1977) *J. Gen. Virol.* 36:59), and expresses the adenoviral E1a and E1b genes (Aiello et al. (1979) *Virology* 94:460). The 293 cell line is readily transfected, and provides a particularly convenient platform in which to produce rAAV virions.

AAV Helper Functions

Host cells containing the above-described AAV expression vectors must be rendered capable of providing AAV helper functions in order to replicate and encapsidate the nucleotide sequences flanked by the AAV ITRs to produce rAAV virions. AAV helper functions are generally AAV-derived coding sequences which can be expressed to provide AAV gene products that, in turn, function in trans for productive AAV replication. AAV helper functions are used herein to complement necessary AAV functions that are missing from the AAV expression vectors. Thus, AAV helper functions include one, or both of the major AAV ORFs, namely the rep and cap coding regions, or functional homologues thereof.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. For a description of the AAV rep coding region, see, e.g., Muzyczka, N. (1992) *Current Topics in Microbiol. and Immunol.* 158:97-129; and Kotin, R. M. (1994) *Human Gene Therapy* 5:793-801. Suitable homologues of the AAV rep coding region include the human herpesvirus 6 (HHV-6) rep gene which is also known to mediate AAV-2 DNA replication (Thomson et al. (1994) *Virology* 204:304-311).

By "AAV cap coding region" is meant the art-recognized region of the AAV genome which encodes the capsid proteins VP1, VP2, and VP3, or functional homologues thereof. These Cap expression products supply the packaging functions which are collectively required for packaging the viral genome. For a description of the AAV cap coding region, see, e.g., Muzyczka, N. and Kotin, R. M. (supra).

AAV helper functions are introduced into the host cell by transfecting the host cell with an AAV helper construct either prior to, or concurrently with, the transfection of the AAV expression vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves.

These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) *J. Virol.* 63:3822-3828; and McCarty et al. (1991) *J. Virol.* 65:2936-2945. A number of other vectors have been described which encode Rep and/or Cap expression products. See, e.g., U.S. Pat. No. 5,139,941.

AAV Accessory Functions

The host cell (or packaging cell) must also be rendered capable of providing nonAAV-derived functions, or "accessory functions," in order to produce rAAV virions. Accessory functions are nonAAV-derived viral and/or cellular functions upon which AAV is dependent for its replication. Thus, accessory functions include at least those nonAAV proteins and RNAs that are required in AAV replication, including those involved in activation of AAV gene transcription, stage specific AAV mRNA splicing, AAV DNA replication, synthesis of Cap expression products and AAV capsid assembly. Viral-based accessory functions can be derived from any of the known helper viruses.

In particular, accessory functions can be introduced into and then expressed in host cells using methods known to those of skill in the art. Typically, accessory functions are provided by infection of the host cells with an unrelated helper virus. A number of suitable helper viruses are known, including adenoviruses; herpesviruses such as herpes simplex virus types 1 and 2; and vaccinia viruses. Nonviral accessory functions will also find use herein, such as those provided by cell synchronization using any of various known agents. See, e.g., Buller et al. (1981) *J. Virol.*

40:241-247; McPherson et al. (1985) *Virology* 147:217-222; Schlehofer et al. (1986) *Virology* 152:110-117.

Alternatively, accessory functions can be provided using an accessory function vector as defined above. See, e.g., U.S. Pat. No. 6,004,797 and International Publication No. WO 01/83797, incorporated herein by reference in their entireties. Nucleic acid sequences providing the accessory functions can be obtained from natural sources, such as from the genome of an adenovirus particle, or constructed using recombinant or synthetic methods known in the art. As explained above, it has been demonstrated that the full-complement of adenovirus genes are not required for accessory helper functions. In particular, adenovirus mutants incapable of DNA replication and late gene synthesis have been shown to be permissive for AAV replication. Ito et al., (1970) *J. Gen. Virol.* 9:243; Ishibashi et al, (1971) *Virology* 45:317. Similarly, mutants within the E2B and E3 regions have been shown to support AAV replication, indicating that the E2B and E3 regions are probably not involved in providing accessory functions. Carter et al., (1983) *Virology* 126:505. However, adenoviruses defective in the E1 region, or having a deleted E4 region, are unable to support AAV replication. Thus, E1A and E4 regions are likely required for AAV replication, either directly or indirectly. Laughlin et al., (1982) *J. Virol.* 41:868; Janik et al., (1981) *Proc. Natl. Acad. Sci. USA* 78:1925; Carter et al., (1983) *Virology* 126:505. Other characterized Ad mutants include: E1B (Laughlin et al. (1982), supra; Janik et al. (1981), supra; Ostrove et al., (1980) *Virology* 104:502); E2A (Handa et al., (1975) *J. Gen. Virol.* 29:239; Strauss et al., (1976) *J. Virol.* 17:140; Myers et al., (1980) *J. Virol.* 35:665; Jay et al., (1981) *Proc. Natl. Acad. Sci. USA* 78:2927; Myers et al., (1981) *J. Biol. Chem.* 256:567); E2B (Carter, *Adeno-Associated Virus Helper Functions, in I CRC Handbook of Parvoviruses* (P. Tijssen ed., 1990)); E3 (Carter et al. (1983), supra); and E4 (Carter et al. (1983), supra; Carter (1995)). Although studies of the accessory functions provided by adenoviruses having mutations in the E1B coding region have produced conflicting results, Samulski et al., (1988) *J. Virol.* 62:206-210, has reported that E1B55k is required for AAV virion production, while E1B19k is not. In addition, International Publication WO 97/17458 and Matshushita et al., (1998) *Gene Therapy* 5:938-945, describe accessory function vectors encoding various Ad genes. Accessory function vectors can comprise an adenovirus VA RNA coding region, an adenovirus E4 ORF6 coding region, an adenovirus E2A 72 kD coding region, an adenovirus E1A coding region, and an adenovirus E1B region lacking an intact E1B55k coding region. Such vectors are described in International Publication No. WO 01/83797.

As a consequence of the infection of the host cell with a helper virus, or transfection of the host cell with an accessory function vector, accessory functions are expressed which transactivate the AAV helper construct to produce AAV Rep and/or Cap proteins. The Rep expression products excise the recombinant DNA (including the DNA of interest) from the AAV expression vector. The Rep proteins also serve to duplicate the AAV genome. The expressed Cap proteins assemble into capsids, and the recombinant AAV genome is packaged into the capsids. Thus, productive AAV replication ensues, and the DNA is packaged into rAAV virions. A "recombinant AAV virion," or "rAAV virion" is defined herein as an infectious, replication-defective virus including an AAV protein shell, encapsidating a heterologous nucleotide sequence of interest which is flanked on both sides by AAV ITRs.

Following recombinant AAV replication, rAAV virions can be purified from the host cell using a variety of conventional purification methods, such as column chromatography, CsCl gradients, and the like. For example, a plurality of column purification steps can be used, such as purification over an anion exchange column, an affinity column and/or a cation exchange column. See, for example, International Publication No. WO 02/12455. Further, if infection is employed to express the accessory functions, residual helper virus can be inactivated, using known methods. For example, adenovirus can be inactivated by heating to temperatures of approximately 60° C. for, e.g., 20 minutes or more. This treatment effectively inactivates only the helper virus since AAV is extremely heat stable while the helper adenovirus is heat labile.

The resulting rAAV virions containing the nucleotide sequence of interest can then be used for gene delivery using the techniques described below.

rAAV Particles

In some embodiments, the viral particle is a recombinant AAV particle comprising a nucleic acid comprising a transgene flanked by one or two ITRs. The nucleic acid is encapsidated in the AAV particle. The AAV particle also comprises capsid proteins. In some embodiments, the nucleic acid comprises the protein coding sequence(s) of interest (e.g., a therapeutic transgene) operatively linked components in the direction of transcription, control sequences including transcription initiation and termination sequences, thereby forming an expression cassette. The expression cassette is flanked on the 5' and 3' end by at least one functional AAV ITR sequences. By "functional AAV ITR sequences" it is meant that the ITR sequences function as intended for the rescue, replication and packaging of the AAV virion. See Davidson et al., *PNAS*, 2000, 97(7)3428-32; Passini et al., *J. Virol.*, 2003, 77(12):7034-40; and Pechan et al., *Gene Ther.*, 2009, 16:10-16, all of which are incorporated herein in their entirety by reference. For practicing some aspects of the invention, the recombinant vectors comprise at least all of the sequences of AAV essential for encapsidation and the physical structures for infection by the rAAV. AAV ITRs for use in the vectors of the invention need not have a wild-type nucleotide sequence (e.g., as described in Kotin, *Hum. Gene Ther.*, 1994, 5:793-801), and may be altered by the insertion, deletion or substitution of nucleotides or the AAV ITRs may be derived from any of several AAV serotypes. More than 40 serotypes of AAV are currently known, and new serotypes and variants of existing serotypes continue to be identified. See Gao et al., *PNAS*, 2002, 99(18): 11854-6; Gao et al., *PNAS*, 2003, 100(10): 6081-6; and Bossis et al., *J. Virol.*, 2003, 77(12):6799-810. Use of any AAV serotype is considered within the scope of the present invention. In some embodiments, a rAAV vector is a vector derived from an AAV serotype, including without limitation, AAV1, AAV2, AAV3, AAV4, AAV5, AAV6, AAV7, AAV8, AAVrh8, AAVrh8R, AAV9, AAV10, AAVrh10, AAV11, or AAV12, or the like. In some embodiments, the nucleic acid in the AAV comprises an ITR of AAV1, AAV2, AAV3, AAV4, AAV5, AAV6, AAV7, AAV8, AAVrh8, AAVrh8R, AAV9, AAV10, AAVrh10, AAV11, or AAV12, or the like. In further embodiments, the rAAV particle comprises capsid proteins of AAV1, AAV2, AAV3, AAV4, AAV5, AAV6, AAV7, AAV8, AAVrh8, AAVrh8R, AAV9, AAV10, AAVrh10, AAV11, or AAV12, or the like. In further embodiments, the rAAV particle comprises capsid proteins of an AAV serotype from Clades A-F (Gao, et al. *J. Virol.* 2004, 78(12):6381).

Different AAV serotypes are used to optimize transduction of particular target cells or to target specific cell types within a particular target tissue (e.g., a diseased tissue). A rAAV particle can comprise viral proteins and viral nucleic acids of the same serotype or a mixed serotype. Any combination of AAV serotypes for production of a rAAV particle is provided herein as if each combination had been expressly stated herein.

Self-Complementary AAV Viral Genomes

In some aspects, the invention provides viral particles comprising a recombinant self-complementing genome. AAV viral particles with self-complementing genomes and methods of use of self-complementing AAV genomes are described in U.S. Pat. Nos. 6,596,535; 7,125,717; 7,765,583; 7,785,888; 7,790,154; 7,846,729; 8,093,054; and 8,361,457; and Wang Z., et al., (2003) Gene Ther 10:2105-2111, each of which are incorporated herein by reference in its entirety. A rAAV comprising a self-complementing genome will quickly form a double stranded DNA molecule by virtue of its partially complementing sequences (e.g., complementing coding and non-coding strands of a transgene). In some embodiments, the invention provides an AAV viral particle comprising an AAV genome, wherein the rAAV genome comprises a first heterologous polynucleotide sequence (e.g., a therapeutic transgene coding strand) and a second heterologous polynucleotide sequence (e.g., the non-coding or antisense strand of the therapeutic transgene) wherein the first heterologous polynucleotide sequence can form intrastrand base pairs with the second polynucleotide sequence along most or all of its length. In some embodiments, the first heterologous polynucleotide sequence and a second heterologous polynucleotide sequence are linked by a sequence that facilitates intrastrand base pairing; e.g., a hairpin DNA structure. Hairpin structures are known in the art, for example in siRNA molecules. In some embodiments, the first heterologous polynucleotide sequence and a second heterologous polynucleotide sequence are linked by a mutated ITR (e.g., the right ITR). The mutated ITR comprises a deletion of the D region comprising the terminal resolution sequence. As a result, on replicating an AAV viral genome, the rep proteins will not cleave the viral genome at the mutated ITR and as such, a recombinant viral genome comprising the following in 5' to 3' order will be packaged in a viral capsid: an AAV ITR, the first heterologous polynucleotide sequence including regulatory sequences, the mutated AAV ITR, the second heterologous polynucleotide in reverse orientation to the first heterologous polynucleotide and a third AAV ITR.

Production of rAAV Vectors

Numerous methods are known in the art for production of rAAV vectors, including transfection, stable cell line production, and infectious hybrid virus production systems which include adenovirus-AAV hybrids, herpesvirus-AAV hybrids and baculovirus-AAV hybrids. rAAV production cultures for the production of rAAV virus particles all require; 1) suitable host cells, including, for example, human-derived cell lines such as HeLa, A549, or 293 cells, or insect-derived cell lines such as SF-9, in the case of baculovirus production systems; 2) suitable helper virus function, provided by wild-type or mutant adenovirus (such as temperature sensitive adenovirus), herpes virus, baculovirus, or a plasmid construct providing helper functions; 3) AAV rep and cap genes and gene products; 4) a transgene (such as a therapeutic transgene) flanked by at least one AAV ITR sequences; and 5) suitable media and media components to support rAAV production. Suitable media known in the art may be used for the production of rAAV vectors. These media include, without limitation, media produced by Hyclone Laboratories and JRH including Modified Eagle Medium (MEM), Dulbecco's Modified Eagle Medium (DMEM), custom formulations such as those described in U.S. Pat. No. 6,566,118, and Sf-900 II SFM media as described in U.S. Pat. No. 6,723,551, each of which is incorporated herein by reference in its entirety, particularly with respect to custom media formulations for use in production of recombinant AAV vectors.

Suitable rAAV production culture media of the present invention may be supplemented with serum or serum-derived recombinant proteins at a level of 0.5%-20% (v/v or w/v). Alternatively, as is known in the art, rAAV vectors may be produced in serum-free conditions which may also be referred to as media with no animal-derived products. One of ordinary skill in the art may appreciate that commercial or custom media designed to support production of rAAV vectors may also be supplemented with one or more cell culture components know in the art, including without limitation glucose, vitamins, amino acids, and or growth factors, in order to increase the titer of rAAV in production cultures.

rAAV production cultures can be grown under a variety of conditions (over a wide temperature range, for varying lengths of time, and the like) suitable to the particular host cell being utilized. As is known in the art, rAAV production cultures include attachment-dependent cultures which can be cultured in suitable attachment-dependent vessels such as, for example, roller bottles, hollow fiber filters, microcarriers, and packed-bed or fluidized-bed bioreactors. rAAV vector production cultures may also include suspension-adapted host cells such as HeLa, 293, and SF-9 cells which can be cultured in a variety of ways including, for example, spinner flasks, stirred tank bioreactors, and disposable systems such as the Wave bag system.

rAAV vector particles of the invention may be harvested from rAAV production cultures by lysis of the host cells of the production culture or by harvest of the spent media from the production culture, provided the cells are cultured under conditions known in the art to cause release of rAAV particles into the media from intact cells, as described more fully in U.S. Pat. No. 6,566,118). Suitable methods of lysing cells are also known in the art and include for example multiple freeze/thaw cycles, sonication, microfluidization, and treatment with chemicals, such as detergents and/or proteases.

Purification of rAAV Vectors

At harvest, rAAV production cultures of the present invention may contain one or more of the following: (1) host cell proteins; (2) host cell DNA; (3) plasmid DNA; (4) helper virus; (5) helper virus proteins; (6) helper virus DNA; and (7) media components including, for example, serum proteins, amino acids, transferrins and other low molecular weight proteins. In addition, rAAV production cultures further include rAAV particles having an AAV capsid serotype selected from the group consisting of AAV1, AAV2, AAV3, AAV4, AAV5, AAV6, AAV7, AAV8, AAVrh8, AAVrh8R, AAV9, AAV10, AAVrh10, AAV11, or AAV12, or the like.

Thus, in some embodiments, the rAAV production culture harvest is clarified to remove host cell debris. In some embodiments, the production culture harvest is clarified by filtration through a series of depth filters including, for example, a grade DOHC Millipore Millistak+ HC Pod Filter, a grade A1HC Millipore Millistak+ HC Pod Filter, and a 0.2 μm Filter Opticap XL1O Millipore Express SHC Hydrophilic Membrane filter. Clarification can also be achieved by a variety of other standard techniques known in the art, such as, centrifugation or filtration through any cellulose acetate filter of 0.2 µm or greater pore size known in the art.

In some embodiments, the rAAV production culture harvest is further treated with Benzonase® to digest any high molecular weight DNA present in the production culture. In some embodiments, the Benzonase® digestion is performed under standard conditions known in the art including, for example, a final concentration of 1-2.5 units/ml of Benzonase® at a temperature ranging from ambient to 37° C. for a period of 30 minutes to several hours.

rAAV particles may be isolated or purified using one or more of the following purification steps: centrifugation, flow-through anionic exchange filtration, tangential flow filtration (TFF) for concentrating the rAAV particles, rAAV capture by apatite chromatography, heat inactivation of helper virus, rAAV capture by hydrophobic interaction chromatography, buffer exchange by size exclusion chromatography (SEC), nanofiltration, and rAAV capture by anionic exchange chromatography. These steps may be used alone, in various combinations, or in different orders. In some embodiments, the method comprises all the steps in the order as described below. Methods to purify rAAV particles are found, for example, in U.S. Pat. Nos. 6,989,264 and 8,137,948 and WO 2010/148143.

Compositions and Delivery

Once produced, the IL17 inhibitor, or vectors (or virions) encoding the IL17 inhibitor, such as the fusions described above, will be formulated into compositions suitable for direct delivery to the eye in order to treat macular degeneration. If gene therapy is desired, compositions will comprise sufficient genetic material to produce a therapeutically effective amount of the IL17 inhibitor of interest, e.g., an amount sufficient to bind to and mediate the effects of the corresponding signal pathway, or to reduce or ameliorate symptoms of the disease state in question, or an amount sufficient to confer the desired benefit. Appropriate doses will also depend on the general condition of the subject being treated, age, the severity of the condition being treated, the mode of administration, among other factors. An appropriate effective amount can be readily determined by one of skill in the art.

Thus, a "therapeutically effective amount" will fall in a relatively broad range that can be determined through clinical trials. For example, for in vivo injection of rAAV virions, a therapeutically effective dose will be on the order of from about $10^6$ to $10^{15}$ of the recombinant virus, including $10^8$ to $10^{14}$ recombinant virus. For adenovirus-delivered fusions, a therapeutically effective dose can include about $1 \times 10^6$ plaque forming units (PFU) to $1 \times 10^{12}$ PFU, about $1 \times 10^7$ PFU to about $1 \times 10^{10}$ PFU, or any dose within these ranges which is sufficient to provide the desired effect.

For in vitro transduction, an effective amount of rAAV virions to be delivered to cells can be on the order of $10^8$ to $10^{13}$ of the recombinant virus. The amount of transduced cells in the pharmaceutical compositions can be from about $10^4$ to $10^{10}$ cells, including $10^5$ to $10^8$ cells. Other effective dosages can be readily established by one of ordinary skill in the art through routine trials establishing dose response curves.

In embodiments, from 1 µl to 1 ml of composition will be delivered, such as from 0.01 to about 0.5 ml, for example about 0.05 to about 0.3 ml, such as 0.08, 0.09, 0.1, 0.2, etc. and any number within these ranges, of composition will be delivered.

For protein administration, dosage amounts may vary from about 10 ng/kg to up to 100 mg/kg of body weight or more per day, including about 1 µg/kg/day to 10 mg/kg/day, depending upon the route of administration. Guidance as to particular dosages and methods of delivery is provided in the literature; see, for example, U.S. Pat. No. 4,657,760; 5,206,344; or 5,225,212.

In aspects, the compositions will also contain opthalmalogically acceptable excipients. The compositions can be formulated as solutions, gels, ointments, suspensions, a dry powder to be reconstituted with a vehicle before use, or as other suitable and well-tolerated ophthalmic delivery systems. Such excipients include any pharmaceutical agent suitable for direct delivery to the eye which may be administered without undue toxicity. Pharmaceutically acceptable excipients include, but are not limited to, sorbitol, any of the various TWEEN compounds, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

Administration can be effected in one dose, continuously or intermittently throughout the course of treatment. Methods of determining the most effective means of administration are well known to those of skill in the art and will vary with the vector, the composition of the therapy, the target cells, and the subject being treated. Single and multiple administrations can be carried out with the dose level and pattern being selected by the treating physician.

If multiple doses are administered, the first formulation administered can be the same or different than the subsequent formulations. Thus, for example, the first administration can be in the form of an adenovirus vector and the second administration in the form of an AAV virion, plasmid DNA, an AAV virion, a subunit vaccine composition, or the like. Moreover, subsequent delivery can also be the same or different than the second mode of delivery.

It should be understood that more than one transgene can be expressed by the delivered recombinant vector. Alternatively, separate vectors, each expressing one or more different transgenes, can also be delivered to the subject as described herein. Thus, multiple transgenes can be delivered concurrently or sequentially. Furthermore, it is also intended that the vectors delivered by the methods of the present invention be combined with other suitable compositions and therapies. For instance, other compounds for treating macular degeneration can be present.

As explained above, for delivery of the IL17 inhibitor to the eye (whether via gene therapy or protein therapy), administration will typically be local. This has the advantage of limiting the amount of material (protein or DNA) that needs to be administered and limiting systemic side-effects. Many possible modes of delivery can be used, including, but not limited to: topical administration on the cornea by a gene gun; subconjunctival injection, intracameral injection, via eye drops to the cornea, injection into the anterior chamber via the temporal limbus, intrastromal injection, corneal application combined with electrical pulses, intracorneal injection, subretinal injection, intravitreal injection (e.g., front, mid or back vitreal injection), and intraocular injection. Alternatively cells can be transfected or transduced ex vivo and delivered by intraocular implantation. See, Auricchio, *Mol. Ther.* (2002) 6:490-494; Bennett, *Nature Med.*

(1996) 2:649-654, 1996; Borras, *Experimental Eye Research* (2003) 76:643-652; Chaum, *Survey of Ophthalmology* (2002) 47:449-469; Campochiaro, *Expert Opinions in Biological Therapy* (2002) 2:537-544; Lai, *Gene Therapy* (2002) 9:804 813; Pleyer, *Progress in Retinal and Eye Research* (2003) 22:277-293.

Thus, the ophthalmic formulations are administered in any form suitable for ocular drug administration, e.g., dosage forms suitable for topical administration, a solution or suspension for administration as eye drops, eye washes, by injection, ointment, gel, liposomal dispersion, colloidal microparticle suspension, or the like, or in an ocular insert, e.g., in an optionally biodegradable controlled release polymeric matrix. The ocular insert is implanted in the conjunctiva, sclera, pars plana, anterior segment, or posterior segment of the eye. Implants provide for controlled release of the formulation to the ocular surface, typically sustained release over an extended time period. Additionally, in embodiments, the formulation is entirely composed of components that are naturally occurring and/or as GRAS ("Generally Regarded as Safe") by the U.S. Food and Drug Administration.

Combinations of protein and nucleic acid treatments can be used. For example, a fusion protein according to the invention can be administered to a patient. If a favorable response is observed, then a nucleic acid molecule encoding the fusion protein can be administered for a long term effect. Alternatively, the protein and nucleic acid can be administered simultaneously or approximately simultaneously.

Dosage treatment may be a single dose schedule or a multiple dose schedule. Moreover, the subject may be administered as many doses as appropriate. One of skill in the art can readily determine an appropriate number of doses.

In aspects, the compositions described herein are used in any of the methods described herein.

Kits of the Invention

The invention also provides kits. In certain embodiments, the kits of the invention comprise one or more containers comprising a purified interleukin receptor, fusions comprising the same (e.g., immunoglobulin fusions), recombinant vectors encoding the same, or AAV virions/rAAV vectors encoding the same. within embodiments, the kits contain an opthalmalogically acceptable excipients. The kits can also comprise delivery devices suitable for ocular delivery. The kits may further comprise a suitable set of instructions, generally written instructions, relating to the use of the kit and its contents for any of the methods described herein.

The kits may comprise the components in any convenient, appropriate packaging. For example, if the nucleic acid, protein, vector, or virion is provided as a dry formulation (e.g., freeze dried or a dry powder), a vial with a resilient stopper can be normally used, so that the vectors may be resuspended by injecting fluid through the resilient stopper. Ampules with non-resilient, removable closures (e.g., sealed glass) or resilient stoppers acan be used for liquid formulations. Also contemplated are packages for use in combination with a specific device.

The instructions generally include information as to dosage, dosing schedule, and route of administration for the intended method of use. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also contemplated.

2. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Materials and Methods

Human Tissue.

Human tissue was obtained from the NIH clinical center, Johns Hopkins Wilmer Institute, and Minnesota Eye Bank.

Cells and Culture.

ARPE-19 and COS-7 cells (ATCC) were used in these examples. ARPE-19 cells were cultured at 37° C. with 5% $CO_2$ in 10% Fetal Bovine Serum (FBS) DMEM/F12 Ham's (Invitrogen) supplemented with 1% 2 mM L-glutamine/100 U/ml penicillin/0.1 mg/ml streptomycin (Sigma). COS-7 cells were cultured similarly except in FBS/DMEM. Cells were trypsinized every 2-3 days through passage 20, at which point they were reseeded from frozen stocks. Cells were serum-starved in media without antibiotics for 24 h and treated for 48 h with recombinant IL17A or IL17F (R&D Systems), or 45 minutes with 0.4 mM $H_2O_2$.

Animals.

$Ccl2^{-/-}/Cx3cr1^{-/-}/Crb1^{rd8}$ mice were generated from the C57BL/6N background, recently found to be homozygous for the rd8 allele (Mattapallil et al., *Invest Ophthalmol Vis Sci.* (2012) 53:2921-2927). Two independent experiments on a total of 40 DKO/rd8 mice involved AAV2.sIL17R injection into right eyes with $1.0 \times 10^9$ DNase-Resistant Particles (DRPs) produced as described below, and AAV2.EV into left eyes ($1.0 \times 10^9$ DRPs) to serve as a vector control. Six mice received the same injections and were used for western blots.

Soluble Vector Construction and Characterization.

Figure 4:
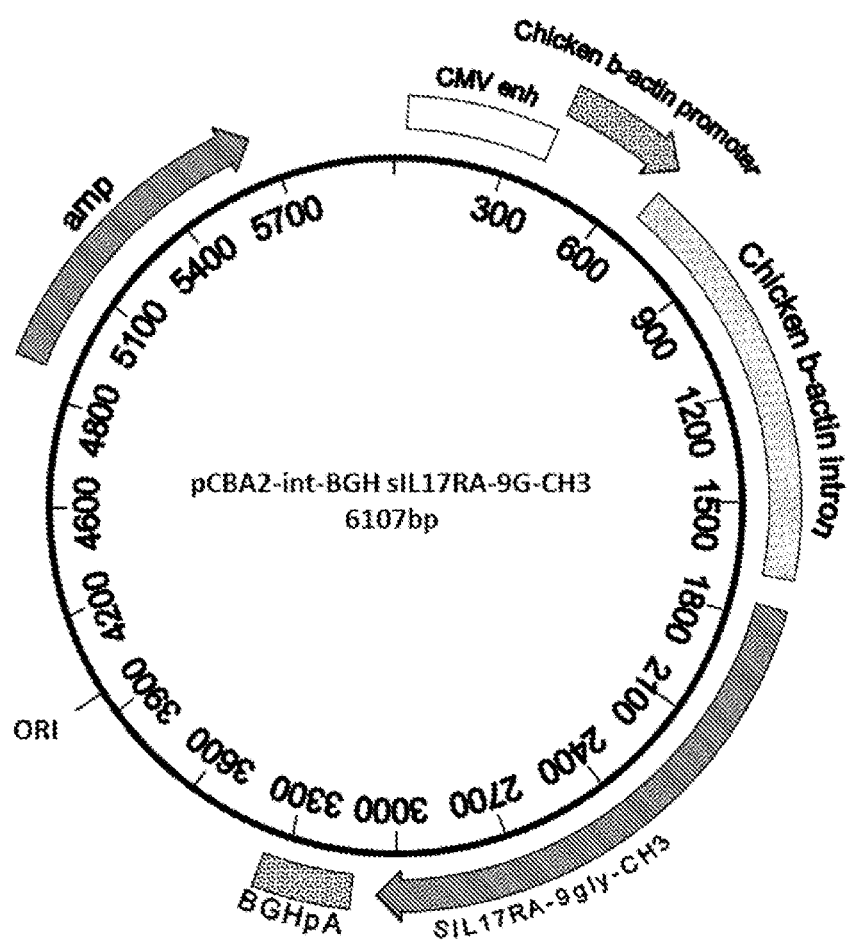
FIG. 4 is a diagram of plasmid pCBA2-int-BGH sIL17R-9G-CH3.

A soluble receptor containing the extracellular domain of the human IL-17 receptor was cloned in-frame to a 9-Gly linker followed by the CH3 region of human IgG1 driven using the chicken β-actin promoter and CMV enhancer. Plasmid pCBA2-int-BGH sIL17R-9G-CH3 is depicted in FIG. 4.

The final IL-17r fusion is shown in FIG. 2 and the nucleotide and amino acid sequences are presented in FIGS. 3A-3B (SEQ ID NOS:3 and 4). As shown in FIG. 2, the IL-17r construct encodes a soluble IL-17r, including amino acids 1 to 317 of human IL-17r, linked by a sequence of nine glycines to the CH3 domain, amino acids 225 to 330 of the human IgG1 C region. The constructs were prepared and incorporated into rAAV virions as follows.

Soluble IL17R/9gly/CH3 was cloned into plasmid pCBA2 (Xu et al., *Hum Gene Ther* (2001) 12:563-573) which contains hybrid chicken beta-actin (CBA) promoter and bovine growth hormone polyadenylation signal sequence (BGH poly A). The expression cassette was transferred to pre-viral plasmid vector pAAVSP70 containing AAV2 inverted terminal repeats (Ziegler et al., *Mol Ther* (2004) 9:231-240). The recombinant vector AAV2.sIL17R was produced by triple transfection of 293 cells with pAAVSP70.sIL17R and helper plasmids p5repΔCMVcap (Vincent et al., *J Virol* (1997) 71:1897-1905) and pHelper (Stratagene, La Jolla, Calif., USA). In the empty vector (AAV2.EV), a 3.8 kb intron from alpha-1-antitrypsin replaced sIL17R. Vectors were purified from cell lysates with an iodixanol step gradient and HiTrap Heparin column (GE Healthcare Life Sciences, Piscataway, N.J., USA) on an ÄKTA FPLC system (GE Healthcare Life Sciences, Piscataway, N.J.) (Vincent et al., *J Virol* (1997) 71:1897-1905; Zolotukhin et al., *Methods* (2002) 28:158-167. Viral vector titers were determined using a TaqMan RT-PCR assay (ABI Prism 7700; Applied Biosystems, Foster City, Calif., USA) with primers specific for BGH poly A.

For sIL17R binding to IL17A, ELISA plates were coated with 100 μg/ml human IL17A or mouse IL17A overnight, then blocked with 1% BSA. Serial two-fold dilutions of sIL17R were added in triplicate to the plate and incubated for 1 h at 37° C. Unbound receptor was washed from the plate in an ELISA plate washer. 100 μl biotinylated anti-IL17RA (1 μg/ml) was added to each well and incubated 1 h at room temperature and excess antibody was washed away. Each well was incubated with streptavidin-HRP conjugate and washed. Bound HRP was measured by incubation with TMBD substrate for 20 minutes followed by addition of acid stop solution. OD was measured at 450 nm.

Figure 5A:
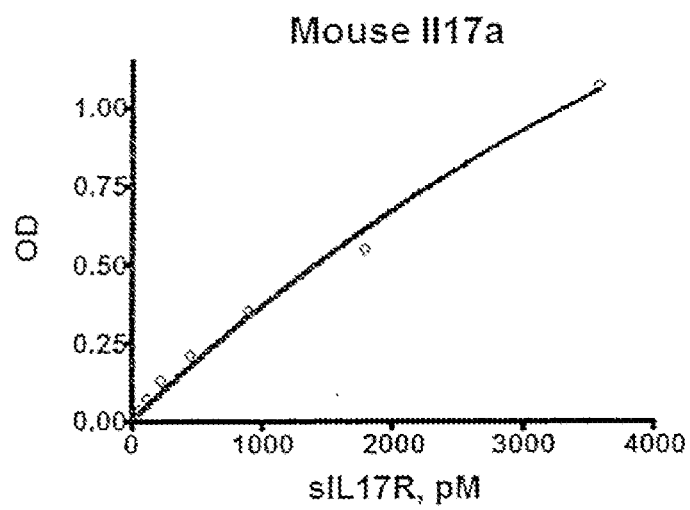
FIGS. 5A and 5B show binding of sIL17R to mouse (FIG. 5A) and human (5B) IL17A. Binding is presented as pM concentration of sIL17R vs. OD absorbance.
Figure 5B:
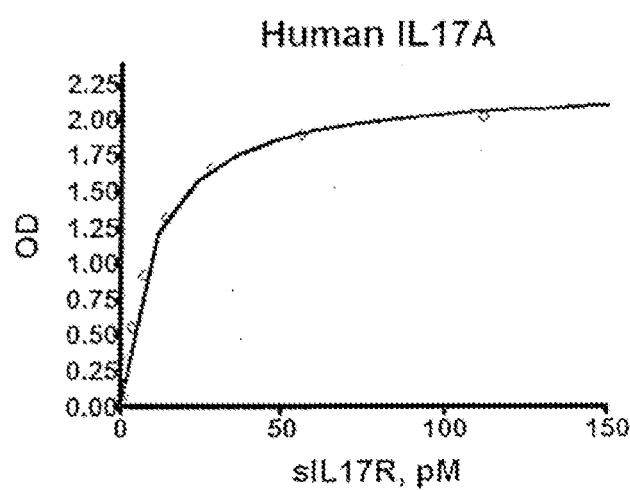

As shown in FIGS. 5A and 5B, the receptor bound to both human and mouse IL17A.

Quantitative Reverse-Transcriptase PCR (qRT-PCR).

Paraffin-embedded human ocular sections were microdissected. Cells were lysed and RNA was extracted using the Paradise RNA isolation kit (Applied Biosystems). For ARPE-19 cells, COS-7 cells, and DKO/rd8 retinas, total RNA was extracted using Trizol (Qiagen) and chloroform/isopentanol. cDNA was made with the SuperScript II kit (Invitrogen). SYBR Green (Qiagen) primers were used for human IL17A, human IL17RC, mouse Il17a, and mouse Il17rc. The TaqMan Gene expression assay (Applied Biosystems) was used for human IL8 and mouse Il6. Expression fold-change was calculated by $2^{-\Delta\Delta CT}$.

Detecting sIL17R in Mouse Retinas by ELISA.

Eyes were removed from euthanized mice and stored at −70° C. until the assay. The vitreous humor and the retinas were dissected from frozen eyes and homogenized in 200 μL of lysis buffer provided in the ELISA kit. Undiluted homogenates were clarified by centrifugation and assayed for IL17R levels using the human IL17R Duoset kit (R&D Systems).

MTT Assay.

ARPE-19 or COS-7 cells were plated in quadruplicate on 96-well plates ($2 \times 10^4$ cells/well) in 10% FBS and incubated at 37° C. and 5% $CO_2$ for 24 h. Cells were washed in PBS and serum-starved for 24 h, then treated for 48 h with serial 1:10 dilutions of IL17A or IL17F. Cells were incubated 4 h in 0.5 mg/ml MTT dissolved in DMEM/F12. Following aspiration, DMSO was added and plates placed on a shaker for 20 min in the dark. Absorption was measured at 570 nm (Synergy II plate reader; GenS software; BioTek) and normalized to that of untreated cells.

Confocal Microscopy.

Cells or frozen mouse eye sections were fixed in 4% paraformaldehyde for 15 min, washed in PBS, and blocked in ICC buffer with 5% goat or rabbit serum for 30 min at 4° C. Primary antibody incubation occurred overnight at 4° C. Secondary antibody incubation lasted 1 h at room temperature and slides were mounted in Vectashield fluorescent media (Vector Labs) and stored at 4° C. in the dark until imaged with an Olympus FV1000 Confocal Scanning Scope. Primary antibodies included Cleaved Caspase-3 (Cell Signaling Technology, 1:200), Cleaved Caspase-9 (Santa Cruz, 1:100), and NF-κB p65 (Cell Signaling Technology, 1:50). Secondary antibodies included goat anti-rabbit IgG (1:400), rabbit anti-goat IgG (1:400), and rabbit anti-mouse IgG (1:400). DAPI (1:1000) marked nuclei.

Mouse Fundoscopy and Clinical Grading.

Fundoscopy was performed before injection and 2 months post-injection. An endoscope with parallel illumination and observation channels was connected to a Nikon D90 digital camera. Mice received intraperitoneal injection of ketamine (1.4 mg/mouse) and xylazine (0.12 mg/mouse) for systemic anesthesia and topical 1% tropicamide ophthalmic solution (Alcon Inc, Fort Worth, Tex.) for pupil dilation.

A masked observer assigned lesion grades as follows by comparing the same fundus area over the 2-month course:

TABLE 1

| | | |
|---|---|---|
| Progression | +1 | >10% increase in retinal lesion number |
| | +2 | >50% increase in size of ≥1/3 of lesions |
| | +3 | >5 fused lesions or appearance of >2 chorioretinal scars |
| | +4 | diffuse chorioretinal scars |
| Regression | −1 | >10% decrease in retinal lesion number |
| | −2 | >50% decrease in sizeof ≥1/3 of lesions |
| | −3 | >50% disappearance of retinal lesions |
| | −4 | total disappearance of retinal lesions |

A2E Extraction and Quantification.

A2E was extracted with chloroform/methanol as previously described (Karan et al, *Proc. Natl. Acad. Sci. USA* (2005) 102:4164-4169. Briefly, A2E ([2,6-dimethyl-8-(2,6,6-trimethyl-1-cyclohexen-1-yl)-1E,3E,5E,7E-octatetraenyl]-1-(2-hydroxyethyl)-4-[4-methyl-6(2,6,6-trimethyl-1-cyclohexen-1-yl) 1E,3E,5E,7E-hexatrienyl]-pyridinium) detection and quantification was performed by liquid-chromatography mass spectrometry using a QTRAP 2000 linear ion trap tandem mass spectrometer (Applied Biosystems/MDS SCIEX, Concord, Ontario, Canada) with an Agilent 1100 LC system (Agilent, Wilmington, Del.). A gradient of 80% to 98% methanol was used to separate A2E on a C18 column (Zorbax; Agilent) at a flow-rate of 0.3 ml/min. A2E was quantified using external A2E standards.

Histopathology.

For bright field microscopy, eyes were fixed for 30 min in 4% gluteraldehyde followed by 10% formalin for 1 h. They were next embedded in methacrylate and serially sectioned in the vertical pupillary-optic nerve plane. Each eye was sectioned 4 times, stained with hematoxylin and eosin, and analyzed by bright field microscopy. For transmission electron microscopy, mouse eyes were fixed in 2.5% gluteraldehyde and 0.5% osmium tetroxide, dehydrated, and embedded into Spurr's epoxy resin. 90 nm sections were made and double-stained with uranyl acetate and lead citrate, and viewed using a JEOL JEM 1010 transmission electron microscope.

Western Blot Detection of Ex Vivo Signal Transduction.

Phosphorylation of Erk1/2, p38, and Akt was measured following stimulation with recombinant mouse Il17a in neuroretinas having previously received AAV2.sIL17R or AAV2.EV as follows. Two weeks after AAV2.sIL17R and AAV2.EV injection, neuroretinas from six mice were isolated and cultured 2 h ex vivo at 37° C. and 5% $CO_2$ in 1% BSA in PBS. Neuroretinas were treated with 50 ng/ml recombinant mouse Il17a (R&D Systems) for 0, 5, or 15 min. Protein lysates were isolated in RIPA and complete protein lysis buffer, homogenized using a P200 pipette, and kept on ice 30 min with occasional vortexing. Following centrifugation (16,000 rpm, 30 min, 4° C.), protein concentration was measured using the BCA assay (Pierce). 10% polyacrylamide gels (Invitrogen) were loaded with 10 μg protein/lane and ran at 125 V for 1 h. Transfer was performed onto a nitrocellulose membrane (Invitrogen) at 300 mA for 1 h at 4° C. Membranes were blocked in 5% BSA for 1 h and incubated with primary antibody overnight at 4° C. on a shaker. Primary antibodies included phospho- and total-Erk1/2, phospho- and total-Akt, phospho- and total-p38, and GAPDH (Cell Signaling Technology). Membranes were incubated with the secondary antibody goat anti-rabbit conjugated to HRP (1:10,000) for 45 min at room temperature. Membranes were exposed using SuperSignal West Dura (Pierce).

Statistics.

Cell and patient qRT-PCR data was evaluated using the unpaired t-test. For mouse qRT-PCR, clinical fundus scores, and A2E, the paired t-test. P<0.05 determined statistical significance.

Example 1

Ocular Changes in IL17A and IL17RC Gene Expression Due to AMD.IL17A

Ocular changes in IL17A and IL17RC gene expression due to AMD.IL17A was investigated in the choroidal button and the macula, and IL17RC was examined in the macula only using the methods described above. Both choroids and maculae affected with GA and nAMD expressed significantly higher quantities of IL17A (FIG. 6A-6B). IL17RC transcripts were significantly elevated in GA and nAMD maculae (FIG. 6C). Increased gene expression was mirrored by intensified immunoreactivity against both IL17A and IL17RC proteins on ocular sections obtained from AMD donors in comparison to age-matched healthy donors (FIG. 6D). In contrast, IL17A was undetectable by qRT-PCR in the peripheral retina of 27 AMD and 4 normal donors. Low IL17RC was detected in 3 of 27 AMD peripheral retinas but expression was significantly less than in macular regions. IL17F, an IL17A homologue with overlapping function (Ishigame et al., *Immunity* (2009) 30:108-119), was undetectable by qRT-PCR in patient maculae. These results evidenced that macular expression of the IL17 pathway is involved in the development of AMD.

Example 2

Effects of IL17A on ARPE-19

Due to increased IL17A expression in AMD patient retinas (FIGS. 6A-6D) and its role in chronic inflammation, the effects of IL17A on ARPE-19 were studied since the death of RPE cells is believed to initiate retinal degeneration (Curcio et al, *Invest Ophthalmol. Vis. Sci.* (1996) 37:1236-1249). IL17A signal transduction was first assessed in ARPE-19 based on reports that they undergo typical IL17-related signaling (Chen et al., *Mol Vis* (2011) 17:3072-3077), such as induction of nuclear factor (NF)-κB nuclear translocation, but do not express IL17RA (Chen et al., *PLoS One* (2011) 6:e18139), a necessary component of the signal transduction machinery (Gaffen, S. L., *Nat Rev Immunol* (2009) 9:556-567). In ARPE-19, IL17RA protein was detected and both IL17RA and IL17RC constitutive expression were confirmed. Consequently, NF-κB nuclear translocation was observed (Gaffen, S. L., *Nat Rev Immunol* (2009) 9:556-567) and IL8 induction was measured upon IL17A stimulation.

Figure 7:
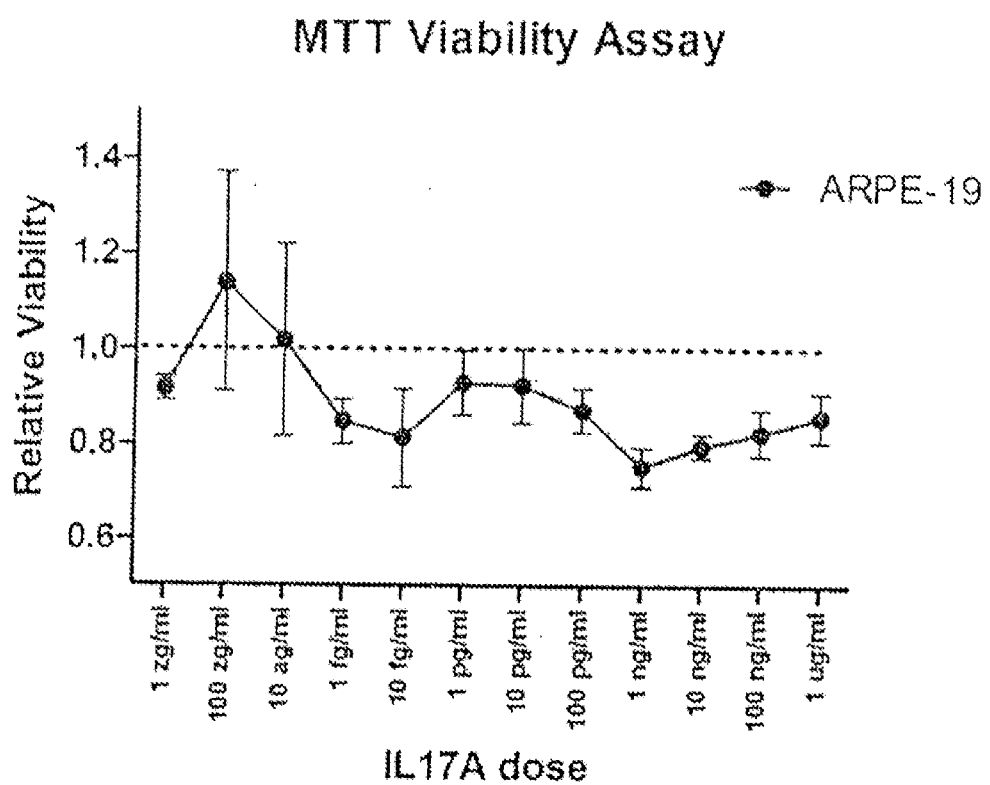
FIG. 7 shows an MTT viability assay of cells treated for 48 h with dilutions of IL17A.

To gain insight into the effect IL17A had on RPE cells, ARPE-19 cells were treated with IL17A and it was consistently noted that reductions in cell viability occurred. The MTT assay described above measured reduced cell viability via diminished activity of mitochondrial reductase (FIG. 7), suggesting that IL17A damaged mitochondria and activated apoptosis. Indeed, IL17A induced cleavage of Caspase-9 and Caspase-3 when evaluated alongside $H_2O_2$ as a positive control.

Figure 8:
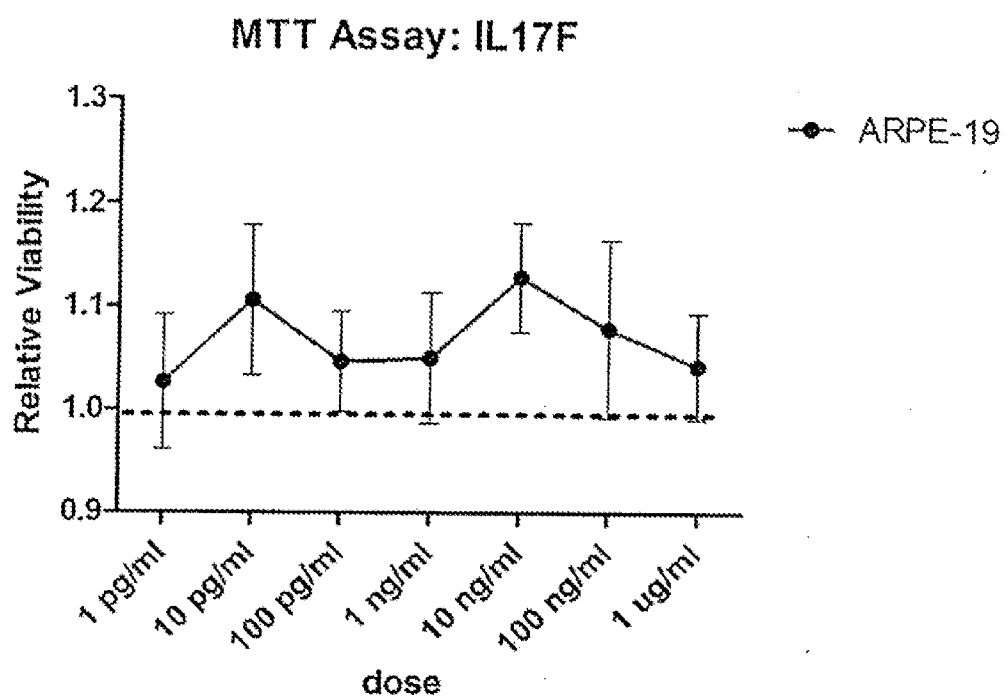
FIG. 8 shows an MTT viability assay of cells treated for 48 h with dilutions of IL17F.

To evaluate the extent of cellular damage, transmission electron microscopy to compare untreated cells to those exposed with IL17A was used. Untreated cells housed normal mitochondria, healthy cytoplasmic organelles, and intact nuclear membranes. Low-dose treatment (1 pg/ml IL17A) prompted accumulation of cytoplasmic lipid droplets. High-dose treatment (10 ng/ml IL17A) exacerbated lipid accumulation, mitochondrial damage, autophagosomes, and ultimately caused cellular degeneration and apoptosis. Lipid accumulation is reminiscent of lipofuscin accumulation observed in AMD retinas and is an early indicator of RPE degeneration, signifying an inability of the RPE to maintain intracellular homeostasis. ARPE-19 cells treated with IL17F experienced no reductions in cell viability by the MTT assay (FIG. 8) but did exhibit Caspase-3 and Caspase-9 activity. However, since only IL17A was detectable in AMD retinas, it was determined that these effects were inconsequential in the development of AMD.

Example 3

Cell-Type Specificity of IL17A Effects

Figure 9A:
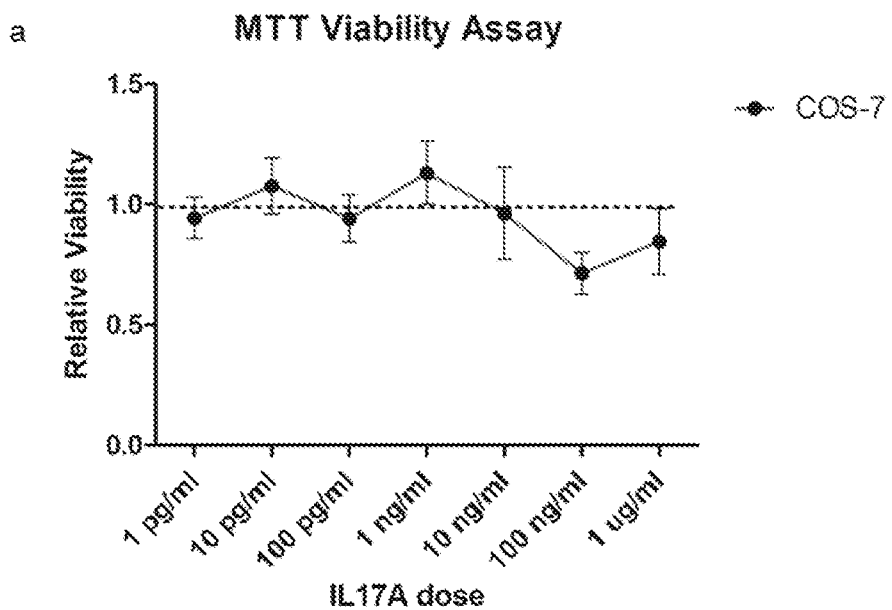
FIGS. 9A and 9B show cell-type dependent effects of IL17A.
Figure 9B:
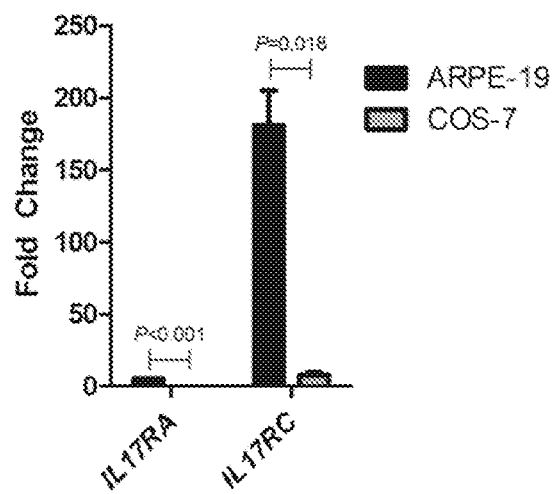

Because AMD has not been associated with any currently recognized systemic inflammatory diseases, it was hypothesized that IL17A's effects would be cell-type specific. Treatment of COS-7 with IL17A did not reduce cell viability (FIG. 9A). Thus, it was suspected that these differences arose due to lower expression of the IL17A receptors in COS-7. With qRT-PCR, it was found that COS-7 expressed lower IL17RA and IL17RC than did ARPE-19 (FIG. 9B). These data confirmed the observation that enhanced receptor expression in AMD macular tissue is likely instrumental in conferring IL17A-mediated tissue insults.

Example 4

IL17A and Photoreceptor and RPE Degeneration In Vivo

Figure 6:
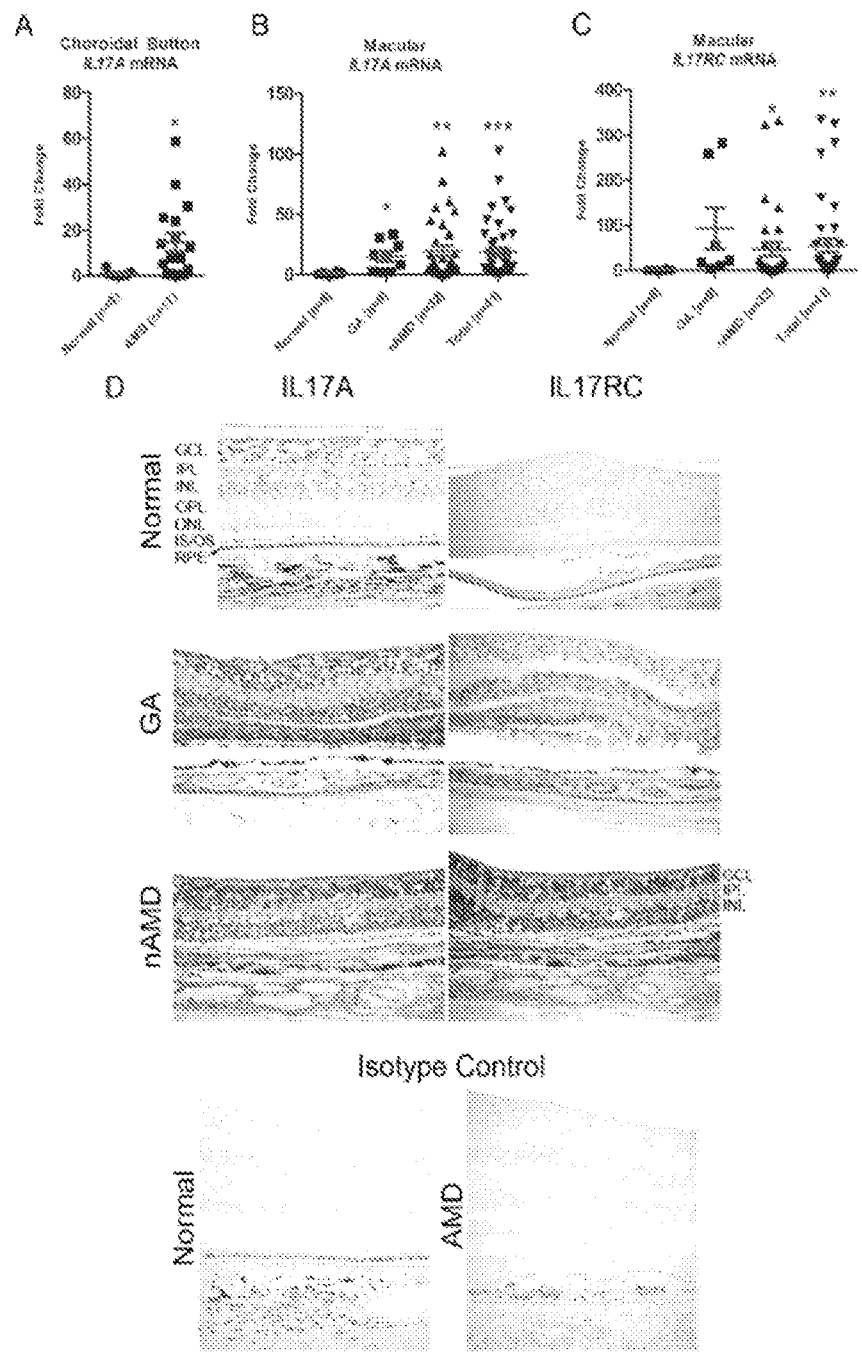
FIGS. 6A-6D show that IL17A and IL17RC are highly expressed in pathological human AMD tissue.

Given IL17A's ties to AMD and the deleterious effects seen in vitro, it was hypothesized that Il17a signaling contributed to photoreceptor and RPE degeneration in DKO/rd8 mice. Retinal Il17a expression increased linearly with age in wild-type mice (C57BL/6N and C57BL/6J strains), though DKO/rd8 showed significantly greater increases (FIG. 10A), mirroring the pattern measured in AMD patients (FIG. 6). To attribute the increase in Il17a expression to Ccl2 and Cx3cr1 double deficiency and not to the rd8 allele in the C57BL/6N strain used to generate DKO/rd8 (Mattapallil et al., *Invest Ophthalmol Vis Sci.* (2012) 53:2921-2927), retinal Il17a expression in 2-month-old DKO/rd8 was compared with that in age-matched C57BL/6N and much higher expression was found in DKO/rd8 (FIG. 11). These data suggested that a homologous immunopathological mechanism drove photoreceptor and RPE pathology in both humans with AMD and DKO/rd8 mice.

Figure 12:
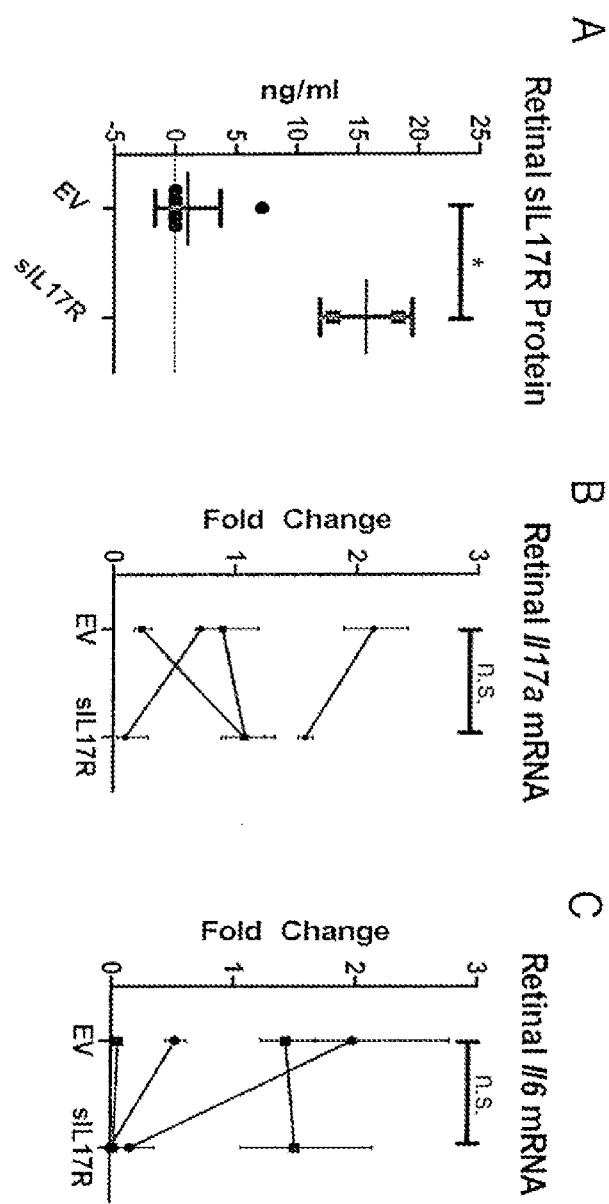
FIGS. 12A-12C show the detection of sIL17R in the retina.

To inhibit Il17a signaling in the DKO/rd8 retina, intravitreal injections were administered to 40 mice in 2 independent trials using the AAV2 vector encoding soluble IL17 receptor, prepared as described above (sIL17R, FIG. 5). The vector encoding sIL17R was injected into the right eyes and an empty vector (EV) into left eyes. Two months post-injection, eyes were evaluated in vivo fundoscopically and then ex vivo histologically and biochemically. In AAV2.sIL17R versus AAV2.EV receiving eyes, significantly higher sIL17R protein was detected, and no change in Ill 7a retinal mRNA expression was measured. A non-significant reduction in IL6 was also observed (FIGS. 12A-12C). Taken together, this showed that there was sIL17R expression in AAV2.sIL17R- but not in AAV2.EV-receiving eyes.

Figure 10:
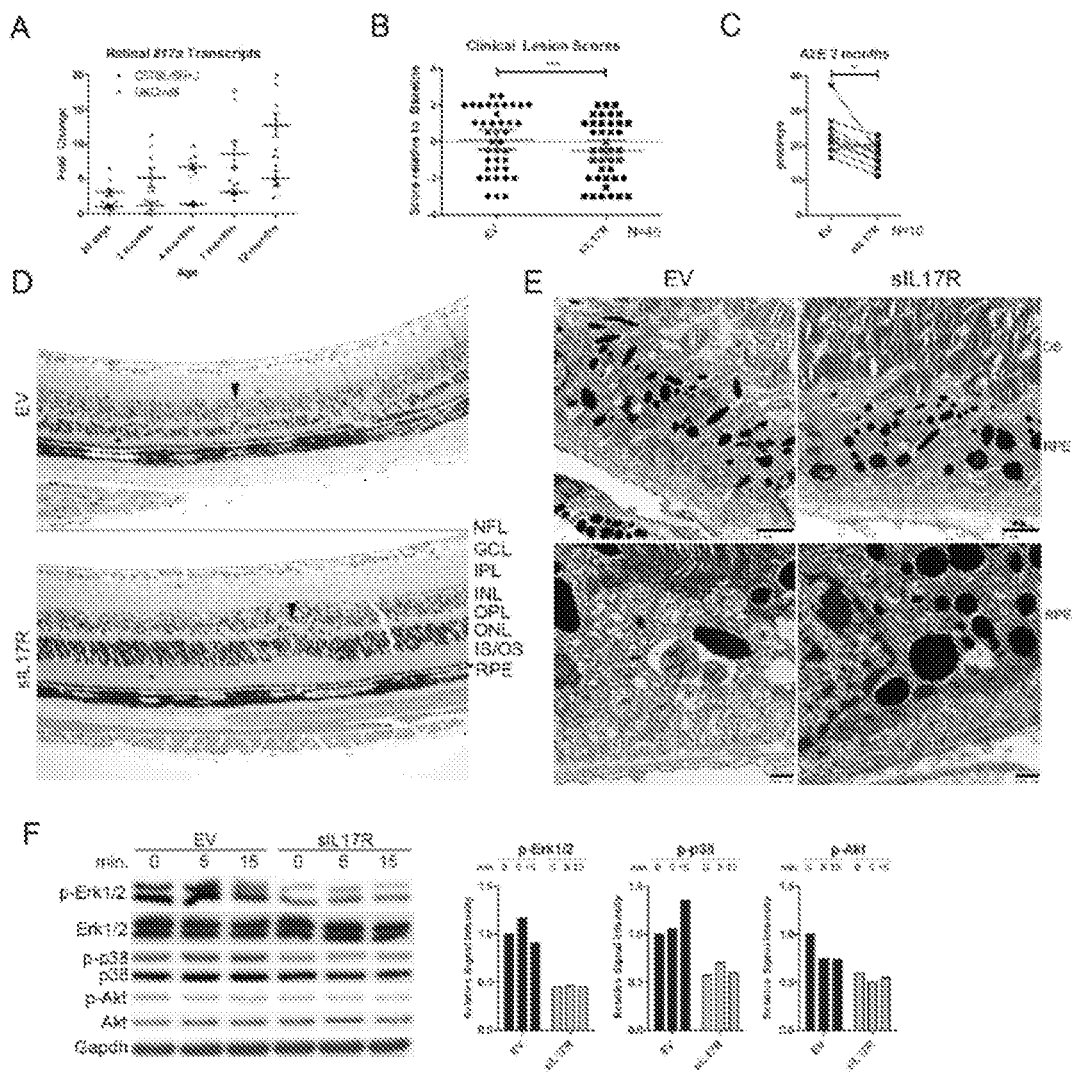
FIGS. 10A-10F show that IL17A knockdown significantly ameliorates AMD-like lesions.
Figure 11:
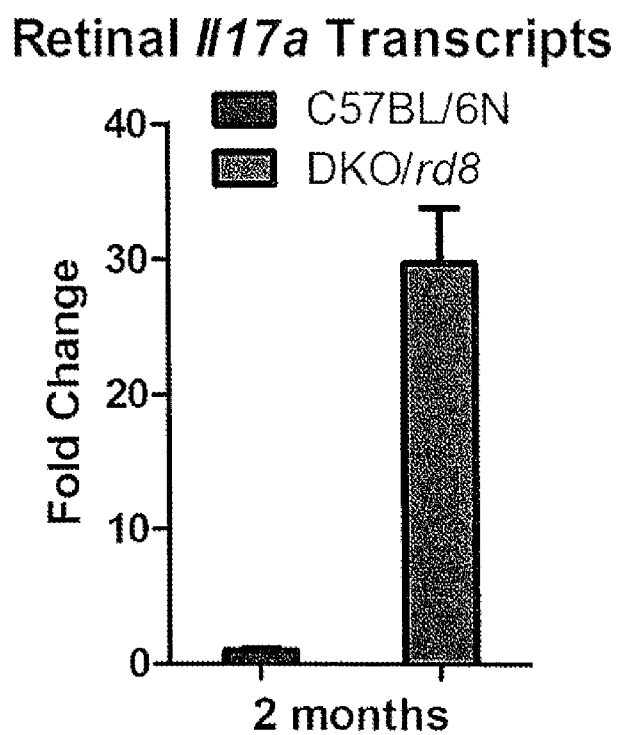
FIG. 11 shows higher Il17a expression in DKO/rd8 over C57BL/6N retinas at 2 months of age. 6 retinas were used from 3 mice of each strain.
Figure 13:
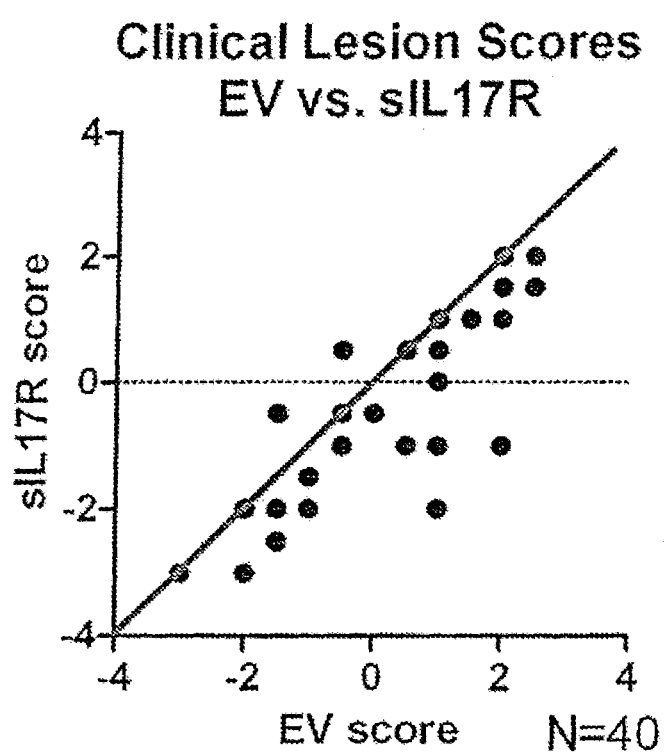
FIG. 13 shows an intra-mouse pairwise comparison of lesion scores, empty vector (EV) versus sIL17R (80 eyes total from 40 mice); all points to the right of the diagonal line indicate that the sIL17R-treated eye fared better than its contralateral counterpart.

Clinically, sIL17R retinas showed significant improvement over their EV counterparts (FIG. 10B and FIG. 13). The sIL17R treatment significantly reduced the concentration of the lipofuscin fluorophore A2E (FIG. 10C), a byproduct from the visual cycle flux of all-trans-retinal and a biomarker of RPE stress (Ben-Shabat et al., *Bioorg. Med. Chem. Lett.* (2001) 11:1533-1540. Histopathologically, EV retinas experienced AMD-like IS/OS/RPE degenerative lesions and rd8ONL dystrophic lesions, whereas sIL17R treatment prevented IS/OS/RPE-but not rd8-associated damage (FIG. 10D). Ultrastructural analysis revealed the presence of lipofuscin and glycogen deposits throughout EV RPE, neither of which was seen in significant quantity in sIL17R eyes (FIG. 10E). This finding paralleled the measured reduction in retinal A2E concentration and indicated overall healthier RPE. Severe damage to RPE and mitochondria was seen only in EV and not in sIL17R eyes (FIG. 10E). These data are consistent with previous work suggesting that anti-inflammatory therapy is effective in DKO/rd8 due to down regulation of retinal Il17a (Tuo et al., *J Neuroinflammation* (2012) 9:59.

Example 5

Signal Transduction Alterations

Alterations in signal transduction were evaluated in order to identify a mechanism of action. In human adipocytes, IL17A induces phosphorylation of Akt and Erk1/2 (Zuniga et al, *J Immunol* (2010) 185:6947-6959), whereas in ARPE-19 the cytokine activates Erk1/2, p38, Akt, and NF-κB (Chen et al., *Mol Vis* (2011) 17:3072-3077). MAPK and Akt phosphorylation was analyzed ex vivo using lysates extracted from EV- or sIL17R-expressing DKO/rd8 neuroretina that were stimulated with recombinant mouse Il17a (FIG. 10F). There was a reduction in background MAPK (Erk1/2 and p38) as well as in Akt phosphorylation in sIL17R versus EV retinas, though sIL17R inhibited activation of only Erk1/2 and p38. Since Akt was not induced in EV neuroretinas, it was concluded that it had no direct input from Il17a. NF-κB nuclear translocation was evaluated in EV versus sIL17R retinas but no signal was detected by confocal microscopy. While these data do not exclude NF-κB involvement, they suggest a MAPK-dependent mechanism in focal retinal degeneration. Recently, enhanced ERK1/2 phosphorylation was noted in GA AMD tissue and Erk1/2 inhibition rescued RPE degeneration in a mouse model (Dridi et al., *Proc Natl Acad Sci USA* (2012) 109:13781-13786).

Figure 14A:
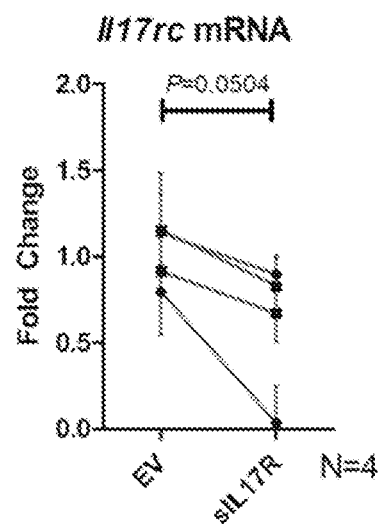
FIGS. 14A and 14B show lower Il17rc transcript expression in sIL17R verses EV retinas 2 months post-injection.
Figure 14B:
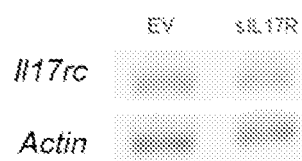

Interestingly, a reduction in Il17rc retinal expression was measured (FIGS. 14A and 14B). This finding further indicated a correlation between Il17rc and retinal degeneration, consistent with our patient data. However, treatment of ARPE-19 with IL17A did not induce IL17RC expression in vitro. Thus, IL17RC may have either a causative role in AMD or focal retinal degeneration, or it may be a biomarker of disease.

In sum, the inventors have demonstrated that IL17A contributes towards retinal pathology. As IL17A signal blockade effectively arrested photoreceptor and RPE degeneration via a MAPK-dependent pathway in DKO/rd8 mice, it was determined that IL17A signaling directly mediates focal retinal degeneration and is therefore a therapeutic target for treatment of AMD progression.

Thus, methods for treating macular degeneration, as well as compositions comprising IL17r-immunoglobulin fusions, are described. Although exemplary embodiments of the subject invention have been described in some detail, it is understood that obvious variations can be made without departing from the spirit and the scope of the invention as defined herein.

The invention claimed is:

1. A method of treating or reducing age-related macular degeneration (AMD) in a mammalian subject comprising intravitreally administering to the diseased eye of the subject a composition comprising a recombinant viral vector encoding a fusion protein comprising an IL17 inhibitor and a multimerization domain, wherein the IL17 inhibitor is a soluble IL17A receptor capable of binding and modulating the activity of IL17A, wherein the recombinant viral vector is a recombinant adeno-associated virus serotype 2 (rAAV2) virion.

2. The method of claim 1, wherein the composition further comprises an opthalmalogically acceptable vehicle.

3. The method of claim 1, wherein the multimerization domain is derived from an immunoglobulin (Ig) heavy chain.

4. The method of claim 1, wherein the multimerization domain is derived from an immunoglobulin (Ig) constant region.

5. The method of claim 1, wherein the multimerization domain is derived from the Fc region of an immunoglobulin (Ig).

6. The method of claim 1, wherein the multimerization domain comprises the CH3 of an immunoglobulin (Ig).

7. The method of claim 1, wherein the multimerization domain is derived from an IgG1, an IgG2, an IgG3 or an IgG4.

8. The method of claim 1, wherein the multimerization domain is from the constant region of an IgG1 heavy chain.

9. The method of claim 1, wherein when the fusion protein is expressed, a multimer of the fusion protein is produced.

10. The method of claim 1, wherein the recombinant vector encodes a fusion protein comprising:
    (a) an IL17A receptor; and
    (b) an immunoglobulin constant region multimerization domain,
    wherein when the fusion protein is expressed, a multimer of the fusion protein is produced.

11. The method of claim 10, wherein the multimerization domain comprises the CH3 domain of an IgG, or an active fragment thereof.

12. The method of claim 10, wherein the multimerization domain is from an IgG1, an IgG2, an IgG3 or an IgG4.

13. The method of claim 10, wherein the multimerization domain is from the constant region of an IgG1 heavy chain.

14. The method of claim 10, wherein the multimer is a homodimer.

15. The method of claim 10, wherein the fusion protein comprises the amino acid sequence of FIG. 3B (SEQ ID NO:4), or an active variant thereof having at least 90% sequence identity to the sequence of FIG. 3B (SEQ ID NO:4).

16. The rAAV virion contains an AAV2 serotype capsid and an AAV2 ITR.

* * * * *

UNITED STATES PATENT AND TRADEMARK OFFICE
CERTIFICATE OF CORRECTION

PATENT NO. : 10,640,771 B2
APPLICATION NO. : 14/785159
DATED : May 5, 2020
INVENTOR(S) : Samuel Wadsworth et al.

It is certified that error appears in the above-identified patent and that said Letters Patent is hereby corrected as shown below:

On the Title Page

Item (73), Lines 2-4 the Assignee:
Please change "THE UNITED STATES OF AMERICA AS REPRESENTED BY THE, Rockville, MD (US)" with --THE UNITED STATES OF AMERICA AS REPRESENTED BY THE SECRETARY, DEPARTMENT OF HEALTH AND HUMAN SERVICES, Bethesda, MD (US)--.

Signed and Sealed this
Fourth Day of August, 2020

Andrei Iancu
*Director of the United States Patent and Trademark Office*

SEQUENCE LISTING

<160> NUMBER OF SEQ ID NOS: 13

<210> SEQ ID NO 1
<211> LENGTH: 2601
<212> TYPE: DNA
<213> ORGANISM: Homo sapiens

<400> SEQUENCE: 1

```
atggggccg cacgcagccc gccgtccgct gtcccggggc ccctgctggg gctgctcctg        60
ctgctcctgg gcgtgctggc cccgggtggc gcctccctgc gactcctgga ccaccgggcg       120
ctggtctgct cccagccggg gctaaactgc acggtcaaga atagtacctg cctggatgac       180
agctggattc accctcgaaa cctgaccccc tcctcccaa aggacctgca gatccagctg       240
cactttgccc acacccaaca aggagacctg ttccccgtgg ctcacatcga atggacactg       300
cagacagacg ccagcatcct gtacctcgag ggtgcagagt tatctgtcct gcagctgaac       360
accaatgaac gtttgtgcgt caggtttgag tttctgtcca aactgaggca tcaccacagg       420
cggtggcgtt ttacccttcag ccactttgtg gttgaccctg accaggaata tgaggtgacc       480
```

```
gttcaccacc tgcccaagcc catccctgat ggggacccaa accaccagtc caagaatttc    540
cttgtgcctg actgtgagca cgccaggatg aaggtaacca cgccatgcat gagctcaggc    600
agcctgtggg accccaacat caccgtggag acctggagg cccaccagct gcgtgtgagc     660
ttcaccctgt ggaacgaatc tacccattac cagatcctgc tgaccagttt tccgcacatg    720
gagaaccaca gttgctttga gcacatgcac cacatacctg cgcccagacc agaagagttc    780
caccagcgat ccaacgtcac actcactcta cgcaaccta aagggtgctg tcgccaccaa     840
gtgcagatcc agcccttctt cagcagctgc ctcaatgact gcctcagaca ctccgcgact    900
gtttcctgcc cagaaatgcc agacactcca gaaccaattc cggactacat gcccctgtgg    960
gtgtactggt tcatcacggg catctccatc ctgctggtgg gctccgtcat cctgctcatc   1020
gtctgcatga cctggaggct agctgggcct ggaagtgaaa aatacagtga tgacaccaaa   1080
tacaccgatg gcctgcctgc ggctgacctg atccccccac cgctgaagcc caggaaggtc   1140
tggatcatct actcagccga ccacccctc tacgtggacg tggtcctgaa attcgcccag    1200
ttcctgctca ccgcctgcgg cacgaagtg gccctgacc tgctgaaga gcaggccatc      1260 tcggaggcag gagtcatgac ctgggtgggc cgtcagaagc aggagatggt ggagagcaac   1320
tctaagatca tcgtcctgtg ctcccgcggc acgcgcgcca agtggcaggc gctcctgggc   1380 cgggggcgc ctgtgcggct gcgctgcgac cacggaaagc ccgtggggga cctgttcact    1440
gcagccatga acatgatcct cccggacttc aagaggccag cctgcttcgg cacctacgta   1500
gtctgctact tcagcgaggt cagctgtgac ggcgacgtcc ccgacctgtt cggcgcggcg   1560
ccgcggtacc cgctcatgga caggttcgag gaggtgtact tccgcatcca ggacctggag   1620
atgttccagc cgggccgcat gcaccgcgta ggggagctgt cggggacaa ctacctgcgg    1680 agcccgggcg gcaggcagct ccgcgccgcc ctggacaggt tccgggactg gcaggtccgc    1740
tgtcccgact ggttcgaatg tgagaacctc tactcagcag atgaccagga tgccccgtcc   1800
ctggacgaag aggtgtttga ggagccactg ctgcctccgg aaccggcat cgtgaagcgg    1860 gcgcccctgg tgcgcgagcc tggctcccag gcctgcctgg ccatagaccc gctggtcggg   1920
gaggaaggag gagcagcagt ggcaaagctg gaacctcacc tgcagccccg ggtcagcca    1980 gcgccgcagc ccctccacac cctggtgctc gccgcagagg agggggccct ggtggccgcg   2040
gtggagcctg gcccctggc tgacggtgcc gcagtccggc tggcactggc ggggagggc    2100 gaggcctgcc cgctgctggg cagcccgggc gctgggcgaa atagcgtcct cttcctcccc   2160
gtggaccccg aggactcgcc ccttggcagc agcaccccca tggcgtctcc tgacctcctt   2220
ccagaggacg tgagggagca cctcgaaggc ttgatgctct cgctcttcga gcagagtctg   2280
agctgccagg cccagggggg ctgcagtaga cccgccatgg tcctcacaga cccacacacg   2340
ccctacgagg aggagcagcg gcagtcagtg cagtctgacc agggctacat ctccaggagc   2400
tccccgcagc ccccgagg actcacggaa atggaggaag aggaggaaga ggagcaggac    2460
ccagggaagc cggccctgcc actctctccc gaggacctgg agagcctgag gagcctccag   2520
cggcagctgc tttccgcca gctgcagaag aactcgggct gggacacgat ggggtcagag   2580 tcagagggggc ccagtgcatg a                                            2601
```

<210> SEQ ID NO 2
<211> LENGTH: 866
<212> TYPE: PRT
<213> ORGANISM: Homo sapiens

<400> SEQUENCE: 2

```
Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
                100                 105                 110

Glu Leu Ser Val Leu Gln Leu Asn Thr Asn Glu Arg Leu Cys Val Arg
            115                 120                 125

Phe Glu Phe Leu Ser Lys Leu Arg His His Arg Arg Trp Arg Phe
130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
                260                 265                 270

Leu Lys Gly Cys Cys Arg His Gln Val Gln Ile Gln Pro Phe Phe Ser
            275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320

Val Tyr Trp Phe Ile Thr Gly Ile Ser Ile Leu Leu Val Gly Ser Val
                325                 330                 335

Ile Leu Leu Ile Val Cys Met Thr Trp Arg Leu Ala Gly Pro Gly Ser
            340                 345                 350

Glu Lys Tyr Ser Asp Asp Thr Lys Tyr Thr Asp Gly Leu Pro Ala Ala
            355                 360                 365

Asp Leu Ile Pro Pro Pro Leu Lys Pro Arg Lys Val Trp Ile Ile Tyr
    370                 375                 380

Ser Ala Asp His Pro Leu Tyr Val Asp Val Val Leu Lys Phe Ala Gln
385                 390                 395                 400

Phe Leu Leu Thr Ala Cys Gly Thr Glu Val Ala Leu Asp Leu Leu Glu
            405                 410                 415
```

```
Glu Gln Ala Ile Ser Glu Ala Gly Val Met Thr Trp Val Gly Arg Gln
                420                 425                 430

Lys Gln Glu Met Val Glu Ser Asn Ser Lys Ile Ile Val Leu Cys Ser
            435                 440                 445

Arg Gly Thr Arg Ala Lys Trp Gln Ala Leu Leu Gly Arg Gly Ala Pro
        450                 455                 460

Val Arg Leu Arg Cys Asp His Gly Lys Pro Val Gly Asp Leu Phe Thr
465                 470                 475                 480

Ala Ala Met Asn Met Ile Leu Pro Asp Phe Lys Arg Pro Ala Cys Phe
                485                 490                 495

Gly Thr Tyr Val Val Cys Tyr Phe Ser Glu Val Ser Cys Asp Gly Asp
            500                 505                 510

Val Pro Asp Leu Phe Gly Ala Ala Pro Arg Tyr Pro Leu Met Asp Arg
        515                 520                 525

Phe Glu Glu Val Tyr Phe Arg Ile Gln Asp Leu Glu Met Phe Gln Pro
530                 535                 540

Gly Arg Met His Arg Val Gly Glu Leu Ser Gly Asp Asn Tyr Leu Arg
545                 550                 555                 560

Ser Pro Gly Gly Arg Gln Leu Arg Ala Ala Leu Asp Arg Phe Arg Asp
                565                 570                 575

Trp Gln Val Arg Cys Pro Asp Trp Phe Glu Cys Glu Asn Leu Tyr Ser
            580                 585                 590

Ala Asp Asp Gln Asp Ala Pro Ser Leu Asp Glu Glu Val Phe Glu Glu
                595                 600                 605

Pro Leu Leu Pro Pro Gly Thr Gly Ile Val Lys Arg Ala Pro Leu Val
        610                 615                 620

Arg Glu Pro Gly Ser Gln Ala Cys Leu Ala Ile Asp Pro Leu Val Gly
625                 630                 635                 640

Glu Glu Gly Gly Ala Ala Val Ala Lys Leu Glu Pro His Leu Gln Pro
                645                 650                 655

Arg Gly Gln Pro Ala Pro Gln Pro Leu His Thr Leu Val Leu Ala Ala
            660                 665                 670

Glu Glu Gly Ala Leu Val Ala Ala Val Glu Pro Gly Pro Leu Ala Asp
        675                 680                 685

Gly Ala Ala Val Arg Leu Ala Leu Ala Gly Glu Gly Glu Ala Cys Pro
690                 695                 700

Leu Leu Gly Ser Pro Gly Ala Gly Arg Asn Ser Val Leu Phe Leu Pro
705                 710                 715                 720

Val Asp Pro Glu Asp Ser Pro Leu Gly Ser Ser Thr Pro Met Ala Ser
                725                 730                 735

Pro Asp Leu Leu Pro Glu Asp Val Arg Glu His Leu Glu Gly Leu Met
            740                 745                 750

Leu Ser Leu Phe Glu Gln Ser Leu Ser Cys Gln Ala Gln Gly Gly Cys
        755                 760                 765

Ser Arg Pro Ala Met Val Leu Thr Asp Pro His Thr Pro Tyr Glu Glu
770                 775                 780

Glu Gln Arg Gln Ser Val Gln Ser Asp Gln Gly Tyr Ile Ser Arg Ser
785                 790                 795                 800

Ser Pro Gln Pro Pro Glu Gly Leu Thr Glu Met Glu Glu Glu Glu Glu
                805                 810                 815

Glu Glu Gln Asp Pro Gly Lys Pro Ala Leu Pro Leu Ser Pro Glu Asp
            820                 825                 830

Leu Glu Ser Leu Arg Ser Leu Gln Arg Gln Leu Leu Phe Arg Gln Leu
```

```
               835                 840                 845
Gln Lys Asn Ser Gly Trp Asp Thr Met Gly Ser Glu Ser Glu Gly Pro
    850                 855                 860

Ser Ala
865
```

<210> SEQ ID NO 3
<211> LENGTH: 1302
<212> TYPE: DNA
<213> ORGANISM: Artificial Sequence
<220> FEATURE:
<223> OTHER INFORMATION: Synthetic Construct

<400> SEQUENCE: 3

```
atggggccg cacgcagccc gccgtccgct gtcccggggc ccctgctggg gctgctcctg      60
ctgctcctgg gcgtgctggc cccggtggc gcctccctgc actcctgga ccaccgggcg     120
ctggtctgct cccagccggg gctaaactgc acggtcaaga atagtacctg cctggatgac    180
agctggattc accctcgaaa cctgacccc tcctccccaa aggacctgca gatccagctg    240
cactttgccc acacccaaca aggagacctg ttccccgtgg ctcacatcga atggacactg    300
cagacagacg ccagcatcct gtacctcgag ggtgcagagt atctgtcct gcagctgaac    360
accaatgaac gtttgtgcgt caggtttgag tttctgtcca aactgaggca tcaccacagg    420
cggtggcgtt ttaccttcag ccactttgtg gttgaccctg accaggaata tgaggtgacc    480
gttcaccacc tgcccaagcc catccctgat ggggacccaa accaccagtc aagaatttc    540
cttgtgcctg actgtgagca cgccaggatg aaggtaacca cgccatgcat gagctcaggc    600
agcctgtggg accccaacat caccgtggag accctggagg ccaccagct gcgtgtgagc    660
ttcaccctgt ggaacgaatc tacccattac cagatcctgc tgaccagttt ccgcacatg    720
gagaaccaca gttgctttga gcacatgcac cacatacctg cgcccagacc agaagagttc    780
caccagcgat ccaacgtcac actcactcta cgcaacctta aagggtgctg tcgccaccaa    840
gtgcagatcc agcccttctt cagcagctgc ctcaatgact gcctcagaca ctccgcgact    900
gtttcctgcc cagaaatgcc agacactcca gaaccaattc cggactacat gaccggtgga    960
ggtggaggtg gaggtggagg tcagccccga gaaccacagg tgtacaccct gcccccatcc   1020
cgggatgagc tgaccaagaa ccaggtcagc ctgacctgcc tggtcaaagg cttctatccc   1080
agcgacatcg ccgtggagtg ggagagcaat gggcagccgg agaacaacta caagaccacg   1140
cctcccgtgc tggactccga cggctccttc ttcctctaca gcaagctcac cgtggacaag   1200
agcaggtggc agcaggggaa cgtcttctca tgctccgtga tgcatgaggc tctgcacaac   1260
cactacacgc agaagagcct ctccctgtct ccgggtaaat ag                       1302
```

<210> SEQ ID NO 4
<211> LENGTH: 433
<212> TYPE: PRT
<213> ORGANISM: Artificial Sequence
<220> FEATURE:
<223> OTHER INFORMATION: Synthetic Construct

<400> SEQUENCE: 4

```
Met Gly Ala Ala Arg Ser Pro Pro Ser Ala Val Pro Gly Pro Leu Leu
 1               5                   10                  15

Gly Leu Leu Leu Leu Leu Leu Gly Val Leu Ala Pro Gly Gly Ala Ser
             20                  25                  30

Leu Arg Leu Leu Asp His Arg Ala Leu Val Cys Ser Gln Pro Gly Leu
```

```
                35                  40                  45
Asn Cys Thr Val Lys Asn Ser Thr Cys Leu Asp Asp Ser Trp Ile His
            50                  55                  60

Pro Arg Asn Leu Thr Pro Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
                100                 105                 110

Glu Leu Ser Val Leu Gln Leu Asn Thr Asn Glu Arg Leu Cys Val Arg
            115                 120                 125

Phe Glu Phe Leu Ser Lys Leu Arg His His Arg Arg Trp Arg Phe
            130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
            195                 200                 205

Val Glu Thr Leu Glu Ala His Gln Leu Arg Val Ser Phe Thr Leu Trp
210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
            275                 280                 285

Ser Cys Leu Asn Asp Cys Leu Arg His Ser Ala Thr Val Ser Cys Pro
            290                 295                 300

Glu Met Pro Asp Thr Pro Glu Pro Ile Pro Asp Tyr Met Thr Gly Gly
305                 310                 315                 320

Gly Gly Gly Gly Gly Gly Gln Pro Arg Glu Pro Gln Val Tyr Thr
                325                 330                 335

Leu Pro Pro Ser Arg Asp Glu Leu Thr Lys Asn Gln Val Ser Leu Thr
            340                 345                 350

Cys Leu Val Lys Gly Phe Tyr Pro Ser Asp Ile Ala Val Glu Trp Glu
            355                 360                 365

Ser Asn Gly Gln Pro Glu Asn Asn Tyr Lys Thr Thr Pro Pro Val Leu
            370                 375                 380

Asp Ser Asp Gly Ser Phe Phe Leu Tyr Ser Lys Leu Thr Val Asp Lys
385                 390                 395                 400

Ser Arg Trp Gln Gln Gly Asn Val Phe Ser Cys Ser Val Met His Glu
                405                 410                 415

Ala Leu His Asn His Tyr Thr Gln Lys Ser Leu Ser Leu Ser Pro Gly
            420                 425                 430

Lys

<210> SEQ ID NO 5
<211> LENGTH: 9
```

<212> TYPE: PRT
<213> ORGANISM: Artificial Sequence
<220> FEATURE:
<223> OTHER INFORMATION: Synthetic Construct

<400> SEQUENCE: 5

Gly Gly Gly Gly Gly Gly Gly Gly Gly
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Glu Glu Glu Glu Glu Glu Glu Glu Glu
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Ser Ser Ser Ser Ser Ser Ser Ser Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Construct

<400> SEQUENCE: 8

Gly Gly Gly Gly Gly Cys Pro Pro Cys
1               5

<210> SEQ ID NO 9
<211> LENGTH: 15
<212> TYPE: PRT
<213> ORGANISM: Artificial Sequence
<220> FEATURE:
<223> OTHER INFORMATION: Synthetic Construct

<400> SEQUENCE: 9

Gly Gly Gly Gly Ser Gly Gly Gly Gly Ser Gly Gly Gly Gly Ser
1               5                   10                  15

<210> SEQ ID NO 10
<211> LENGTH: 13
<212> TYPE: PRT
<213> ORGANISM: Artificial Sequence
<220> FEATURE:
<223> OTHER INFORMATION: Synthetic Construct

<400> SEQUENCE: 10

Ser Cys Val Pro Leu Met Arg Cys Gly Gly Cys Cys Asn
1               5                   10

<210> SEQ ID NO 11
<211> LENGTH: 14
<212> TYPE: PRT

```
<213> ORGANISM: Artificial Sequence
<220> FEATURE:
<223> OTHER INFORMATION: Synthetic Construct

<400> SEQUENCE: 11

Pro Ser Cys Val Pro Leu Met Arg Cys Gly Gly Cys Cys Asn
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Synthetic Construct

<400> SEQUENCE: 12

Gly Asp Leu Ile Tyr Arg Asn Gln Lys
1               5

<210> SEQ ID NO 13
<211> LENGTH: 23
<212> TYPE: PRT
<213> ORGANISM: Artificial Sequence
<220> FEATURE:
<223> OTHER INFORMATION: Synthetic Construct

<400> SEQUENCE: 13

Gly Gly Gly Gly Gly Gly Gly Gly Pro Ser Cys Val Pro Leu Met
1               5                   10                  15

Arg Cys Gly Gly Cys Cys Asn
            20
```